(12) United States Patent
Lahm

(10) Patent No.: US 7,683,201 B2
(45) Date of Patent: Mar. 23, 2010

(54) QUINAZOLINE(DI)ONES FOR INVERTEBRATE PEST CONTROL

(75) Inventor: George Philip Lahm, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 965 days.

(21) Appl. No.: 11/417,454

(22) Filed: May 4, 2006

(65) Prior Publication Data

US 2006/0194961 A1 Aug. 31, 2006

Related U.S. Application Data

(62) Division of application No. 10/496,724, filed as application No. PCT/US03/01482 on Jan. 16, 2003, now Pat. No. 7,241,767.

(60) Provisional application No. 60/350,632, filed on Jan. 22, 2002.

(51) Int. Cl.
C07C 255/50 (2006.01)
(52) U.S. Cl. .................................... 558/415
(58) Field of Classification Search ................. 562/458; 558/415
See application file for complete search history.

(56) References Cited

U.S. PATENT DOCUMENTS

| | | | |
|---|---|---|---|
| 3,041,336 A | 6/1962 | Teufel | |
| 3,092,631 A | 6/1963 | Song et al. | |
| 3,739,009 A | 6/1973 | Sturm et al. | |
| 3,840,540 A | 10/1974 | Dominy et al. | |
| 4,137,325 A | 1/1979 | Sellstedt et al. | |
| 4,175,184 A | 11/1979 | Merkle et al. | |
| 4,340,417 A | 7/1982 | Theissen | |
| 4,537,966 A | 8/1985 | Murray | |
| 5,985,837 A * | 11/1999 | Ritter et al. | 514/18 |
| 5,998,424 A | 12/1999 | Galemmo, Jr. et al. | |
| 6,020,357 A | 2/2000 | Pinto et al. | |
| 6,403,620 B1 | 6/2002 | Galemmo, Jr. et al. | |
| 6,548,512 B1 | 4/2003 | Pinto et al. | |
| 6,602,895 B2 | 8/2003 | Galemmo, Jr. et al. | |
| 6,747,947 B2 | 6/2004 | Lahm et al. | |
| 6,965,032 B2 | 11/2005 | Freudenberger | |
| 6,995,178 B2 | 2/2006 | Lahm et al. | |
| 7,038,057 B2 | 5/2006 | Annis et al. | |
| 7,087,598 B2 | 8/2006 | Clark | |
| 7,148,217 B2 | 12/2006 | Selby | |
| 7,157,475 B2 | 1/2007 | Clark | |
| 7,179,824 B2 | 2/2007 | Zimmerman | |
| 7,199,138 B2 | 4/2007 | Finkelstein et al. | |
| 7,232,836 B2 | 6/2007 | Lahm et al. | |
| 7,288,554 B2 | 10/2007 | Finkelstein et al. | |
| 2004/0102324 A1 | 5/2004 | Annis et al. | |
| 2004/0110777 A1 | 6/2004 | Annis et al. | |
| 2004/0209923 A1 | 10/2004 | Berger et al. | |
| 2005/0075372 A1 | 4/2005 | Lahm et al. | |

FOREIGN PATENT DOCUMENTS

| | | |
|---|---|---|
| DE | 1543332 | 8/1969 |
| DE | 2444822 A | 4/1976 |
| DE | 2652144 A | 5/1978 |
| DE | 2710382 | 12/1983 |
| EP | 0 991 625 B1 | 6/2005 |
| FR | 1516600 A | 3/1968 |
| GB | 1171999 A | 11/1969 |
| GB | 1178322 | 1/1970 |
| GB | 1511728 A | 5/1978 |
| IT | 869213 | 8/1970 |
| NL | 6603319 | 9/1967 |
| WO | WO 98/57937 | 6/1998 |
| WO | WO 98/28269 | 7/1998 |
| WO | WO 99/32433 | 7/1999 |
| WO | WO 00/69823 | 11/2000 |
| WO | WO 01/05784 | 1/2001 |
| WO | WO 01/56989 | 8/2001 |

OTHER PUBLICATIONS

Peter H. Gore et al., "Friedel-Crafts Reactions. Part XXV. Acetylation and Benzoylation of Iodobenzene and of o-, m-, and p-Iodotoluenes", J.C.S. Perkin I, 1973, 2940-2948.

Milton J. Kornet, "Synthesis and Anticonvulsant Activity of 3-Alkyl-3,4-dihydro-2(1H)-quinazolinones", J. Heterocyclic Chem., 1992, 103-105, 29.

Fred E. Sheibley, "6,8-Diiodobenzoyleneurea, and the Interaction of 5,7-Dihalogenoisatoic Anhydrides with Ammonia and with Ethyleamine. 3-Ethyl-6,8-dihalogenobenzoyleneureas", J. Org. Chem, 1947, 743-751, 12.

* cited by examiner

*Primary Examiner*—James O. Wilson
*Assistant Examiner*—Tamthom N Truong

(57) ABSTRACT

Compounds of Formula I including all geometric and stereoisomers, N-oxides, and agriculturally suitable salts thereof, are disclosed which are useful as invertebrate pest control agents

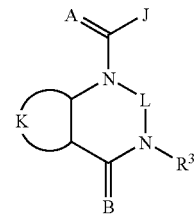

wherein A, B, J, K, L and $R^3$ are as defined in the disclosure.

Also disclosed are compositions for controlling an invertebrate pest comprising a biologically effective amount of a compound of Formula I an N-oxide thereof or a suitable salt thereof and at least one additional component selected from the group consisting of surfactants, solid diluents and liquid diluents.

Also disclosed are methods for controlling an invertebrate pest comprising contacting the invertebrate pest or its environment with a biologically effective amount of a compound of Formula I, its N-oxide or a suitable salt of the compound (e.g., as a composition described herein).

4 Claims, No Drawings

QUINAZOLINE(DI)ONES FOR INVERTEBRATE PEST CONTROL

BACKGROUND OF THE INVENTION

This invention relates to certain quinazoline(di)ones, their N-oxides, agriculturally suitable salts and compositions thereof, and a method of use for controlling invertebrate pests in both agronomic and nonagronomic environments.

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

WO01/070671 discloses N-acyl anthranilic acid derivatives of Formula i as arthropodicides

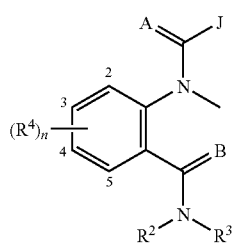

i wherein, inter alia, A and B are independently O or S; J is an optionally substituted phenyl ring, 5- or 6-membered heteroaromatic ring, naphthyl ring system or an aromatic 8-, 9- or 10-membered fused heterobicyclic ring system; $R^1$ and $R^3$ are independently H or optionally substituted $C_1$-$C_6$ alkyl; $R^2$ is H or $C_1$-$C_6$ alkyl; each $R^4$ is independently H, $C_1$-$C_6$ alkyl, $C_1$-$C_6$ haloalkyl, halogen or CN; and n is 1 to 4.

SUMMARY OF THE INVENTION

This invention is directed to compounds of Formula I including all geometric and stereoisomers, their N-oxides and suitable salts thereof,

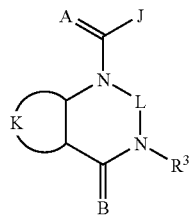

I wherein
A and B are independently O or S;
J is a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 substituents independently selected from $R^5$;
K is, together with the two contiguous linking carbon atoms, a fused phenyl, a fused pyridinyl or a fused pyrimidinyl ring selected from the group consisting of K-1, K-2, K-3, K-4, K-5 and K-6, each optionally substituted with 1 to 4 substituents independently selected from $R^4$

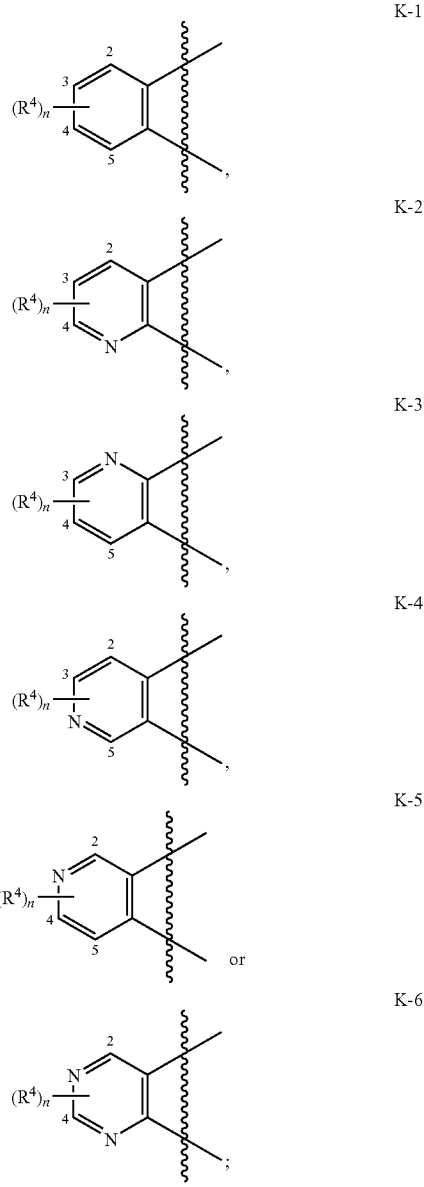

L is a direct bond; or a linking chain of 1 to 3 members selected from carbon, nitrogen, oxygen and sulfur, optionally including one or two chain members as C(=E), SO or S(O)$_2$, and optionally substituted with one to three substituents independently selected from $R^{13}$;
E is O, S or $NR^8$;
$R^3$ is H; G; $C_1$-$C_6$ alkyl, $C_2$-$C_6$ alkenyl, $C_2$-$C_6$ alkynyl, $C_3$-$C_6$ cycloalkyl, each optionally substituted with 1 to 5 substituents independently selected from the group consisting of G, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl, phenyl, phenoxy and 5- or 6-membered heteroaromatic ring, each phenyl, phenoxy and 5- or 6-membered heteroaromatic ring optionally substituted with one to three substituents independently selected from $R^6$; or phenyl optionally substituted with 1 to 3 substituents independently selected from $R^6$;

G is a 5- or 6-membered nonaromatic carbocyclic or heterocyclic ring, optionally including one or two ring members selected from the group consisting of C(=O), SO and S(O)$_2$ and optionally substituted with 1 to 4 substituents independently selected from $R^{12}$;

each $R^4$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, NO$_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_1$-$C_4$ alkoxyalkyl, $C_1$-$C_4$ hydroxyalkyl, C(O)$R^{10}$, CO$_2R^{10}$, C(O)NR$^{10}R^{11}$, NR$^{10}R^{11}$, N(R$^{11}$)CO$_2R^{10}$ or $C_3$-$C_6$ trialkylsilyl; or each $R^4$ is independently a phenyl, benzyl, phenoxy or a 5- or 6-membered heteroaromatic ring, each ring optionally substituted with one to three substituents independently selected from $R^6$;

each $R^5$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, CO$_2$H, CONH$_2$, NO$_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylsulfonyloxy, $C_1$-$C_4$ haloalkylthio, $C_1$-$C_4$ haloalkylsulfinyl, $C_1$-$C_4$ haloalkylsulfonyl, $C_1$-$C_4$ haloalkylsulfonyloxy, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or each $R^5$ is independently a phenyl, benzyl, benzoyl, phenoxy, 5- or 6-membered heteroaromatic ring or an aromatic 8-, 9- or 10-membered fused heterobicyclic ring system, each ring or ring system optionally substituted with one to three substituents independently selected from $R^6$; or two $R^5$ groups when attached to adjacent carbon atoms are taken together as —OCF$_2$O—, —CF$_2$CF$_2$O— or —OCF$_2$CF$_2$O—;

each $R^6$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, NO$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^8$ is H; $C_1$-$C_6$ alkyl, $C_2$-$C_6$ alkenyl, $C_2$-$C_6$ alkynyl or $C_3$-$C_6$ cycloalkyl, each optionally substituted with 1 to 5 substituents independently selected from the group consisting of halogen, CN, NO$_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl, a phenyl ring and a 5- or 6-membered heteroaromatic ring, each ring optionally substituted with one to three substituents independently selected from $R^6$; CN; NO$_2$; $C_2$-$C_6$ alkoxycarbonyl; $C_1$-$C_4$ alkylsulfonyl; or phenyl or phenylsulfonyl optionally substituted with 1 to 3 substituents independently selected from $R^6$;

each $R^{10}$ is independently H, $C_1$-$C_4$ alkyl or $C_1$-$C_4$ haloalkyl;

each $R^{11}$ is independently H or $C_1$-$C_4$ alkyl;

each $R^{12}$ is independently $C_1$-$C_2$ alkyl, halogen, CN, NO$_2$ or $C_1$-$C_2$ alkoxy;

each $R^{13}$ is independently $C_1$-$C_4$ alkyl, $C_1$-$C_4$ haloalkyl, halogen, CN, COOH, $C_1$-$C_4$ alkoxy, $C_1$-$C_4$ haloalkoxy, $C_2$-$C_6$ alkoxycarbonyl, $C_2$-$C_6$ alkoxycarbonylalkyl; or each $R^{13}$ is a phenyl or a 5- or 6-membered heteroaromatic ring, each ring optionally substituted with one to three substituents independently selected from $R^6$; and n is 0,1,2,3 or 4.

This invention also pertains to a method for controlling an invertebrate pest comprising contacting the invertebrate pest or its environment with a biologically effective amount of a compound of Formula I, its N-oxide or a suitable salt of the compound (e.g., as a composition described herein). This invention also relates to such a method wherein the invertebrate pest or its environment is contacted with a biologically effective amount of a compound of Formula I or a composition comprising a compound of Formula I and a biologically effective amount of at least one additional compound or agent for controlling invertebrate pests.

This invention also pertains to a composition for controlling an invertebrate pest comprising a biologically effective amount of a compound of Formula I, its N-oxide or a suitable salt of the compound and at least one additional component selected from the group consisting of a surfactant, a solid diluent and a liquid diluent. This invention also pertains to a composition comprising a biologically effective amount of a compound of Formula I, its N-oxide or a suitable salt of the compound and an effective amount of at least one additional biologically active compound or agent.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include CH$_3$OCH$_2$, CH$_3$OCH$_2$CH$_2$, CH$_3$CH$_2$OCH$_2$, CH$_3$CH$_2$CH$_2$CH$_2$OCH$_2$ and CH$_3$CH$_2$OCH$_2$CH$_2$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include CH$_3$S(O), CH$_3$CH$_2$S(O), CH$_3$CH$_2$CH$_2$S(O), (CH$_3$)$_2$CHS(O) and the different butylsulfinyl, pentylsulfinyl and hexylsulfinyl isomers.

Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. Examples of "alkylsulfonyloxy" include $CH_3S(O)_2O$, $CH_3CH_2S(O)_2O$, $CH_3CH_2CH_2S(O)_2O$, $(CH_3)_2CHS(O)_2O$ and the different butylsulfonyloxy, pentylsulfonyloxy and hexylsulfonyloxy isomers. "Alkylamino", "dialkylamino", "alkenylthio", "alkenylsulfinyl", "alkenylsulfonyl", "alkynylthio", "alkynylsulfinyl", "alkynylsulfonyl", and the like, are defined analogously to the above examples. "Cycloalkyl" includes, for example, cyclopropyl, cyclobutyl, cyclopentyl, and cyclohexyl.

"Aromatic" indicates that each of ring atoms is essentially in the same plane and has a p-orbital perpendicular to the ring plane, and in which $(4n+2)$ π electrons, when n is 0 or a positive integer, are associated with the ring to comply with Hückel's rule. The term "aromatic ring system" denotes fully unsaturated carbocycles and heterocycles in which at least one ring of a polycyclic ring system is aromatic. The term "aromatic carbocyclic ring or ring system" includes fully aromatic carbocycles and carbocycles in which at least one ring of a polycyclic ring system is aromatic (e.g. phenyl and naphthyl). The term "aryl" refers to any optionally substituted aromatic ring or ring system. The term "nonaromatic carbocyclic ring or ring system" denotes fully saturated carbocycles as well as partially or fully unsaturated carbocycles where the Hückel rule is not satisfied by any of the rings in the ring system. The term "hetero" in connection with rings or ring systems refers to a ring or ring system in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs. The term "heteroaromatic ring or ring system" includes fully aromatic heterocycles and heterocycles in which at least one ring of a polycyclic ring system is aromatic (where aromatic indicates that the Hückel rule is satisfied). The term "nonaromatic heterocyclic ring or ring system" denotes fully saturated heterocycles as well as partially or fully unsaturated heterocycles where the Hückel rule is not satisfied by any of the rings in the ring system. The heterocyclic ring or ring system can be attached through any available carbon or nitrogen by replacement of a hydrogen on said carbon or nitrogen.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", "haloalkylthio", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$. Examples of "haloalkylsulfonyloxy" include $CF_3S(O)_2O$, $CCl_3S(O)_2O$, $CF_3CH_2S(O)_2O$ and $CF_3CF_2S(O)_2O$.

Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. Examples of "alkoxycarbonylalkyl" include $CH_3OC(=O)CH_2$, $CH_3CH_2OC(=O)CH_2$, $CH_3CH_2CH_2OC(=O)CH_2CH_2$ and $(CH_3)_2CHOC(=O)CH_2$. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylamincarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $CH_3CH_2CH_2(CH_3)NC(=O)$ and $(CH_3)_2CHN(CH_3)C(=O)$.

The total number of carbon atoms in a substituent group is indicated by the "$C_i$-$C_j$" prefix where i and j are numbers from 1 to 6. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

The term "optionally substituted with one to three substituents" and the like indicates that one to three of the available positions on the group can be substituted. When a group contains a substituent which can be hydrogen, for example $R^3$ or $R^8$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol.

As noted above, J is a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 substituents independently selected from $R^5$. The term "optionally substituted" in connection with these J groups refers to groups which are unsubstituted or have at least one non-hydrogen substituent that does not extinguish the biological activity possessed by the unsubstituted analog. An example of phenyl optionally substituted with 1 to 4 $R^5$ is the ring illustrated as U-1 in Exhibit 1, wherein $R^v$ is $R^5$ and r is an integer from 0 to 4. An example of a naphthyl group optionally substituted with 1 to 4 $R^5$ is illustrated as U-85 in Exhibit 1, wherein $R^v$ is $R^5$ and r is an integer from 0 to 4. Examples of 5- or 6-membered heteroaromatic rings optionally substituted with 1 to 4 $R^5$ include the rings U-2 through U-53 illustrated in Exhibit 1 wherein $R^v$ is $R^5$ and r is an integer from 0 to 4. Note that J-1 through J-13 below also denote 5- or 6-membered heteroaromatic rings. Note that U-2 through U-20 are examples of J-1, U-21 through U-35 and U-40 are examples of J-2, U-36 through U-39 are examples of J-3, U-41 through U-48 are examples of J-4 and U-49 through U-53 are examples of J-5. Note that U-11 is equivalent to J-6, U-26 is equivalent to J-7 or J-10, U-42 is equivalent to J-8, U-45 is equivalent to J-9, U-4 is equivalent to J-11 and U-24 is equivalent to J-12 or J-13. Also note that in J-6 through J-13 that $R^7$ and $R^9$ are subsets of $R^5$ of Formula I. Examples of aromatic 8-, 9- or 10-membered fused heterobicyclic ring systems optionally substituted with 1 to 4 substituents independently selected from $R^5$ include U-54 through U-84 illustrated in Exhibit 1 wherein $R^v$ is $R^5$ of Formula I and r is an integer from 0 to 4.

$R^v$ is attached to these rings through any available carbon or nitrogen by replacement of a hydrogen on said carbon or nitrogen Note that some U groups can only be substituted with less than 4 $R^v$ groups (e.g. U-16 through U-21 and U-32 through U-34 can only be substituted with one $R^v$). Note that when the attachment point between $(R^v)_r$ and the U group is illustrated as floating, $(R^v)_r$ can be attached to any available carbon or nitrogen of the U group. Note that when the attachment point on the U group is illustrated as floating, the U group can be attached to the remainder of Formula I through any available carbon or nitrogen of the U group by replacement of a hydrogen atom.

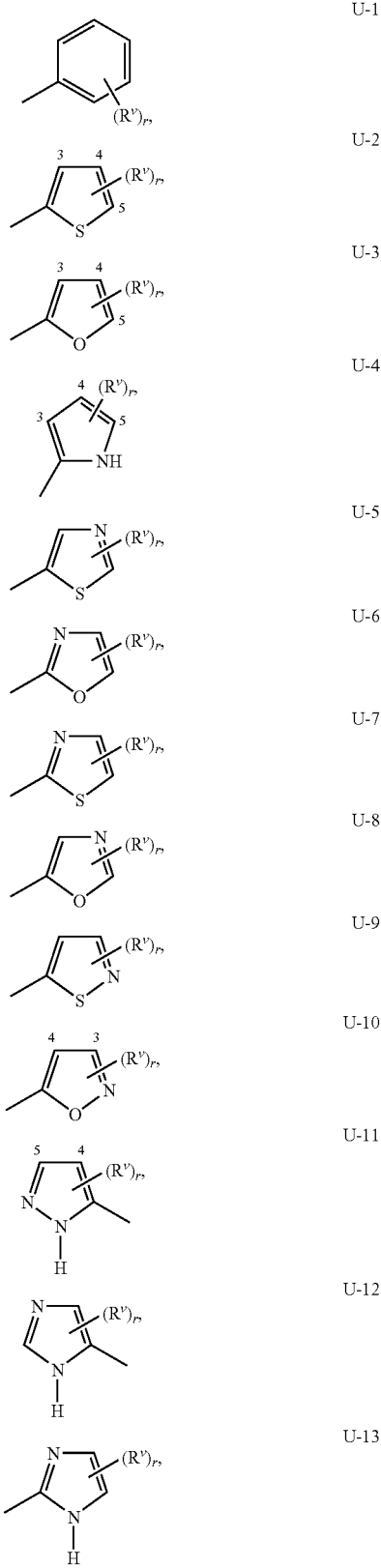

-continued
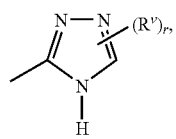 u-14
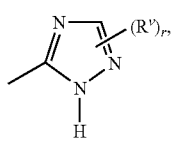 U-15
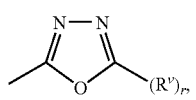 U-16
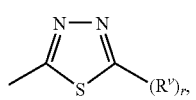 U-17
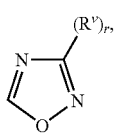 U-18
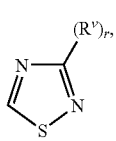 U-19
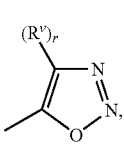 J-20
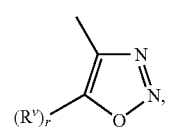 U-21
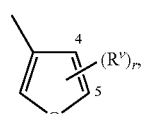 U-22
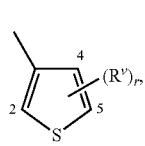 U-23
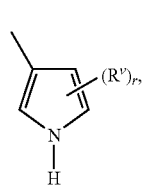 U-24
-continued
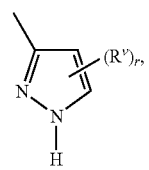 U-25
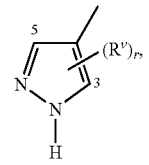 U-26
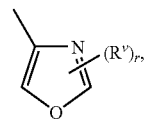 U-27
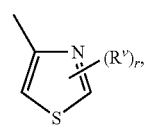 U-28
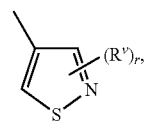 U-29
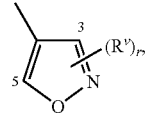 U-30
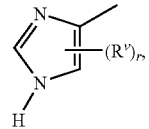 U-31
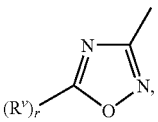 U-32
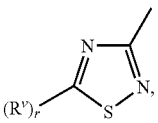 U-33
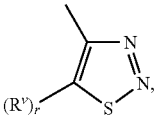 U-34
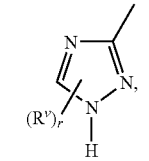 J-35

-continued
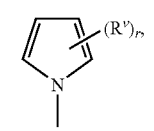 U-36
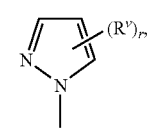 U-37
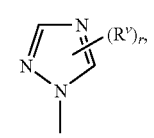 U-38
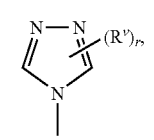 U-39
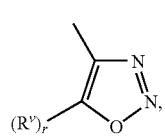 U-40
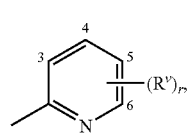 U-41
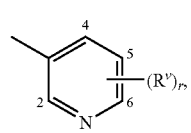 U-42
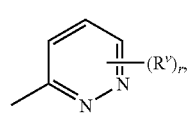 U-43
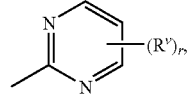 U-44
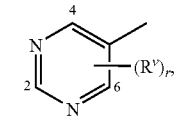 U-45
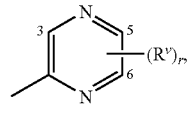 U-46
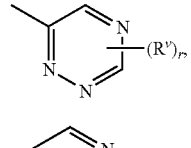 U-47
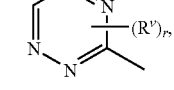 U-48
-continued
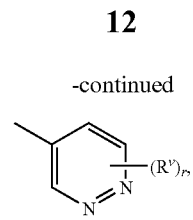 U-49
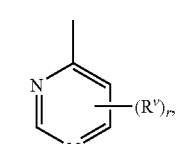 U-50
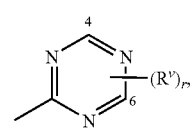 U-51
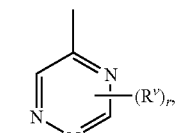 U-52
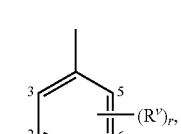 U-53
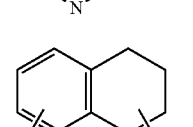 U-54
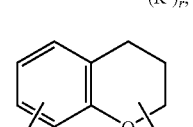 U-55
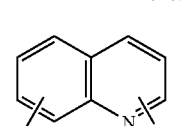 U-56
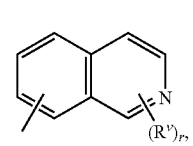 U-57
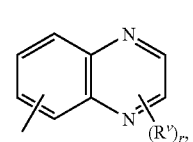 U-58
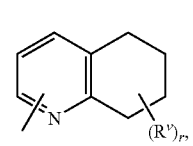 U-59

-continued
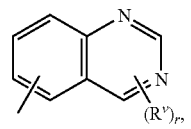 U-60
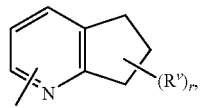 U-61
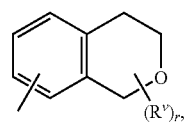 U-62
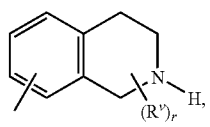 U-63
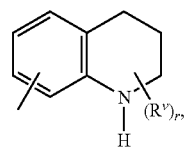 U-64
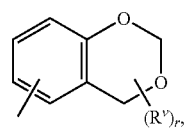 U-65
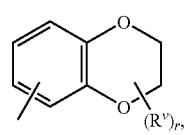 U-66
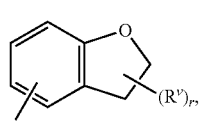 U-67
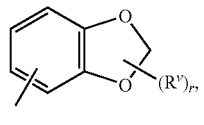 U-68
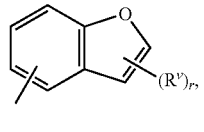 U-69
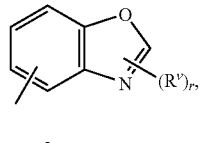 U-70
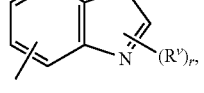 U-71
-continued
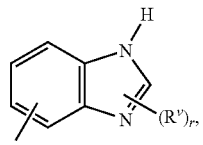 U-72
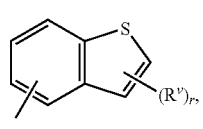 U-73
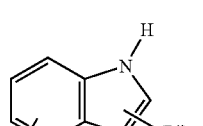 U-74
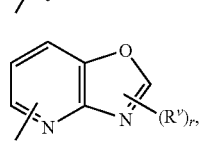 U-75
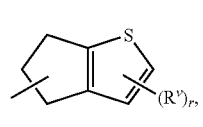 U-76
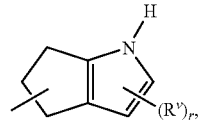 U-77
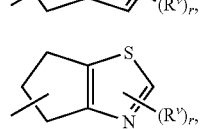 U-78
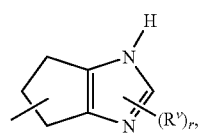 U-79
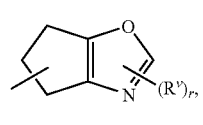 U-80
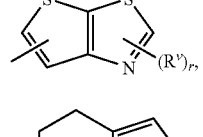 U-81
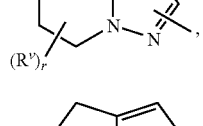 U-82
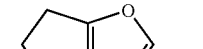 U-83
U-84

-continued

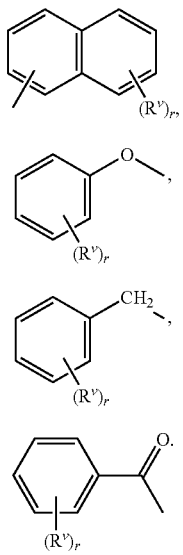

U-85

U-86

U-87

U-88

As noted above K is, together with the two contiguous linking carbon atoms, a fused phenyl, a fused pyridinyl ring or a fused pyrimidinyl ring optionally substituted with 1 to 4 substituents independently selected from $R^4$. The term "optionally substituted" in connection with these K groups refers to groups which are unsubstituted or have at least one non-hydrogen substituent that does not extinguish the biological activity possessed by the unsubstituted analog. Examples of such K groups include the rings illustrated as K-1 through K-6 in Exhibit 2. Note that K-2 through K-5 can be optionally substituted with one to three substituents independently selected from $R^4$. Also note that K-6 can be optionally substituted with one to two substituents independently selected from $R^4$. In the exemplified K groups, the upper right bond is attached through the available linking carbon atom to the nitrogen atom of the N(L)-C(=A)J portion of Formula I and the lower right bond is attached through the available linking carbon atom to the carbon atom of the C(=B)N(L)$R^3$ portion of Formula I. The wavy line indicates that the K-ring is attached to the remainder of Formula I as illustrated below.

Exhibit 2

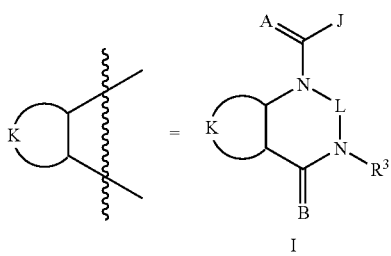

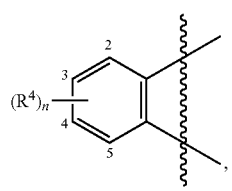

K-1

-continued

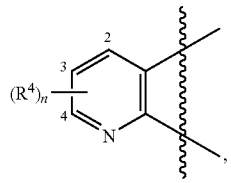

K-2

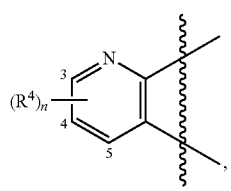

K-3

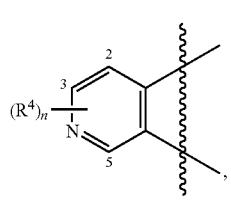

K-4

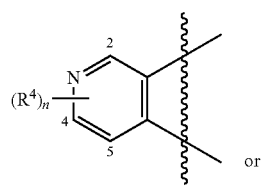

K-5 or

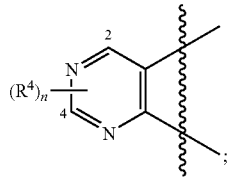

K-6

Preferred K-rings are K-1, K-2, K-5 and K-6. Most preferred is K-1.

As noted above, L is a direct bond; or a linking chain of 1 to 3 members selected from carbon, nitrogen, oxygen and sulfur, optionally including one or two chain members as C(=E), SO or S(O)$_2$, and optionally substituted with one to three substituents independently selected from $R^{13}$. The term "optionally substituted" in connection with these L groups refers to groups which are unsubstituted or have at least one non-hydrogen substituent that does not extinguish the biological activity possessed by the unsubstituted analog. Examples of L include the groups L-1 through L-17 illustrated in Exhibit 3. In L-17, t is an integer from 1 to 3. Although $R^6$ groups are shown in the structure L-17, it is noted that they do not need to be present since they are optional substituents. Preferred L groups are L-1, L-6, L-7, L-9 and L-10.

—C(=O)—  L-1

—C(=S)—  L-2

—C(=N$R^8$)—  L-3

-continued

| | |
|---|---|
| —S(O)— | L-4 |
| —SO₂— | L-5 |
| —CH₂— | L-6 |
| —CH₂CH₂— | L-7 |
| —CH₂CH₂CH₂— | L-8 |
| —CH(CH₃)— | L-9 |
| —C(CH₃)₂— | L-10 |
| —CH(OCH₃)— | L-11 |
| —CH(OCH₃)₂— | L-12 |
| —CF₂— | L-13 |
| —CF₂CF₂— | L-14 |
| —CH(CF₃)— | L-15 |
| —CH(CCl₃)— | L-16 |

L-17

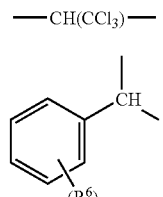

As noted above, $R^3$ can be (among others) $C_1$-$C_6$ alkyl, $C_2$-$C_6$ alkenyl, $C_2$-$C_6$ alkynyl, $C_3$-$C_6$ cycloalkyl, each optionally substituted with one to five substituents independently selected from the group consisting of a phenyl ring and 5- or 6-membered heteroaromatic ring, each ring optionally substituted with one to three substituents independently selected from $R^6$. Examples of such rings incorporated into said $R^3$ groups include the rings illustrated as U-1 through U-53 and U-86 illustrated in Exhibit 1, except that such rings are optionally substituted with 1 to 3 substituents independently selected from $R^6$ rather than $(R^v)_r$ and are attached to an $R^3$ group selected from the list immediately above.

As noted above, $R^3$ can be (among others) G; or $C_1$-$C_6$ alkyl, $C_2$-$C_6$ alkenyl, $C_2$-$C_6$ alkynyl, $C_3$-$C_6$ cycloalkyl, each optionally substituted with G; wherein G is a 5- or 6-membered nonaromatic carbocyclic or heterocyclic ring, optionally including one or two ring members selected from the group consisting of C(=O), SO or S(O)₂ and optionally substituted with 1 to 4 substituents independently selected from $R^{12}$. The term "optionally substituted" in connection with these G groups refers to groups which are unsubstituted or have at least one non-hydrogen substituent that does not extinguish the biological activity possessed by the unsubstituted analog. The optional substituents can be attached to any available carbon by replacing a hydrogen atom. Examples of 5- or 6-membered nonaromatic carbocyclic rings as G include the rings illustrated as G-1 through G-8 of Exhibit 3. Examples of 5- or 6-membered nonaromatic heterocyclic rings as G include the rings illustrated as G-9 through G-38 of Exhibit 4. Note that when G comprises a ring selected from G-31 through G-34, G-37 and G-38, $Q^1$ is selected from O, S or N. Note that when G is G-11, G13, G-14, G16, G-23, G-24, G-30 through G-34, G-37 and G-38 and $Q^1$ is N, the nitrogen atom can complete its valence by substitution with either H or $C_1$-$C_2$ alkyl. Note that when the attachment point on the G group is illustrated as floating, the G group can be attached to the remainder of Formula I through any available carbon of the G group by replacement of a hydrogen atom.

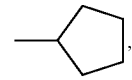  G-1

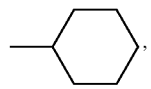  G-2

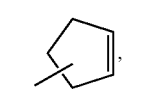  G-3

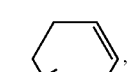  G-4

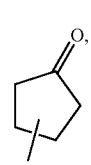  G-5

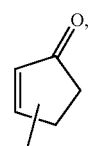  G-6

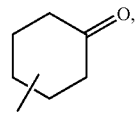  G-7

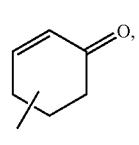  G-8

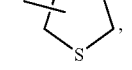  G-9

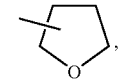  G-10

  G-11

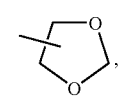  G-12

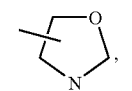  G-13

-continued

G-14 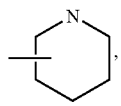

G-15 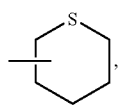

G-16 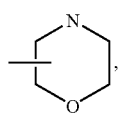

G-17 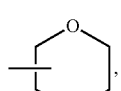

G-18 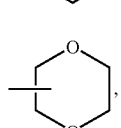

G-19 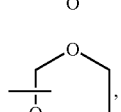

G-20 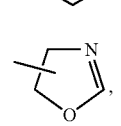

G-21 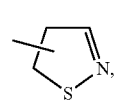

G-22 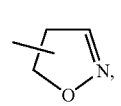

G-23 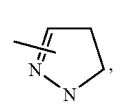

G-24 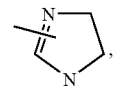

G-25 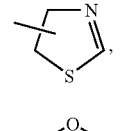

G-26 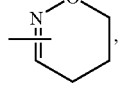

G-27 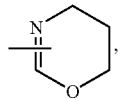

-continued

G-28 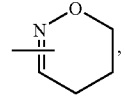

G-29 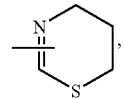

G-30 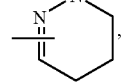

G-31 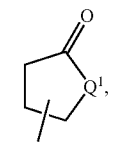

G-32 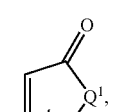

G-33 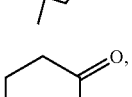

G-34 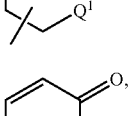

G-35 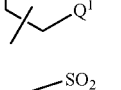

G-36 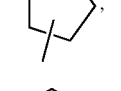

G-37 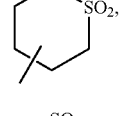 or

G-38 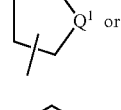

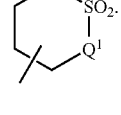

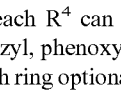

As noted above, each $R^4$ can be independently (among others) a phenyl, benzyl, phenoxy or 5- or 6-membered heteroaromatic ring, each ring optionally substituted with one to three substituents independently selected from $R^6$. Examples of such $R^4$ groups include the rings or ring systems illustrated as U-1 through U-53, U-86 and U-87 illustrated in Exhibit 1, except that such rings are optionally substituted with 1 to 3 substituents independently selected from $R^6$ rather than $(R^v)_r$.

As noted above, each $R^5$ can be independently (among others) a phenyl, benzyl, benzoyl, phenoxy, 5- or 6-membered heteroaromatic ring or an aromatic 8-, 9- or 10-membered fused heterobicyclic ring system, each ring optionally substituted with one to three substituents independently selected from $R^6$. Examples of such $R^5$ groups include the rings or ring systems illustrated as U-1 through U-88 illustrated in Exhibit 1, except that such rings are optionally substituted with 1 to 3 substituents independently selected from $R^6$ rather than $(R^v)_r$.

Preferred compounds for reasons of better activity and/or ease of synthesis are:

Preferred 1. Compounds of Formula I above, their N-oxides and agriculturally suitable salts thereof, wherein A and B are both O and J is a phenyl group optionally substituted with 1 to 4 $R^5$.

Preferred 2. Compounds of Preferred 1 wherein
one $R^4$ group is attached to the K ring at either the 2-position or the 5-position, and said $R^4$ is $C_1$-$C_4$ alkyl, $C_1$-$C_4$ haloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl or $C_1$-$C_4$ haloalkylsulfonyl; and each $R^5$ is independently halogen, $C_1$-$C_4$ alkyl, $C_1$-$C_4$ alkoxy, $C_1$-$C_4$ haloalkyl, CN, $NO_2$, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; or each $R^5$ is independently a phenyl or a 5- or 6-membered heteroaromatic ring, each ring optionally substituted with one to three substituents independently selected from $R^6$; or two $R^5$ groups when attached to adjacent carbon atoms are taken together as —$OCF_2O$—, —$CF_2CF_2O$— or —$OCF_2CF_2O$—.

Preferred 3. Compounds of Preferred 2 wherein
$R^3$ is $C_1$-$C_4$ alkyl optionally substituted with 1 to 5 substituents independently selected from the group consisting of halogen, CN, $OCH_3$ and $S(O)_pCH_3$;

one $R^4$ group is attached to the K ring at the 2-position and said $R^4$ is $CH_3$, $CF_3$, $OCF_3$, $OCHF_2$, $S(O)_pCF_3$, $S(O)_pCHF_2$, CN or halogen;

an optionally second $R^4$ is F, Cl, Br, I, CN or $CF_3$;

each $R^5$ is independently halogen, methyl, $CF_3$, $OCF_3$, $OCHF_2$, $S(O)_pCF_3$, $S(O)_pCHF_2$, $OCH_2CF_3$, $OCF_2CHF_2$, $S(O)_pCH_2CF_3$ or $S(O)_pCF_2CHF_2$; or a phenyl, pyrazole, imidazole, triazole, pyridine or pyrimidine ring, each ring optionally substituted with 1 to 3 substituents independently selected from $C_1$-$C_4$ alkyl, $C_1$-$C_4$ haloalkyl, halogen and CN; and p is 0, 1 or 2.

Preferred 4. Compounds of Preferred 3 wherein $R^3$ is $C_1$-$C_4$ alkyl.

Preferred 5. Compounds of Formula I above, their N-oxides and agriculturally suitable salts thereof, wherein
A and B are both O;
J is a 5- or 6-membered heteroaromatic ring selected from the group consisting of J-1, J-2, J-3, J-4 and J-5, each J optionally substituted with 1 to 3 substituents independently selected from $R^5$

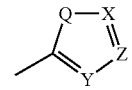

J-1

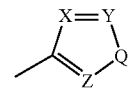

J-2

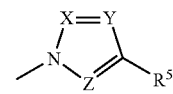

J-3

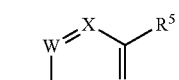

J-4

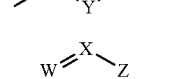

J-5

Q is O, S, NH or $NR^5$; and
W, X, Y and Z are independently N, CH or $CR^5$, provided that in J-4 and J-5 at least one of W, X, Y or Z is N.

Preferred 6. Compounds of Preferred 5 wherein
one $R^4$ group is attached to the K ring at either the 2-position or the 5-position, and said $R^4$ is $C_1$-$C_4$ alkyl, $C_1$-$C_4$ haloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, or $C_1$-$C_4$ haloalkylsulfonyl; and each $R^5$ is independently $C_1$-$C_4$ alkyl, $C_1$-$C_4$ haloalkyl, halogen, CN, $NO_2$, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; or each $R^5$ is independently a phenyl or a 5- or 6-membered heteroaromatic ring, each ring optionally substituted with one to three substituents independently selected from $R^6$.

Preferred 7. Compounds of Preferred 6 wherein
J is selected from the group consisting of

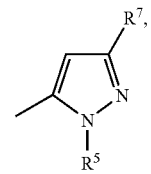

J-6

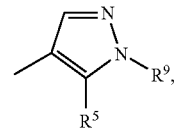

J-7

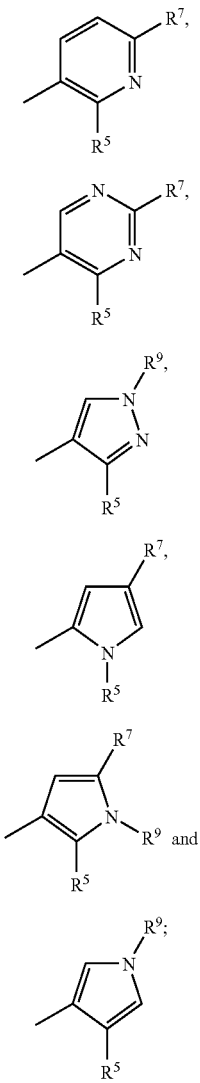

$R^5$ is $C_1$-$C_4$ alkyl, $C_1$-$C_4$ haloalkyl, or

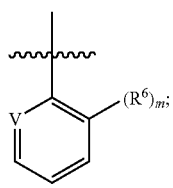

V is N, CH, CF, CCl, CBr or CI;
$R^6$ is $C_1$-$C_6$ alkyl, $C_3$-$C_6$ cycloalkyl, $C_1$-$C_4$ haloalkyl, halogen, CN, $C_1$-$C_4$ alkoxy, $C_1$-$C_4$ haloalkoxy or $C_1$-$C_4$ haloalkylthio;
$R^7$ is H, $C_1$-$C_6$ alkyl, $C_3$-$C_6$ cycloalkyl, $C_1$-$C_4$ haloalkyl, halogen, CN, $C_1$-$C_4$ alkoxy, $C_1$-$C_4$ haloalkoxy or $C_1$-$C_4$ haloalkylthio;
$R^9$ is H, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl or $C_3$-$C_6$ haloalkynyl; provided $R^7$ and $R^9$ are not both H; and
m is 0 or 1.

Preferred 8. Compounds of Preferred 7 wherein V is N.
Preferred 9. Compounds of Preferred 7 wherein V is CH, CF, CCl or CBr.
Preferred 10. Compounds of Preferred 8 or Preferred 9 wherein
  $R^3$ is H; or $C_1$-$C_4$ alkyl optionally substituted with 1 to 5 substituents independently selected from the group consisting of halogen, CN, $OCH_3$ and $S(O)_pCH_3$;
  one $R^4$ group is attached to the K ring at the 2-position and said $R^4$ is $CH_3$, $CF_3$, $OCF_3$, $OCHF_2$, $S(O)_pCF_3$, $S(O)_pCHF_2$, CN or halogen;
  an optionally second $R^4$ is F, Cl, Br, I, CN or $CF_3$;
  $R^6$ is $C_1$-$C_4$ alkyl, $C_1$-$C_4$ haloalkyl, halogen or CN;
  $R^7$ is H, $CH_3$, $CF_3$, $OCHF_2$, $OCH_2CF_3$ or halogen; and
  p is 0, 1 or 2.
Preferred 11. Compounds of Preferred 10 wherein $R^3$ is H or $C_1$-$C_4$ alkyl; and one $R^4$ group is attached to the 2-position and said $R^4$ is $CH_3$, Cl, Br or I.
Preferred 12. Compounds of Preferred 11 wherein J is J-6; $R^6$ is halogen; and $R^7$ is halogen or $CF_3$.
Preferred 13. Compounds of Preferred 12 wherein V is N; $R^3$ is H or methyl, ethyl, isopropyl or tertiary butyl; and $R^7$ is Br, Cl or $CF_3$.
Preferred 14. Compounds of Preferred 11 wherein J is J-7; $R^6$ is halogen; and $R^9$ is $CF_3$, $CHF_2$, $CH_2CF_3$ or $CF_2CHF_2$.
Preferred 15. Compounds of Preferred 11 wherein J is J-8; $R^6$ is halogen; and $R^7$ is halogen or $CF_3$.
Preferred 16. Compounds of Preferred 11 wherein J is J-9; $R^6$ is halogen; and $R^7$ is $CF_3$.
Preferred 17. Compounds of Preferred 11 wherein J is J-10; $R^6$ is halogen; and $R^9$ is $CF_3$, $CHF_2$, $CH_2CF_3$ or $CF_2CHF_2$.
Preferred 18. Compounds of Preferred 11 wherein J is J-11; $R^6$ is halogen; and $R^7$ is halogen or $CF_3$.
Preferred 19. Compounds of Preferred 11 wherein J is J-12; $R^6$ is halogen; $R^7$ is H, halogen or $CF_3$; and $R^9$ is H, $CF_3$, $CHF_2$, $CH_2CF_3$, or $CF_2CHF_2$.
Preferred 20. Compounds of Preferred 11 wherein J is J-13; $R^6$ is halogen; $R^7$ is H, halogen or $CF_3$; and $R^9$ is H, $CF_3$, $CHF_2$, $CH_2CF_3$ or $CF_2CHF_2$.

Most preferred are compounds of Preferred 13 selected from the group:
  6-Bromo-1-[[3-bromo-1-(3-chloro-2-pyridinyl)-1H-pyrazol-5-yl]carbonyl]-8-methyl-3-(1-methylethyl)-2,4 (1H,3H)-quinazolinedione,
  6-Bromo-1-[[1-(3-chloro-2-pyridinyl)-3-(trifluoromethyl)-1H-pyrazol-5-yl]carbonyl]-3,8-dimethyl-2,4 (1H,3H)-quinazolinedione,
  6-Bromo-1-[[3-bromo-1-(3-chloro-2-pyridinyl)-1H-pyrazol-5-yl]carbonyl]-3,8-dimethyl-2,4(1H,3H)-quinazolinedione,
  1-[[3-Bromo-1-(3-chloro-2-pyridinyl)-1H-pyrazol-5-yl]carbonyl]-2,3-dihydro-8-methyl-3-(1-methylethyl)-4 (1H)-quinazolinone,
  6,8-Dichloro-1-[[3-chloro-1-(3-chloro-2-pyridinyl)-1H-pyrazol-5-yl]carbonyl]-2,3-dihydro-3-(1-methylethyl)-4(1H)-quinazolinone,
  1-[[3-Bromo-1-(3-chloro-2-pyridinyl)-1H-pyrazol-5-yl]carbonyl]-6,8-dichloro-2,3-dihydro-3-(1-methylethyl)-4-(1H)-quinazolinone,
  6,8-Dichloro-1-[[1-(3-chloro-2-pyridinyl)-3-(trifluoromethyl)-1H-pyrazol-5-yl]carbonyl]-2,3-dihydro-3-methyl-4(1H)-quinazolinone,
  6-Chloro-1-[[3-chloro-1-(3-chloro-2-pyridinyl)-1H-pyrazol-5-yl]carbonyl]-2,3-dihydro-8-methyl-3-(1-methylethyl)-4(1H)-quinazolinone, 1-[[3-Bromo-1-(3-chloro-2-pyridinyl)-1H-pyrazol-5-yl]
carbonyl]-6-chloro-2,3-dihydro-8-methyl-3-(1-methyl-
ethyl)-4-(1H)-quinazolinone,
6,8-Dichloro-1-[[1-(3-chloro-2-pyridinyl)-3-(trifluorom-
ethyl)-1H-pyrazol-5-yl]carbonyl]-2,3-dihydro-3-(1-
methylethyl)-4(1H)-quinazolinone,
6-8-Dichloro-1-[[3-chloro-1-(3-chloro-2-pyridinyl)-1H-
pyrazol-5-yl]carbonyl]-2,3-dihydro-3-methyl-4(1H)-
quinazolinone,
1-[[3-Bromo-1-(3-chloro-2-pyridinyl)-1H-pyrazol-5-yl]
carbonyl]-6,8-dichloro-2,3-dihydro-3-methyl-4(1H)-
quinazolinone,
6-Chloro-1-[[1-(3-chloro-2-pyridinyl)-3-(trifluorom-
ethyl)-1H-pyrazol-5-yl]carbonyl]-2,3-dihydro-8-me-
thyl-3-(1-methylethyl)-4(1H)-quinazolinone,
6-Chloro-1-[[3-chloro-1-(3-chloro-2-pyridinyl)-1H-pyra-
zol-5-yl]carbonyl]-2,3-dihydro-3,8-dimethyl-4(1H)-
quinazolinone,
1-[[3-Bromo-1-(3-chloro-2-pyridinyl)-1H-pyrazol-5-yl]
carbonyl]-6-chloro-2,3-dihydro-3,8-dimethyl-4(1H)-
quinazolinone,
6-Chloro-1-[[1-(3-chloro-2-pyridinyl)-3-(trifluorom-
ethyl)-1H-pyrazol-5-yl]carbonyl]-2,3-dihydro-3,8-
dimethyl-4(1H)-quinazolinone,
6,8-Dichloro-1-[[1-(3-chloro-2-pyridinyl)-3-(trifluorom-
ethyl)-1H-pyrazol-5-yl]carbonyl]-2,3-dihydro-4(1H)-
quinazolinone and
6,8-Dichloro-1-[[3-chloro-1-(3-chloro-2-pyridinyl)-1H-
pyrazol-5-yl]carbonyl]-2,3-dihydro-4(1H)-quinazoli-
none.

This invention also pertains to a composition for controlling an invertebrate pest comprising a biologically effective amount of a compound of Formula I and at least one additional component selected from the group consisting of surfactants, an N-oxide thereof or a suitable salt thereof solid diluents and liquid diluents. This invention also pertains to a composition comprising a biologically effective amount of a compound of Formula I and an effective amount of at least one additional biologically active compound or agent. The preferred compositions of the present invention are those which comprise the above preferred compounds.

This invention also pertains to a method for controlling an invertebrate pest comprising contacting the invertebrate pest or its environment with a biologically effective amount of a compound of Formula I (e.g., as a composition described herein). This invention also relates to such a method wherein the invertebrate pest or its environment is contacted with a biologically effective amount of a compound of Formula I or a composition comprising a compound of Formula I and a biologically effective amount of at least one additional compound or agent for controlling invertebrate pests. The preferred methods of use are those involving the above preferred compounds.

The compounds of Formula I can be prepared by one or more of the following methods and variations as described in Schemes 1-1. The definitions of A, B, J, K, L, $R^3$, $R^4$, $R^5$ and n in the compounds of Formulae I and 2-23 below are as defined above in the Summary of the Invention. Compounds of Formulae Ia-Ic, If, 2a-c, 9a-i and 10a-c are various subsets of the compounds of Formula I, 2, 9 and 10, respectively and all substituents for Formulae Ia-If are as defined above for Formula I.

As shown in Scheme 1, compounds of Formula I can be prepared by the reaction of aryl or heteroaryl amines of Formula 2 with acid chlorides of Formula 3 in the presence of a base to provide a compound of Formula Ia. The reaction can be run neat or in a variety of suitable solvents including tetrahydrofuran, toluene, methylene-chloride and chloroform with optimum temperatures ranging from room temperature to the reflux temperature of the solvent. Typical bases used in the reaction include amines such as triethylamine and pyridine, carbonates such as potassium and sodium carbonate and hydrides such as potassium and sodium hydride. In a subsequent step, compounds of Formula Ia can be converted to compounds of Formula Ib using a variety of standard thio transfer reagents including phosphorus pentasulfide and (2,4-bis(4-methoxyphenyl)-1,3-dithia-2,4-diphosphetane-2,4-disulfide).

Scheme 1

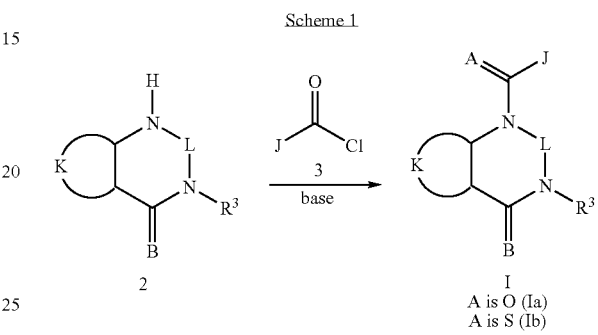

2

I
A is O (Ia)
A is S (Ib)

The preparation of compounds of Formula Ic, i.e. compounds of Formula I wherein K is K-1, is outlined in Scheme 2. Reaction of a quinazolinedione of Formula 2a (wherein L is CO) or a derivative of Formula 2b (wherein L is $C_1$-$C_3$ alkyl optionally substituted with one to three substituents independently selected from $R^{13}$), with an acid chloride of Formula 3 provides a compound of Formula Ic. These procedures can also be applied to prepare compounds of Formula I wherein K is selected from K-2 through K-6.

Scheme 2

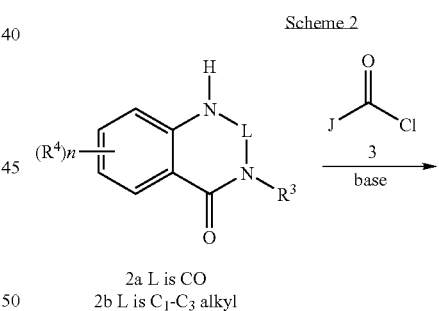

2a L is CO
2b L is $C_1$-$C_3$ alkyl

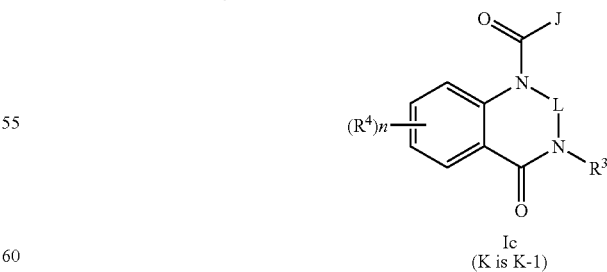

Ic
(K is K-1)

As shown in Scheme 3, compounds Formula 2a can be prepared in two steps from known isatoic anhydrides. In the first step an isatoic anhydride of Formula 4 is reacted directly with an amine of Formula 5 either neat or in a suitable solvent to afford an amide of Formula 6. Treatment of the amide of Formula 6 with phosgene or a phosgene equivalent affords the quinazolinedione of Formula 2a.

Scheme 3

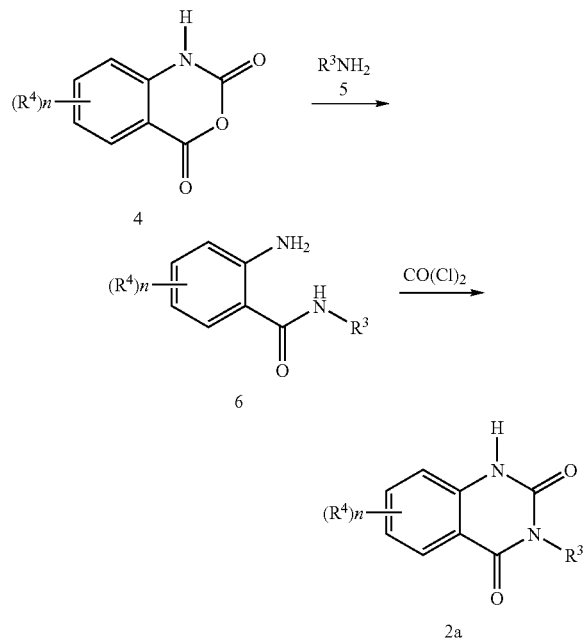

As shown in Scheme 4, compounds of Formula 2b, wherein Rx and Ry are independently H and subsets of $R^{13}$, can be prepared from compounds of Formula 6 by reaction with an aldehyde or ketone generally in the presence of an acid catalyst such as p-toluenesulfonic acid (pTSA). Azeotropic removal of the water as it is formed, or other methods of drying, can be useful in driving the reaction to completion.

Scheme 4

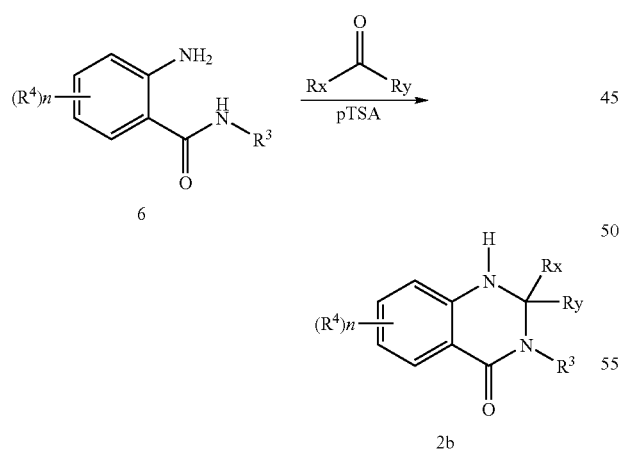

Rx and Ry are each independently H, alkyl or aryl

As shown in Scheme 5, compounds of Formula 2c can be prepared by the Schmidt reaction from tetrahydroquinolinones of Formula 8 and sodium azide (J. Het. Chem. 1971, 8, 231-236). Reaction of a compound of Formula 2c with an acid chloride 3 in the presence of a base such as triethylamine affords a product of Formula 1f.

Scheme 5

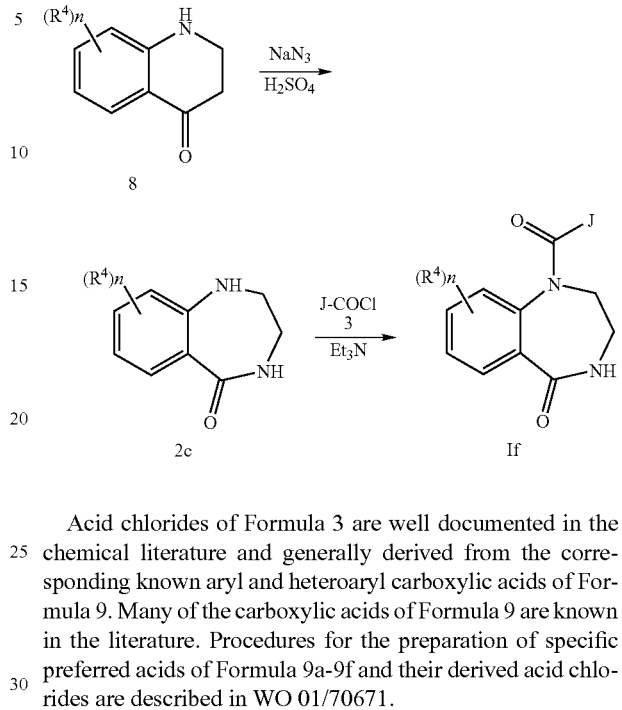

Acid chlorides of Formula 3 are well documented in the chemical literature and generally derived from the corresponding known aryl and heteroaryl carboxylic acids of Formula 9. Many of the carboxylic acids of Formula 9 are known in the literature. Procedures for the preparation of specific preferred acids of Formula 9a-9f and their derived acid chlorides are described in WO 01/70671.

Scheme 6

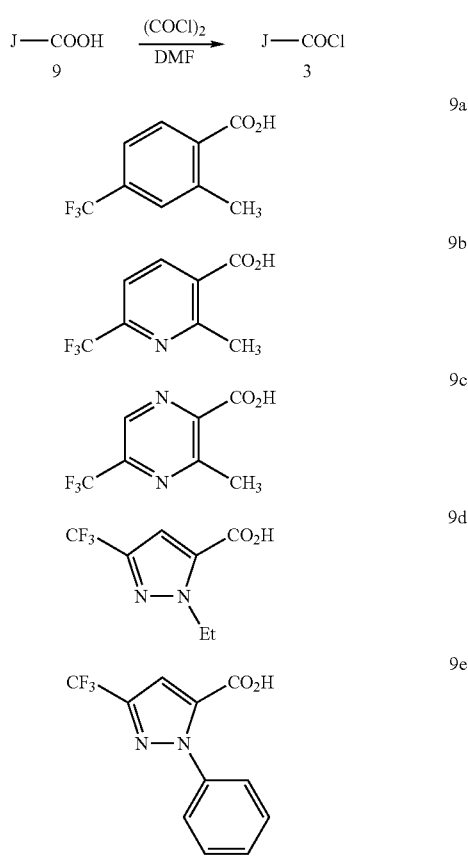

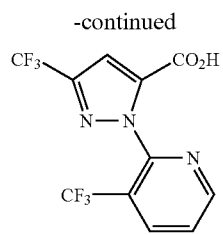

9f

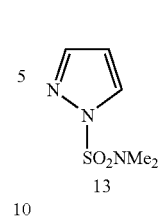

Scheme 8

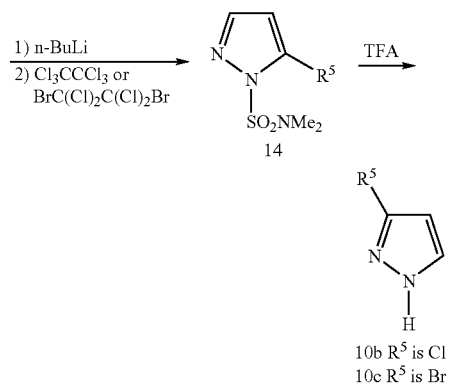

The pyridylpyrazole carboxylic acids of Formula 9g-9i are a specifically preferred set of acids of Formula 9 (Scheme 7). Reaction of a pyrazole of Formula 10 with 2,3-dichloropyridine of Formula 11 affords good yields of the 1-pyridylpyrazole of Formula 12 with good specificity for the desired regiochemistry. Metallation of compounds of Formula 12 with lithium diisopropylamide (LDA) followed by quenching of the lithium salt with carbon dioxide affords the pyrazole acids of Formula 9g-9i. Additional details for the synthesis of Formula 9i are provided in Example 1.

Scheme 7

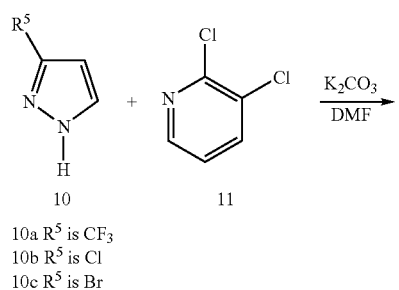

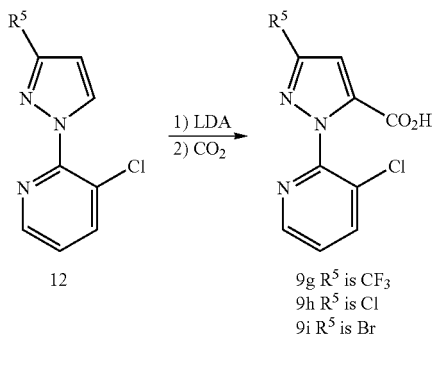

The starting pyrazoles of Formula 10 are known compounds or can be prepared according to known methods. Pyrazole 10a can be prepared by literature procedures (*J. Fluorine Chem.* 1991, 53(1), 61-70). Pyrazoles of Formulae 10b and 10c can also be prepared by literature procedures (*Chem. Ber.* 1966, 99(10), 3350-7). A useful alternative for the preparation of 10b and 10c is depicted in Scheme 8. Metallation of the sulfamoyl pyrazole of Formula 13 with n-butyllithium (n-BuLi) followed by direct halogenation of the anion with either hexachloroethane or 1,2-dibromotetrachloroethane affords the halogenated derivatives of Formula 14. Removal of the sulfamoyl group with trifluoroacetic acid (TFA) at room temperature proceeds cleanly and in good yield to afford the pyrazoles 10b and 10c respectively. Further experimental details for these procedures are described in Example 1.

As an alternative to the method illustrated in Scheme 7, pyrazolecarboxylic acids of Formula 9h and 9i can be prepared by the method outlined in Scheme 9. Reaction of hydrazinopyridine 15 with diethyl maleate affords pyrazolone 16. Chlorination or bromination with phosphorus oxychloride or phosphorus oxybromide affords the halo derivatives of Formula 17. Oxidization of a compound of Formula 17 optionally in the presence of acid to give a pyrazole ester followed by conversion of the ester function to the carboxylic acid provides a compound of Formula 9h or 9i. The oxidizing agent can be hydrogen peroxide, organic peroxides, potassium persulfate, sodium persulfate, ammonium persulfate, potassium monopersulfate (e.g., Oxone®) or potassium permanganate.

Scheme 9

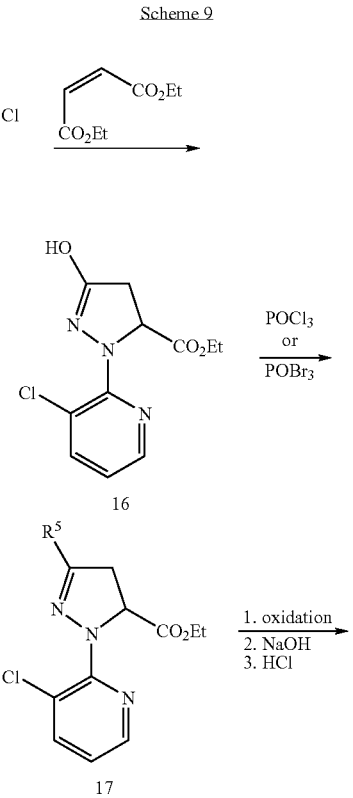

-continued

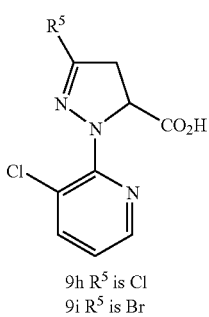

9h R⁵ is Cl
9i R⁵ is Br

As an alternative to the method illustrated in Scheme 7, pyrazolecarboxylic acids of Formula 9g wherein $R^5$ is $CF_3$ can also be prepared by the method outlined in Scheme 10.

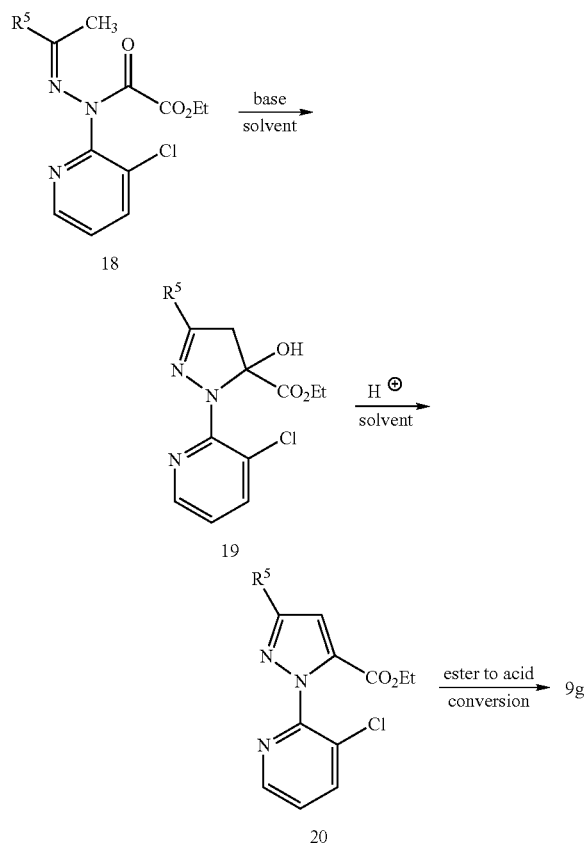

Reaction of a compound of Formula 18 with a suitable base in a suitable organic solvent affords the cyclized product of Formula 19 after neutralization with an acid such as acetic acid. The suitable base can be, for example, sodium hydride, potassium t-butoxide, dimsyl sodium ($CH_3S(O)CH_2^{\ominus}Na^{\oplus}$), alkali metal (such as lithium, sodium or potassium) carbonates or hydroxides, tetraalkyl (such as methyl, ethyl or butyl)ammonium fluorides or hydroxides, or 2-tert-butylimino-2-diethylamino-1,3-dimethyl-perhydro-1,3,2-diazaphosphonine. The suitable organic solvent can be, for example, acetone, acetonitrile, tetrahydrofuran, dichloromethane, dimethylsulfoxide, or N,N-dimethylformamide.

Dehydration of the compound of Formula 19 to give the compound of Formula 20, followed by converting the carboxylic ester function to carboxylic acid, affords the acids of Formula 9g. The dehydration is effected by treatment with a catalytic amount of a suitable acid such as sulfuric acid.

Compounds of Formula 18 can be prepared by the method outlined in Scheme 11.

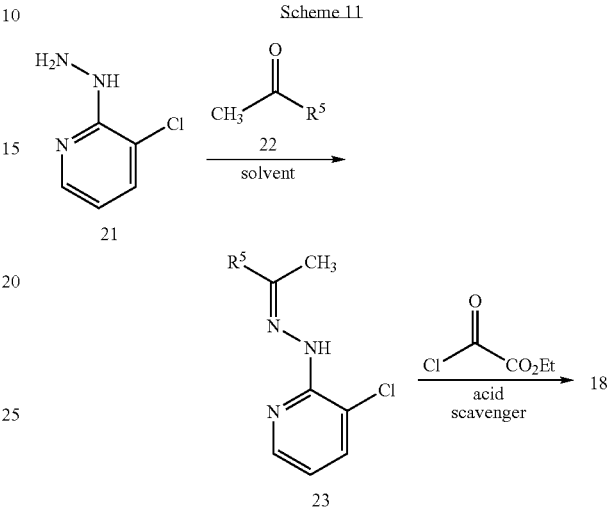

wherein $R^5$ is $CF_3$.

Treatment of a hydrazine compound of Formula 21 with a ketone of Formula 22 in a solvent such as water, methanol or acetic acid gives the hydrazone of Formula 23. Reaction of the hydrazone of Formula 23 with ethyl oxalyl chloride in a suitable organic solvent such as dichloromethane or tetrahydrofuran in the presence of an acid scavenger such as triethylamine provides the compound of Formula 18. Hydrazine compounds of Formula 21 can be prepared by standard methods, such as by contacting the corresponding halo compound of Formula 11 with hydrazine.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I. One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s is singlet, d is doublet, t is triplet, q is quartet, m is multiplet, dd is doublet of doublets, dt is doublet of triplets, br s is broad singlet.

EXAMPLE 1

6-Bromo-1-[[3-bromo-1-(3-chloro-2-pyridinyl)-1H-pyrazol-5-yl]carbonyl]-8-methyl-3-(1-methylethyl)-2,4(1H,3H)-quinazolinedione Step A: Preparation of 3-bromo-N,N-dimethyl-1H-pyrazole-1-sulfonamide To a solution of N-dimethylsulfamoylpyrazole (44.0 g, 0.251 mol) in dry tetrahydrofuran (500 mL) at −78° C. was added dropwise a solution of n-butyllithium (2.5 M in hexane, 105.5 mL, 0.264 mol) while maintaining the temperature below −60° C. A thick solid formed during the addition. Upon completion of the addition the reaction mixture was maintained for an additional 15 minutes, after which time a solution of 1,2-dibromo-tetrachloroethane (90 g, 0.276 mol) in tetrahydrofuran (150 mL) was added dropwise while maintaining the temperature below −70° C. The reaction mixture turned a clear orange; stirring was continued for an additional 15 minutes. The −78° C. bath was removed and the reaction was quenched with water (600 mL). The reaction mixture was extracted with dichloromethane (4×), and the organic extracts were dried over magnesium sulfate and concentrated. The crude product was further purified by chromatography on silica gel using dichloromethane/hexane (50:50) as eluent to afford the title product as a clear colorless oil (57.04 g).

$^1$H NMR (CDCl$_3$) δ 3.07 (d,6H), 6.44 (m, 1H), 7.62 (m, 1H).

Step B: Preparation of 3-bromopyrazole

To trifluoroacetic acid (70 mL) was slowly added the bromopyrazole product (57.04 g) from Step A. The reaction mixture was stirred at room temperature for 30 minutes and then concentrated at reduced pressure. The residue was taken up in hexane, insoluble solids were filtered off, and the hexane was evaporated to afford the crude product as an oil. The crude product was further purified by chromatography on silica gel using ethyl acetate/dichloromethane (10:90) as eluent to afford an oil. The oil was taken up in dichloromethane, neutralized with aqueous sodium bicarbonate solution, extracted with dichloromethane (3×), dried over magnesium sulfate and concentrated to afford the title product as a white solid (25.9 g), m.p. 61-64° C.

$^1$H NMR (CDCl$_3$) δ 6.37 (d,1H), 7.59 (d,1H), 12.4 (br s,1H).

Step C: Preparation of 2-(3-bromo-1H-pyrazol-1-yl)-3-chloropyridine

To a mixture of 2,3-dichloropyridine (27.4 g, 185 mmol) and 3-bromopyrazole (25.4 g, 176 mmol) in dry N,N-dimethylformamide (88 mL) was added potassium carbonate (48.6 g, 352 mmol), and the reaction mixture was heated to 125° C. for 18 hours. The reaction mixture was cooled to room temperature and poured into ice water (800 mL). A precipitate formed. The precipitated solids were stirred for 1.5 hrs, filtered and washed with water (2×100 mL). The solid filter cake was taken up in dichloromethane and washed sequentially with water, 1N hydrochloric acid, saturated aqueous sodium bicarbonate solution, and brine. The organic extracts were then dried over magnesium sulfate and concentrated to afford 39.9 g of a pink solid. The crude solid was suspended in hexane and stirred vigorously for 1 hour. The solids were filtered, washed with hexane and dried to afford the title product as an off-white powder (30.4 g) determined to be >94% pure by NMR. This material was used without further purification in Step D.

1H NMR (CDCl$_3$)H), δ 6.52 (s,1H), 7.30 (dd,1H), 8.05 (s,1H), 8.43 (d,1H).

Step D: Preparation of 3-bromo-1-(3-chloro-2-pyridinyl)-1H-pyrazole-5-carboxylic acid To a solution of the pyrazole product from Step C (30.4 g, 118 mmol) in dry tetrahydrofuran (250 mL) at −76° C. was added dropwise a solution of lithium diisopropylamide (118 mmol) in tetrahydrofuran at such a rate as to maintain the temperature below −71° C. The reaction mixture was stirred for 15 minutes at −76° C., and carbon dioxide was then bubbled through for 10 minutes, causing warming to −57° C. The reaction mixture was warmed to −20° C. and quenched with water. The reaction mixture was concentrated and then taken up in water (1 L) and ether (500 mL), and then aqueous sodium hydroxide solution (1 N, 20 mL) was added. The aqueous extracts were washed with ether and acidified with hydrochloric acid. The precipitated solids were filtered, washed with water and dried to afford the title product as a tan solid (27.7 g). (Product from another run following similar procedure melted at 200-201° C.)

$^1$H NMR (DMSO-d$_6$) δ 7.25 (s, 1H), 7.68 (dd, 1H), 8.24 (d, 1H), 8.56 (d, 1H).

Step E: Preparation of 6-bromo-8-methyl-2H-3,1-benzoxazine-2,4(1H)-dione

To a solution of 8-methyl-2H-3,1-benzoxazine-2,4(1H)-dione, (10.0 g, 56.5 mmol) and potassium iodide (0.36 g, 1.8 mmol) in chlorosulfonic acid (12 mL) was added bromine (4.6 g, 28.7 mmol). and the reaction was stirred overnight at room temperature. The reaction was then slowly poured onto ice water and neutralized with sodium bicarbonate powder to a pH of 7. The solids were filtered, rinsed with water and to afford the desired intermediate as a white solid (11.4 g).

$^1$H NMR (DMSO) δ 2.34 (s,3H), 7.76 (m,3H), 7.85 (m,1H), 11.21 (s,1H).

Step F: Preparation of 2-amino-5-bromo-3-methyl-N-(1-methylethyl)benzamide

To a suspension of the benzoxazinedione of Step E, (4.0 g, 15.56 mmol) in pyridine (20 mL) was added isopropylamine (1.2 g, 20.23 mmol) and the reaction was heated to reflux for 2 hours. The reaction was then cooled, concentrated from toluene on a rotary evaporator and then dried under vacuum to afford a solid (5.01 g).

$^1$H NMR (DMSO) δ 1.29 (d,6H), 2.15 (s,3H), 4.25 (m,1H), 5.75 (m,1H), 7.24 (m,1H) 7.27 (m,1H).

Step G: Preparation of 6-bromo-8-methyl-3-(1-methylethyl)-2,4(1H,3H)-quinazolinedione To a solution of the anthranilamide of Step F, (1.11 g, 4.1 mmol) in dioxane (20 mL) was added a 2.0 M solution of phosgene in toluene (2.3 mL, 4.6 mmol). The reaction was stirred at room temperature for 1 hour then heated to reflux for 4 hours and cooled to room temperature. The white solids were filtered and dried to afford the title compound (0.89 g).

$^1$H NMR (DMSO) δ 1.43 (d,6H), 2.34 (s,3H), 5.12 (m,1H), 7.67 (s,1H), 7.85 (s,1H).

Step H: Preparation of 6-bromo-1-[[3-bromo-1-(3-chloro-2-pyridinyl)-1H-pyrazol-5-yl]carbonyl]-8-methyl-3-(1-methylethyl)-2,4(1H,3H)-quinazolinedione To a solution of the quinazolinedione of Step G (245 mg, 0.825 mmol) in dimethylformamide (5 mL) was added sodium hydride (60% oil dispersion, 36 mg, 0.90 mmol) and the reaction was allowed to stir at room temperature. In a separate reaction flask containing a solution of the pyrazole acid of Step D (500 mg, 1.65 mmol) in dichloromethane (10 mL) was added oxalyl chloride (0.17 mL, 1.95 mmol) and one drop of DMF. This mixture was stirred for 2 hours, then concentrated and placed under vacuum. The acid chloride was divided into two equal portions. One of these portions was taken up in 5 mL of DMF and added to the quinazolinedione/NaH reaction mixture and the resulting mixture was stirred at room temperature for 3 hours. The reaction was partitioned between ethyl acetate and water, washed twice with water, then with brine and dried over sodium sulfate. The crude product was purified by chromatography on silica gel with 99:1 chloroform/acetone as eluent to afford the title compound, a compound of the present invention.

$^1$H NMR (CDCl$_3$) δ 1.47 (d,6H), 2.17 (s,3H), 5.08 (m,1H), 7.12 (s,1H), 7.39 (dd,1H), 7.54 (d,1H), 7.91 (dd,1H), 8.17 (d,1H), 8.34 (dd,1H).

EXAMPLE 2

Preparation of 1-[[3-Bromo-1-(3-chloro-2-pyridinyl)-1H-pyrazol-5-yl]carbonyl]-2,3-dihydro-8-methyl-3-(1-methylethyl)-4(1H)-quinazolinone Step A: Preparation of 2,3-dihydro-8-methyl-3-(1-methylethyl)-4(1H)-quinazolinone To a solution of 2-amino-3-methyl-N-(1-methylethyl)benzamide (0.5 g, 2.6 mmol) in ethanol (10 mL) was added paraformaldehyde (78 mg, 2.6 mmol) and p-toluenesulfonic acid (18 mg, 95 μmol) and the mixture was heated at reflux until it became clear (approximately 4 hours). The solvent was removed under reduced pressure to give the title compound (95% pure) which was used without further purification.

$^1$H NMR (CDCl$_3$) δ 7.9-7.8 (d,1H), 7.2-7.1 (d,1H), 6.83 (t,1H), 4.97 (m,1H), 4.57 (s,2H), 2.17 (s,3H), 1.22 (d,6H).

Step B: Preparation of 1-[[3-bromo-1-(3-chloro-2-pyridinyl)-1H-pyrazol-5-yl]carbonyl]-2,3-dihydro-8-methyl-3-(1-methylethyl)-4(1H)-quinazolinone To a solution of 3-bromo-1-(3-chloro-2-pyridinyl)-1H-pyrazole-5-carboxylic acid (787 mg, 2.45 mmol) (i.e. the product of Example 1, Step D) in dichloromethane (10 mL) was added dimethylformamide (20 μL) and oxalyl chloride (235 μL). The mixture was stirred for 1 hour, at which point it had become clear. After removing volatiles under reduced pressure, the residue was dissolved in dichloromethane (5 mL) and one half of the solution was added to a mixture of the product of Step A (0.25 g, 1.2 mmol) and pyridine (148 μL, 1.8 mmol) in methylene chloride (10 mL). After stirring at ambient temperature overnight, 1,5,7-triazabicyclo[4.4.0]dec-5-ene bound to polystyrene crosslinked with 2% DVB (1 g) (Fluka Chemie AG catalog number 90603) was added and the mixture was stirred for an additional 15 minutes. The mixture was then filtered and concentrated under reduced pressure. The resulting residue was purified by chromatography on silica gel to give the title compound, a compound of the invention, as a white solid (0.18 g).

$^1$H NMR (CDCl$_3$) δ 8.3 (m,1H), 7.9-7.8 (m,2H), 7.4-7.3 (m,3H), 6.0-5.9 (s,1H), 5.9 (d,1H), 5.0-4.8 (m,1H), 4.4-4.3 (d,1H), 2.10 (s,3H), 1.3-1.1 (m,6H).

The following Example 3 illustrates an alternative preparation of 3-bromo-1-(3-chloro-2-pyridinyl)-1H-pyrazole-5-carboxylic acid, which can be used to prepare, for example, 6-bromo-1-[[3-bromo-1-(3-chloro-2-pyridinyl)-1H-pyrazol-5-yl]carbonyl]-8-methyl-3-(1-methylethyl)-2,4(1H,3H)-quinazolinedione and 1-[[3-bromo-1-(3-chloro-2-pyridinyl)-1H-pyrazol-5-yl]carbonyl]-2,3-dihydro-8-methyl-3-(1-methylethyl)-4(1H)-quinazolinone, by further steps illustrated in Example 1 and 2.

EXAMPLE 3

Preparation of 3-Bromo-1-(3-chloro-2-pyridinyl)-1H-pyrazole-5-carboxylic acid

Step A: Preparation of Ethyl 2-(3-Chloro-2-pyridinyl)-5-oxo-3-pyrazolidinecarboxylate A 2-L four-necked flask equipped with a mechanical stirrer, thermometer, addition funnel, reflux condenser, and nitrogen inlet was charged with absolute ethanol (250 mL) and an ethanolic solution of sodium ethoxide (21%, 190 mL, 0.504 mol). The mixture was heated to reflux at about 83° C. It was then treated with 3-chloro-2(1H)-pyridinone hydrazone (68.0 g, 0.474 mol). The mixture was re-heated to reflux over a period of 5 minutes. The yellow slurry was then treated dropwise with diethyl maleate (88.0 mL, 0.544 mol) over a period of 5 minutes. The reflux rate increased markedly during the addition. By the end of the addition all of the starting material had dissolved. The resulting orange-red solution was held at reflux for 10 minutes. After being cooled to 65° C., the reaction mixture was treated with glacial acetic acid (50.0 mL, 0.873 mol). A precipitate formed. The mixture was diluted with water (650 mL), causing the precipitate to dissolve. The orange solution was cooled in an ice bath. Product began to precipitate at 28° C. The slurry was held at about 2° C. for 2 hours. The product was isolated via filtration, washed with aqueous ethanol (40%, 3×50 mL), and then air-dried on the filter for about 1 hour. The title product compound was obtained as a highly crystalline, light orange powder (70.3 g, 55% yield). No significant impurities were observed by $^1$H NMR.

$^1$H NMR (DMSO-d$_6$) δ 1.22 (t, 3H), 2.35 (d, 1H), 2.91 (dd, 1H), 4.20 (q, 2H), 4.84 (d, 1H), 7.20 (dd, 1H), 7.92 (d, 1H), 8.27 (d, 1H), 10.18 (s, 1H).

Step B: Preparation of Ethyl 3-Bromo-1-(3-chloro-2-pyridinyl)-4,5-dihydro-1H-pyrazole-5-carboxylate A 1-L four-necked flask equipped with a mechanical stirrer, thermometer, reflux condenser, and nitrogen inlet was charged with acetonitrile (400 mL), ethyl 2-(3-chloro-2-pyridinyl)-5-oxo-3-pyrazolidinecarboxylate (i.e. the product of Step A) (50.0 g, 0.185 mol) and phosphorus oxybromide (34.0 g, 0.119 mol). The orange slurry was heated to reflux at 83° C. over a period of 20 minutes. The resulting turbid, orange solution was held at reflux for 75 minutes, at which time a dense, tan, crystalline precipitate had formed. The reflux condenser was replaced with a distillation head, and a cloudy, colorless distillate (300 mL) was collected. A second 1-L four-necked flask equipped with a mechanical stirrer was charged with sodium bicarbonate (45 g, 0.54 mol) and water (200 mL). The concentrated reaction mixture was added to the sodium bicarbonate slurry over a period of 5 minutes. The resulting two-phase mixture was stirred vigorously for 5 minutes, at which time gas evolution had ceased. The mixture was diluted with dichloromethane (200 mL) and then was stirred for 75 minutes. The mixture was treated with 5 g of Celite® 545 diatomaceous filter aid and then filtered to remove a brown, tarry substance. The filtrate was transferred to a separatory funnel. The brown organic layer (400 mL) was separated and then was treated with magnesium sulfate (15 g) and Darco® G60 activated charcoal (2.0 g). The resulting slurry was stirred magnetically for 15 minutes and then filtered to remove the magnesium sulfate and charcoal. The green filtrate was treated with silica gel (3 g) and stirred for several minutes. The deep blue-green silica gel was removed by filtration, and the filtrate was concentrated on a rotary evaporator. The product consisted of a light amber oil (58.6 g, 95% yield), which crystallized upon standing. The only appreciable impurity observed by $^1$H NMR was 0.3% acetonitrile.

$^1$H NMR (DMSO-$d_6$) δ 1.15 (t, 3H), 3.29 (dd, 1H), 3.60 (dd, 1H), 4.11 (q, 2H), 5.20 (dd, 1H), 6.99 (dd, 1H), 7.84 (d, 1H), 8.12 (d, 1H).

Step C: Preparation of Ethyl 3-Bromo-1-(3-chloro-2-pyridinyl)-1H-pyrazole-5-carboxylate A 1-L four-necked flask equipped with a mechanical stirrer, thermometer, reflux condenser, and nitrogen inlet was charged with ethyl 3-bromo-1-(3-chloro-2-pyridinyl)-4,5-dihydro-1H-pyrazole-5-carboxylate (i.e. the product of Step B) (40.2 g, 0.121 mol), acetonitrile (300 mL) and sulfuric acid (98%, 13.0 mL, 0.245 mol). The mixture self-heated from 22 to 36° C. upon adding the sulfuric acid. After being stirred for several minutes, the mixture was treated with potassium persulfate (48.0 g, 0.178 mol). The slurry was heated to reflux at 84° C. for 2 hours. The resulting orange slurry while still warm (50-65° C.) was filtered to remove a white precipitate. The filter cake was washed with acetonitrile (2×50 mL). The filtrate was concentrated to about 200 mL on a rotary evaporator. A second 1-L four-necked flask equipped with a mechanical stirrer was charged with water (400 mL). The concentrated reaction mass was added to the water over a period of about 5 minutes. The product was isolated via filtration, washed sequentially with aqueous acetonitrile (20%, 100 mL) and water (75 mL), and was then air-dried on the filter for 1 hour. The product consisted of a crystalline, orange powder (36.6 g, 90% yield). The only appreciable impurities observed by $^1$H NMR were about 1% of an unknown and 0.5% acetonitrile.

$^1$H NMR (DMSO-$d_6$) δ 1.09 (t, 3H), 4.16 (q, 2H), 7.35 (s, 1H), 7.72 (dd, 1H), 8.39 (d, 1H), 8.59 (d, 1H).

Step D: Preparation of 3-Bromo-1-(3-chloro-2-pyridinyl)-1H-pyrazole-5-carboxylic acid A 300-mL four-necked flask equipped with a mechanical stirrer, thermometer, and nitrogen inlet was charged with ethyl 3-bromo-1-(3-chloro-2-pyridinyl)-1H-pyrazole-5-carboxylate (i.e. the product of Step C) (98.5% pure, 25.0 g, 0.0756 mol), methanol (75 mL), water (50 mL), and sodium hydroxide pellets (3.30 g, 0.0825 mol). Upon adding the sodium hydroxide the mixture self-heated from 29 to 34° C. and the starting material began to dissolve. After being stirred for 90 minutes under ambient conditions, all of the starting material had dissolved. The resulting dark orange solution was concentrated to about 90 mL on a rotary evaporator. The concentrated reaction mixture was then diluted with water (160 mL). The aqueous solution was extracted with ether (100 mL). Then the aqueous layer was transferred to a 500-mL Erlenmeyer flask equipped with a magnetic stirrer. The solution was treated dropwise with concentrated hydrochloric acid (8.50 g, 0.0839 mol) over a period of about 10 minutes. The product was isolated via filtration, reslurried with water (2×40 mL), cover washed once with water (25 mL), and then air-dried on the filter for 2 hours. The product consisted of a crystalline, tan powder (20.9 g, 91% yield). The only appreciable impurities observed by $^1$H NMR were about 0.8% of an unknown and 0.7% ether.

$^1$H NMR (DMSO-$d_6$) δ 7.25 (s, 1H), 13.95 (br s, 1H), 8.56 (d, 1H), 8.25 (d, 1H), 7.68 (dd, 1H).

By the procedures described herein together with methods known in the art, the following compounds of Tables 1 to 10 can be prepared. The following abbreviations are used in the Tables which follow: t is tertiary, s is secondary, n is normal, i is iso, c is cyclo, Me is methyl, Et is ethyl, Pr is propyl, i-Pr is isopropyl, Bu is butyl and t-Bu is tertiary butyl.

TABLE 1

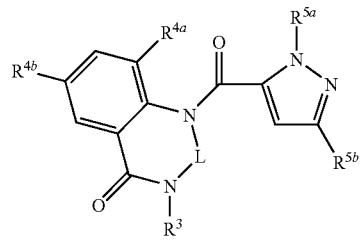

| $R^3$ | $R^{4a}$ | $R^{4b}$ | $R^{5a}$ | $R^{5b}$ |
|---|---|---|---|---|
| L is C=O | | | | |
| H | Me | H | Me | $CF_3$ |
| H | Cl | H | Me | $CF_3$ |
| H | Me | Cl | Me | $CF_3$ |
| H | Cl | Cl | Me | $CF_3$ |
| H | Me | Br | Me | $CF_3$ |
| H | Cl | Br | Me | $CF_3$ |
| i-Pr | Me | H | Me | $CF_3$ |
| i-Pr | Cl | H | Me | $CF_3$ |
| i-Pr | Me | Cl | Me | $CF_3$ |
| i-Pr | Cl | Cl | Me | $CF_3$ |
| i-Pr | Me | Br | Me | $CF_3$ |
| i-Pr | Cl | Br | Me | $CF_3$ |
| t-Bu | Me | H | Me | $CF_3$ |
| t-Bu | Cl | H | Me | $CF_3$ |
| t-Bu | Me | Cl | Me | $CF_3$ |
| t-Bu | Cl | Cl | Me | $CF_3$ |
| t-Bu | Me | Br | Me | $CF_3$ |
| t-Bu | Cl | Br | Me | $CF_3$ |
| Et | Me | H | Me | $CF_3$ |
| Et | Cl | H | Me | $CF_3$ |
| Et | Me | Cl | Me | $CF_3$ |
| Et | Cl | Cl | Me | $CF_3$ |
| Et | Me | Br | Me | $CF_3$ |
| Et | Cl | Br | Me | $CF_3$ |
| Me | Me | H | Me | $CF_3$ |
| Me | Cl | H | Me | $CF_3$ |
| Me | Me | Cl | Me | $CF_3$ |
| Me | Cl | Cl | Me | $CF_3$ |
| Me | Me | Br | Me | $CF_3$ |
| Me | Cl | Br | Me | $CF_3$ |
| H | Me | H | Me | $OCF_3$ |
| H | Cl | H | Me | $OCF_3$ |
| H | Me | Cl | Me | $OCF_3$ |
| H | Cl | Cl | Me | $OCF_3$ |
| H | Me | Br | Me | $OCF_3$ |
| H | Cl | Br | Me | $OCF_3$ |
| i-Pr | Me | H | Me | $OCF_3$ |
| i-Pr | Cl | H | Me | $OCF_3$ |
| i-Pr | Me | Cl | Me | $OCF_3$ |
| i-Pr | Cl | Cl | Me | $OCF_3$ |
| i-Pr | Me | Br | Me | $OCF_3$ |
| i-Pr | Cl | Br | Me | $OCF_3$ |
| t-Bu | Me | H | Me | $OCF_3$ |
| t-Bu | Cl | H | Me | $OCF_3$ |
| t-Bu | Me | Cl | Me | $OCF_3$ |
| t-Bu | Cl | Cl | Me | $OCF_3$ |
| t-Bu | Me | Br | Me | $OCF_3$ |

TABLE 1-continued

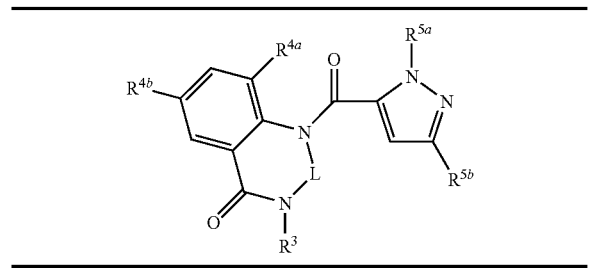

| R³ | R⁴ᵃ | R⁴ᵇ | R⁵ᵃ | R⁵ᵇ |
|---|---|---|---|---|
| t-Bu | Cl | Br | Me | OCF₃ |
| Et | Me | H | Me | OCF₃ |
| Et | Cl | H | Me | OCF₃ |
| Et | Me | Cl | Me | OCF₃ |
| Et | Cl | Cl | Me | OCF₃ |
| Et | Me | Br | Me | OCF₃ |
| Et | Cl | Br | Me | OCF₃ |
| Me | Me | H | Me | OCF₃ |
| Me | Cl | H | Me | OCF₃ |
| Me | Me | Cl | Me | OCF₃ |
| Me | Cl | Cl | Me | OCF₃ |
| Me | Me | Br | Me | OCF₃ |
| Me | Cl | Br | Me | OCF₃ |
| H | Me | H | Me | CF(CF₃)₂ |
| H | Cl | H | Me | CF(CF₃)₂ |
| H | Me | Cl | Me | CF(CF₃)₂ |
| H | Cl | Cl | Me | CF(CF₃)₂ |
| H | Me | Br | Me | CF(CF₃)₂ |
| H | Cl | Br | Me | CF(CF₃)₂ |
| i-Pr | Me | H | Me | CF(CF₃)₂ |
| i-Pr | Cl | H | Me | CF(CF₃)₂ |
| i-Pr | Me | Cl | Me | CF(CF₃)₂ |
| i-Pr | Cl | Cl | Me | CF(CF₃)₂ |
| i-Pr | Me | Br | Me | CF(CF₃)₂ |
| i-Pr | Cl | Br | Me | CF(CF₃)₂ |
| t-Bu | Me | H | Me | CF(CF₃)₂ |
| t-Bu | Cl | H | Me | CF(CF₃)₂ |
| t-Bu | Me | Cl | Me | CF(CF₃)₂ |
| t-Bu | Cl | Cl | Me | CF(CF₃)₂ |
| t-Bu | Me | Br | Me | CF(CF₃)₂ |
| t-Bu | Cl | Br | Me | CF(CF₃)₂ |
| Et | Me | H | Me | CF(CF₃)₂ |
| Et | Cl | H | Me | CF(CF₃)₂ |
| Et | Me | Cl | Me | CF(CF₃)₂ |
| Et | Cl | Cl | Me | CF(CF₃)₂ |
| Et | Me | Br | Me | CF(CF₃)₂ |
| Et | Cl | Br | Me | CF(CF₃)₂ |
| Me | Me | H | Me | CF(CF₃)₂ |
| Me | Cl | H | Me | CF(CF₃)₂ |
| Me | Me | Cl | Me | CF(CF₃)₂ |
| Me | Cl | Cl | Me | CF(CF₃)₂ |
| Me | Me | Br | Me | CF(CF₃)₂ |
| Me | Cl | Br | Me | CF(CF₃)₂ |
| L is CH₂ | | | | |
| H | Me | H | Me | CF₃ |
| H | Cl | H | Me | CF₃ |
| H | Me | Cl | Me | CF₃ |
| H | Cl | Cl | Me | CF₃ |
| H | Me | Br | Me | CF₃ |
| H | Cl | Br | Me | CF₃ |
| i-Pr | Me | H | Me | CF₃ |
| i-Pr | Cl | H | Me | CF₃ |
| i-Pr | Me | Cl | Me | CF₃ |
| i-Pr | Cl | Cl | Me | CF₃ |
| i-Pr | Me | Br | Me | CF₃ |
| i-Pr | Cl | Br | Me | CF₃ |
| t-Bu | Me | H | Me | CF₃ |
| t-Bu | Cl | H | Me | CF₃ |
| t-Bu | Me | Cl | Me | CF₃ |
| t-Bu | Cl | Cl | Me | CF₃ |
| t-Bu | Me | Br | Me | CF₃ |
| t-Bu | Cl | Br | Me | CF₃ |
| Et | Me | H | Me | CF₃ |
| Et | Cl | H | Me | CF₃ |
| Et | Me | Cl | Me | CF₃ |
| Et | Cl | Cl | Me | CF₃ |
| Et | Me | Br | Me | CF₃ |
| Et | Cl | Br | Me | CF₃ |
| Me | Me | H | Me | CF₃ |
| Me | Cl | H | Me | CF₃ |
| Me | Me | Cl | Me | CF₃ |
| Me | Cl | Cl | Me | CF₃ |
| Me | Me | Br | Me | CF₃ |
| Me | Cl | Br | Me | CF₃ |
| H | Me | H | Me | OCF₃ |
| H | Cl | H | Me | OCF₃ |
| H | Me | Cl | Me | OCF₃ |
| H | Cl | Cl | Me | OCF₃ |
| H | Me | Br | Me | OCF₃ |
| H | Cl | Br | Me | OCF₃ |
| i-Pr | Me | H | Me | OCF₃ |
| i-Pr | Cl | H | Me | OCF₃ |
| i-Pr | Me | Cl | Me | OCF₃ |
| i-Pr | Cl | Cl | Me | OCF₃ |
| i-Pr | Me | Br | Me | OCF₃ |
| i-Pr | Cl | Br | Me | OCF₃ |
| t-Bu | Me | H | Me | OCF₃ |
| t-Bu | Cl | H | Me | OCF₃ |
| t-Bu | Me | Cl | Me | OCF₃ |
| t-Bu | Cl | Cl | Me | OCF₃ |
| t-Bu | Me | Br | Me | OCF₃ |
| t-Bu | Cl | Br | Me | OCF₃ |
| Et | Me | H | Me | OCF₃ |
| Et | Cl | H | Me | OCF₃ |
| Et | Me | Cl | Me | OCF₃ |
| Et | Cl | Cl | Me | OCF₃ |
| Et | Me | Br | Me | OCF₃ |
| Et | Cl | Br | Me | OCF₃ |
| Me | Me | H | Me | OCF₃ |
| Me | Cl | H | Me | OCF₃ |
| Me | Me | Cl | Me | OCF₃ |
| Me | Cl | Cl | Me | OCF₃ |
| Me | Me | Br | Me | OCF₃ |
| Me | Cl | Br | Me | OCF₃ |
| H | Me | H | Me | CF(CF₃)₂ |
| H | Cl | H | Me | CF(CF₃)₂ |
| H | Me | Cl | Me | CF(CF₃)₂ |
| H | Cl | Cl | Me | CF(CF₃)₂ |
| H | Me | Br | Me | CF(CF₃)₂ |
| H | Cl | Br | Me | CF(CF₃)₂ |
| i-Pr | Me | H | Me | CF(CF₃)₂ |
| i-Pr | Cl | H | Me | CF(CF₃)₂ |
| i-Pr | Me | Cl | Me | CF(CF₃)₂ |
| i-Pr | Cl | Cl | Me | CF(CF₃)₂ |
| i-Pr | Me | Br | Me | CF(CF₃)₂ |
| i-Pr | Cl | Br | Me | CF(CF₃)₂ |
| t-Bu | Me | H | Me | CF(CF₃)₂ |
| t-Bu | Cl | H | Me | CF(CF₃)₂ |
| t-Bu | Me | Cl | Me | CF(CF₃)₂ |
| t-Bu | Cl | Cl | Me | CF(CF₃)₂ |
| t-Bu | Me | Br | Me | CF(CF₃)₂ |
| t-Bu | Cl | Br | Me | CF(CF₃)₂ |
| Et | Me | H | Me | CF(CF₃)₂ |
| Et | Cl | H | Me | CF(CF₃)₂ |
| Et | Me | Cl | Me | CF(CF₃)₂ |
| Et | Cl | Cl | Me | CF(CF₃)₂ |
| Et | Me | Br | Me | CF(CF₃)₂ |

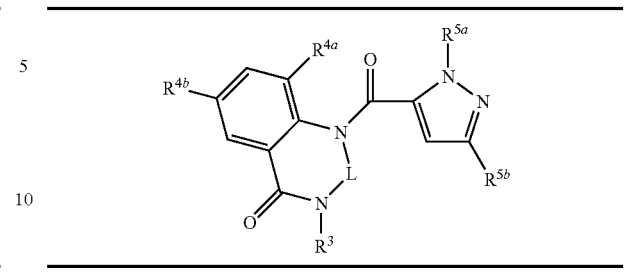

TABLE 1-continued

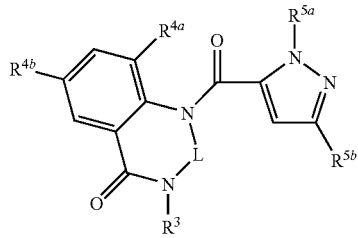

| R³ | R⁴ᵃ | R⁴ᵇ | R⁵ᵃ | R⁵ᵇ |
|---|---|---|---|---|
| Et | Cl | Br | Me | CF(CF₃)₂ |
| Me | Me | H | Me | CF(CF₃)₂ |
| Me | Cl | H | Me | CF(CF₃)₂ |
| Me | Me | Cl | Me | CF(CF₃)₂ |
| Me | Cl | Cl | Me | CF(CF₃)₂ |
| Me | Me | Br | Me | CF(CF₃)₂ |
| Me | Cl | Br | Me | CF(CF₃)₂ |
| L is CH₂CH₂ | | | | |
| H | Me | H | Me | CF₃ |
| H | Cl | H | Me | CF₃ |
| H | Me | Cl | Me | CF₃ |
| H | Cl | Cl | Me | CF₃ |
| H | Me | Br | Me | CF₃ |
| H | Cl | Br | Me | CF₃ |
| i-Pr | Me | H | Me | CF₃ |
| i-Pr | Cl | H | Me | CF₃ |
| i-Pr | Me | Cl | Me | CF₃ |
| i-Pr | Cl | Cl | Me | CF₃ |
| i-Pr | Me | Br | Me | CF₃ |
| i-Pr | Cl | Br | Me | CF₃ |
| t-Bu | Me | H | Me | CF₃ |
| t-Bu | Cl | H | Me | CF₃ |
| t-Bu | Me | Cl | Me | CF₃ |
| t-Bu | Cl | Cl | Me | CF₃ |
| t-Bu | Me | Br | Me | CF₃ |
| t-Bu | Cl | Br | Me | CF₃ |
| Et | Me | H | Me | CF₃ |
| Et | Cl | H | Me | CF₃ |
| Et | Me | Cl | Me | CF₃ |
| Et | Cl | Cl | Me | CF₃ |
| Et | Me | Br | Me | CF₃ |
| Et | Cl | Br | Me | CF₃ |
| Me | Me | H | Me | CF₃ |
| Me | Cl | H | Me | CF₃ |
| Me | Me | Cl | Me | CF₃ |
| Me | Cl | Cl | Me | CF₃ |
| Me | Me | Br | Me | CF₃ |
| Me | Cl | Br | Me | CF₃ |
| H | Me | H | Me | OCF₃ |
| H | Cl | H | Me | OCF₃ |
| H | Me | Cl | Me | OCF₃ |
| H | Cl | Cl | Me | OCF₃ |
| H | Me | Br | Me | OCF₃ |
| H | Cl | Br | Me | OCF₃ |
| i-Pr | Me | H | Me | OCF₃ |
| i-Pr | Cl | H | Me | OCF₃ |
| i-Pr | Me | Cl | Me | OCF₃ |
| i-Pr | Cl | Cl | Me | OCF₃ |
| i-Pr | Me | Br | Me | OCF₃ |
| i-Pr | Cl | Br | Me | OCF₃ |
| t-Bu | Me | H | Me | OCF₃ |
| t-Bu | Cl | H | Me | OCF₃ |
| t-Bu | Me | Cl | Me | OCF₃ |
| t-Bu | Cl | Cl | Me | OCF₃ |
| t-Bu | Me | Br | Me | OCF₃ |
| t-Bu | Cl | Br | Me | OCF₃ |
| Et | Me | H | Me | OCF₃ |
| Et | Cl | H | Me | OCF₃ |
| Et | Me | Cl | Me | OCF₃ |
| Et | Cl | Cl | Me | OCF₃ |
| Et | Me | Br | Me | OCF₃ |
| Et | Cl | Br | Me | OCF₃ |
| Me | Me | H | Me | OCF₃ |

TABLE 1-continued

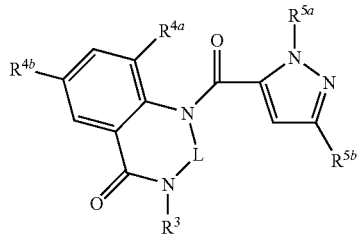

| R³ | R⁴ᵃ | R⁴ᵇ | R⁵ᵃ | R⁵ᵇ |
|---|---|---|---|---|
| Me | Cl | H | Me | OCF₃ |
| Me | Me | Cl | Me | OCF₃ |
| Me | Cl | Cl | Me | OCF₃ |
| Me | Me | Br | Me | OCF₃ |
| Me | Cl | Br | Me | OCF₃ |
| H | Me | H | Me | CF(CF₃)₂ |
| H | Cl | H | Me | CF(CF₃)₂ |
| H | Me | Cl | Me | CF(CF₃)₂ |
| H | Cl | Cl | Me | CF(CF₃)₂ |
| H | Me | Br | Me | CF(CF₃)₂ |
| H | Cl | Br | Me | CF(CF₃)₂ |
| i-Pr | Me | H | Me | CF(CF₃)₂ |
| i-Pr | Cl | H | Me | CF(CF₃)₂ |
| i-Pr | Me | Cl | Me | CF(CF₃)₂ |
| i-Pr | Cl | Cl | Me | CF(CF₃)₂ |
| i-Pr | Me | Br | Me | CF(CF₃)₂ |
| i-Pr | Cl | Br | Me | CF(CF₃)₂ |
| t-Bu | Me | H | Me | CF(CF₃)₂ |
| t-Bu | Cl | H | Me | CF(CF₃)₂ |
| t-Bu | Me | Cl | Me | CF(CF₃)₂ |
| t-Bu | Cl | Cl | Me | CF(CF₃)₂ |
| t-Bu | Me | Br | Me | CF(CF₃)₂ |
| t-Bu | Cl | Br | Me | CF(CF₃)₂ |
| Et | Me | H | Me | CF(CF₃)₂ |
| Et | Cl | H | Me | CF(CF₃)₂ |
| Et | Me | Cl | Me | CF(CF₃)₂ |
| Et | Cl | Cl | Me | CF(CF₃)₂ |
| Et | Me | Br | Me | CF(CF₃)₂ |
| Et | Cl | Br | Me | CF(CF₃)₂ |
| Me | Me | H | Me | CF(CF₃)₂ |
| Me | Cl | H | Me | CF(CF₃)₂ |
| Me | Me | Cl | Me | CF(CF₃)₂ |
| Me | Cl | Cl | Me | CF(CF₃)₂ |
| Me | Me | Br | Me | CF(CF₃)₂ |
| Me | Cl | Br | Me | CF(CF₃)₂ |

TABLE 2

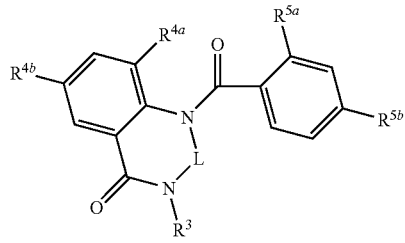

| R³ | R⁴ᵃ | R⁴ᵇ | R⁵ᵃ | R⁵ᵇ |
|---|---|---|---|---|
| L is C=O | | | | |
| H | Me | H | Me | CF₃ |
| H | Cl | H | Me | CF₃ |
| H | Me | Cl | Me | CF₃ |
| H | Cl | Cl | Me | CF₃ |
| H | Me | Br | Me | CF₃ |
| H | Cl | Br | Me | CF₃ |
| i-Pr | Me | H | Me | CF₃ |
| i-Pr | Cl | H | Me | CF₃ |
| i-Pr | Me | Cl | Me | CF₃ |

TABLE 2-continued

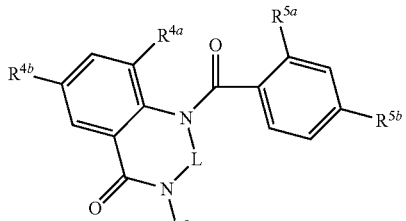

| R³ | R⁴ᵃ | R⁴ᵇ | R⁵ᵃ | R⁵ᵇ |
|---|---|---|---|---|
| i-Pr | Cl | Cl | Me | CF₃ |
| i-Pr | Me | Br | Me | CF₃ |
| i-Pr | Cl | Br | Me | CF₃ |
| t-Bu | Me | H | Me | CF₃ |
| t-Bu | Cl | H | Me | CF₃ |
| t-Bu | Me | Cl | Me | CF₃ |
| t-Bu | Cl | Cl | Me | CF₃ |
| t-Bu | Me | Br | Me | CF₃ |
| t-Bu | Cl | Br | Me | CF₃ |
| Et | Me | H | Me | CF₃ |
| Et | Cl | H | Me | CF₃ |
| Et | Me | Cl | Me | CF₃ |
| Et | Cl | Cl | Me | CF₃ |
| Et | Me | Br | Me | CF₃ |
| Et | Cl | Br | Me | CF₃ |
| Me | Me | H | Me | CF₃ |
| Me | Cl | H | Me | CF₃ |
| Me | Me | Cl | Me | CF₃ |
| Me | Cl | Cl | Me | CF₃ |
| Me | Me | Br | Me | CF₃ |
| Me | Cl | Br | Me | CF₃ |
| H | Me | H | Me | OCF₃ |
| H | Cl | H | Me | OCF₃ |
| H | Me | Cl | Me | OCF₃ |
| H | Cl | Cl | Me | OCF₃ |
| H | Me | Br | Me | OCF₃ |
| H | Cl | Br | Me | OCF₃ |
| i-Pr | Me | H | Me | OCF₃ |
| i-Pr | Cl | H | Me | OCF₃ |
| i-Pr | Me | Cl | Me | OCF₃ |
| i-Pr | Cl | Cl | Me | OCF₃ |
| i-Pr | Me | Br | Me | OCF₃ |
| i-Pr | Cl | Br | Me | OCF₃ |
| t-Bu | Me | H | Me | OCF₃ |
| t-Bu | Cl | H | Me | OCF₃ |
| t-Bu | Me | Cl | Me | OCF₃ |
| t-Bu | Cl | Cl | Me | OCF₃ |
| t-Bu | Me | Br | Me | OCF₃ |
| t-Bu | Cl | Br | Me | OCF₃ |
| Et | Me | H | Me | OCF₃ |
| Et | Cl | H | Me | OCF₃ |
| Et | Me | Cl | Me | OCF₃ |
| Et | Cl | Cl | Me | OCF₃ |
| Et | Me | Br | Me | OCF₃ |
| Et | Cl | Br | Me | OCF₃ |
| Me | Me | H | Me | OCF₃ |
| Me | Cl | H | Me | OCF₃ |
| Me | Me | Cl | Me | OCF₃ |
| Me | Cl | Cl | Me | OCF₃ |
| Me | Me | Br | Me | OCF₃ |
| Me | Cl | Br | Me | OCF₃ |
| H | Me | H | Me | CF(CF₃)₂ |
| H | Cl | H | Me | CF(CF₃)₂ |
| H | Me | Cl | Me | CF(CF₃)₂ |
| H | Cl | Cl | Me | CF(CF₃)₂ |
| H | Me | Br | Me | CF(CF₃)₂ |
| H | Cl | Br | Me | CF(CF₃)₂ |
| i-Pr | Me | H | Me | CF(CF₃)₂ |
| i-Pr | Cl | H | Me | CF(CF₃)₂ |
| i-Pr | Me | Cl | Me | CF(CF₃)₂ |
| i-Pr | Cl | Cl | Me | CF(CF₃)₂ |
| i-Pr | Me | Br | Me | CF(CF₃)₂ |
| i-Pr | Cl | Br | Me | CF(CF₃)₂ |
| t-Bu | Me | H | Me | CF(CF₃)₂ |
| t-Bu | Cl | H | Me | CF(CF₃)₂ |
| t-Bu | Me | Cl | Me | CF(CF₃)₂ |
| t-Bu | Cl | Cl | Me | CF(CF₃)₂ |
| t-Bu | Me | Br | Me | CF(CF₃)₂ |
| t-Bu | Cl | Br | Me | CF(CF₃)₂ |
| Et | Me | H | Me | CF(CF₃)₂ |
| Et | Cl | H | Me | CF(CF₃)₂ |
| Et | Me | Cl | Me | CF(CF₃)₂ |
| Et | Cl | Cl | Me | CF(CF₃)₂ |
| Et | Me | Br | Me | CF(CF₃)₂ |
| Et | Cl | Br | Me | CF(CF₃)₂ |
| Me | Me | H | Me | CF(CF₃)₂ |
| Me | Cl | H | Me | CF(CF₃)₂ |
| Me | Me | Cl | Me | CF(CF₃)₂ |
| Me | Cl | Cl | Me | CF(CF₃)₂ |
| Me | Me | Br | Me | CF(CF₃)₂ |
| Me | Cl | Br | Me | CF(CF₃)₂ |
| L is CH₂ | | | | |
| H | Me | H | Me | CF₃ |
| H | Cl | H | Me | CF₃ |
| H | Me | Cl | Me | CF₃ |
| H | Cl | Cl | Me | CF₃ |
| H | Me | Br | Me | CF₃ |
| H | Cl | Br | Me | CF₃ |
| i-Pr | Me | H | Me | CF₃ |
| i-Pr | Cl | H | Me | CF₃ |
| i-Pr | Me | Cl | Me | CF₃ |
| i-Pr | Cl | Cl | Me | CF₃ |
| i-Pr | Me | Br | Me | CF₃ |
| i-Pr | Cl | Br | Me | CF₃ |
| t-Bu | Me | H | Me | CF₃ |
| t-Bu | Cl | H | Me | CF₃ |
| t-Bu | Me | Cl | Me | CF₃ |
| t-Bu | Cl | Cl | Me | CF₃ |
| t-Bu | Me | Br | Me | CF₃ |
| t-Bu | Cl | Br | Me | CF₃ |
| Et | Me | H | Me | CF₃ |
| Et | Cl | H | Me | CF₃ |
| Et | Me | Cl | Me | CF₃ |
| Et | Cl | Cl | Me | CF₃ |
| Et | Me | Br | Me | CF₃ |
| Et | Cl | Br | Me | CF₃ |
| Me | Me | H | Me | CF₃ |
| Me | Cl | H | Me | CF₃ |
| Me | Me | Cl | Me | CF₃ |
| Me | Cl | Cl | Me | CF₃ |
| Me | Me | Br | Me | CF₃ |
| Me | Cl | Br | Me | CF₃ |
| H | Me | H | Me | OCF₃ |
| H | Cl | H | Me | OCF₃ |
| H | Me | Cl | Me | OCF₃ |
| H | Cl | Cl | Me | OCF₃ |
| H | Me | Br | Me | OCF₃ |
| H | Cl | Br | Me | OCF₃ |
| i-Pr | Me | H | Me | OCF₃ |
| i-Pr | Cl | H | Me | OCF₃ |
| i-Pr | Me | Cl | Me | OCF₃ |
| i-Pr | Cl | Cl | Me | OCF₃ |
| i-Pr | Me | Br | Me | OCF₃ |
| i-Pr | Cl | Br | Me | OCF₃ |
| t-Bu | Me | H | Me | OCF₃ |
| t-Bu | Cl | H | Me | OCF₃ |
| t-Bu | Me | Cl | Me | OCF₃ |
| t-Bu | Cl | Cl | Me | OCF₃ |
| t-Bu | Me | Br | Me | OCF₃ |

TABLE 2-continued

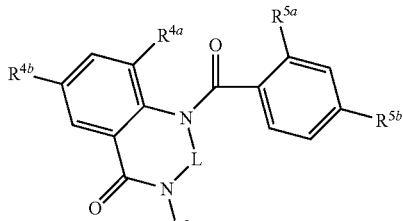
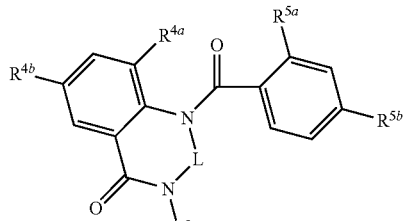

| R³ | R⁴ᵃ | R⁴ᵇ | R⁵ᵃ | R⁵ᵇ |
|---|---|---|---|---|
| t-Bu | Cl | Br | Me | OCF₃ |
| Et | Me | H | Me | OCF₃ |
| Et | Cl | H | Me | OCF₃ |
| Et | Me | Cl | Me | OCF₃ |
| Et | Cl | Cl | Me | OCF₃ |
| Et | Me | Br | Me | OCF₃ |
| Et | Cl | Br | Me | OCF₃ |
| Me | Me | H | Me | OCF₃ |
| Me | Cl | H | Me | OCF₃ |
| Me | Me | Cl | Me | OCF₃ |
| Me | Cl | Cl | Me | OCF₃ |
| Me | Me | Br | Me | OCF₃ |
| Me | Cl | Br | Me | OCF₃ |
| H | Me | H | Me | CF(CF₃)₂ |
| H | Cl | H | Me | CF(CF₃)₂ |
| H | Me | Cl | Me | CF(CF₃)₂ |
| H | Cl | Cl | Me | CF(CF₃)₂ |
| H | Me | Br | Me | CF(CF₃)₂ |
| H | Cl | Br | Me | CF(CF₃)₂ |
| i-Pr | Me | H | Me | CF(CF₃)₂ |
| i-Pr | Cl | H | Me | CF(CF₃)₂ |
| i-Pr | Me | Cl | Me | CF(CF₃)₂ |
| i-Pr | Cl | Cl | Me | CF(CF₃)₂ |
| i-Pr | Me | Br | Me | CF(CF₃)₂ |
| i-Pr | Cl | Br | Me | CF(CF₃)₂ |
| t-Bu | Me | H | Me | CF(CF₃)₂ |
| t-Bu | Cl | H | Me | CF(CF₃)₂ |
| t-Bu | Me | Cl | Me | CF(CF₃)₂ |
| t-Bu | Cl | Cl | Me | CF(CF₃)₂ |
| t-Bu | Me | Br | Me | CF(CF₃)₂ |
| t-Bu | Cl | Br | Me | CF(CF₃)₂ |
| Et | Me | H | Me | CF(CF₃)₂ |
| Et | Cl | H | Me | CF(CF₃)₂ |
| Et | Me | Cl | Me | CF(CF₃)₂ |
| Et | Cl | Cl | Me | CF(CF₃)₂ |
| Et | Me | Br | Me | CF(CF₃)₂ |
| Et | Cl | Br | Me | CF(CF₃)₂ |
| Me | Me | H | Me | CF(CF₃)₂ |
| Me | Cl | H | Me | CF(CF₃)₂ |
| Me | Me | Cl | Me | CF(CF₃)₂ |
| Me | Cl | Cl | Me | CF(CF₃)₂ |
| Me | Me | Br | Me | CF(CF₃)₂ |
| Me | Cl | Br | Me | CF(CF₃)₂ |
| L is CH₂CH₂ | | | | |
| H | Me | H | Me | CF₃ |
| H | Cl | H | Me | CF₃ |
| H | Me | Cl | Me | CF₃ |
| H | Cl | Cl | Me | CF₃ |
| H | Me | Br | Me | CF₃ |
| H | Cl | Br | Me | CF₃ |
| i-Pr | Me | H | Me | CF₃ |
| i-Pr | Cl | H | Me | CF₃ |
| i-Pr | Me | Cl | Me | CF₃ |
| i-Pr | Cl | Cl | Me | CF₃ |
| i-Pr | Me | Br | Me | CF₃ |
| i-Pr | Cl | Br | Me | CF₃ |
| t-Bu | Me | H | Me | CF₃ |
| t-Bu | Cl | H | Me | CF₃ |
| t-Bu | Me | Cl | Me | CF₃ |
| t-Bu | Cl | Cl | Me | CF₃ |
| t-Bu | Me | Br | Me | CF₃ |
| t-Bu | Cl | Br | Me | CF₃ |
| Et | Me | H | Me | CF₃ |
| Et | Cl | H | Me | CF₃ |
| Et | Me | Cl | Me | CF₃ |
| Et | Cl | Cl | Me | CF₃ |
| Et | Me | Br | Me | CF₃ |
| Et | Cl | Br | Me | CF₃ |
| Me | Me | H | Me | CF₃ |
| Me | Cl | H | Me | CF₃ |
| Me | Me | Cl | Me | CF₃ |
| Me | Cl | Cl | Me | CF₃ |
| Me | Me | Br | Me | CF₃ |
| Me | Cl | Br | Me | CF₃ |
| H | Me | H | Me | OCF₃ |
| H | Cl | H | Me | OCF₃ |
| H | Me | Cl | Me | OCF₃ |
| H | Cl | Cl | Me | OCF₃ |
| H | Me | Br | Me | OCF₃ |
| H | Cl | Br | Me | OCF₃ |
| i-Pr | Me | H | Me | OCF₃ |
| i-Pr | Cl | H | Me | OCF₃ |
| i-Pr | Me | Cl | Me | OCF₃ |
| i-Pr | Cl | Cl | Me | OCF₃ |
| i-Pr | Me | Br | Me | OCF₃ |
| i-Pr | Cl | Br | Me | OCF₃ |
| t-Bu | Me | H | Me | OCF₃ |
| t-Bu | Cl | H | Me | OCF₃ |
| t-Bu | Me | Cl | Me | OCF₃ |
| t-Bu | Cl | Cl | Me | OCF₃ |
| t-Bu | Me | Br | Me | OCF₃ |
| t-Bu | Cl | Br | Me | OCF₃ |
| Et | Me | H | Me | OCF₃ |
| Et | Cl | H | Me | OCF₃ |
| Et | Me | Cl | Me | OCF₃ |
| Et | Cl | Cl | Me | OCF₃ |
| Et | Me | Br | Me | OCF₃ |
| Et | Cl | Br | Me | OCF₃ |
| Me | Me | H | Me | OCF₃ |
| Me | Cl | H | Me | OCF₃ |
| Me | Me | Cl | Me | OCF₃ |
| Me | Cl | Cl | Me | OCF₃ |
| Me | Me | Br | Me | OCF₃ |
| Me | Cl | Br | Me | OCF₃ |
| H | Me | H | Me | CF(CF₃)₂ |
| H | Cl | H | Me | CF(CF₃)₂ |
| H | Me | Cl | Me | CF(CF₃)₂ |
| H | Cl | Cl | Me | CF(CF₃)₂ |
| H | Me | Br | Me | CF(CF₃)₂ |
| H | Cl | Br | Me | CF(CF₃)₂ |
| i-Pr | Me | H | Me | CF(CF₃)₂ |
| i-Pr | Cl | H | Me | CF(CF₃)₂ |
| i-Pr | Me | Cl | Me | CF(CF₃)₂ |
| i-Pr | Cl | Cl | Me | CF(CF₃)₂ |
| i-Pr | Me | Br | Me | CF(CF₃)₂ |
| i-Pr | Cl | Br | Me | CF(CF₃)₂ |
| t-Bu | Me | H | Me | CF(CF₃)₂ |
| t-Bu | Cl | H | Me | CF(CF₃)₂ |
| t-Bu | Me | Cl | Me | CF(CF₃)₂ |
| t-Bu | Cl | Cl | Me | CF(CF₃)₂ |
| t-Bu | Me | Br | Me | CF(CF₃)₂ |
| t-Bu | Cl | Br | Me | CF(CF₃)₂ |
| Et | Me | H | Me | CF(CF₃)₂ |
| Et | Cl | H | Me | CF(CF₃)₂ |
| Et | Me | Cl | Me | CF(CF₃)₂ |
| Et | Cl | Cl | Me | CF(CF₃)₂ |
| Et | Me | Br | Me | CF(CF₃)₂ |
| Et | Cl | Br | Me | CF(CF₃)₂ |
| Me | Me | H | Me | CF(CF₃)₂ |

TABLE 2-continued

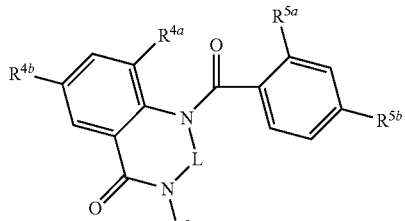

| R³ | R⁴ᵃ | R⁴ᵇ | R⁵ᵃ | R⁵ᵇ |
|---|---|---|---|---|
| Me | Cl | H | Me | CF(CF₃)₂ |
| Me | Me | Cl | Me | CF(CF₃)₂ |
| Me | Cl | Cl | Me | CF(CF₃)₂ |
| Me | Me | Br | Me | CF(CF₃)₂ |
| Me | Cl | Br | Me | CF(CF₃)₂ |

TABLE 3

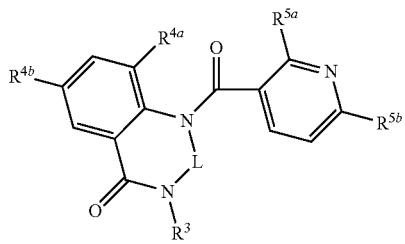

| R³ | R⁴ᵃ | R⁴ᵇ | R⁵ᵃ | R⁵ᵇ |
|---|---|---|---|---|
| *L is C=O* | | | | |
| H | Me | H | Me | CF₃ |
| H | Cl | H | Me | CF₃ |
| H | Me | Cl | Me | CF₃ |
| H | Cl | Cl | Me | CF₃ |
| H | Me | Br | Me | CF₃ |
| H | Cl | Br | Me | CF₃ |
| i-Pr | Me | H | Me | CF₃ |
| i-Pr | Cl | H | Me | CF₃ |
| i-Pr | Me | Cl | Me | CF₃ |
| i-Pr | Cl | Cl | Me | CF₃ |
| i-Pr | Me | Br | Me | CF₃ |
| i-Pr | Cl | Br | Me | CF₃ |
| t-Bu | Me | H | Me | CF₃ |
| t-Bu | Cl | H | Me | CF₃ |
| t-Bu | Me | Cl | Me | CF₃ |
| t-Bu | Cl | Cl | Me | CF₃ |
| t-Bu | Me | Br | Me | CF₃ |
| t-Bu | Cl | Br | Me | CF₃ |
| Et | Me | H | Me | CF₃ |
| Et | Cl | H | Me | CF₃ |
| Et | Me | Cl | Me | CF₃ |
| Et | Cl | Cl | Me | CF₃ |
| Et | Me | Br | Me | CF₃ |
| Et | Cl | Br | Me | CF₃ |
| Me | Me | H | Me | CF₃ |
| Me | Cl | H | Me | CF₃ |
| Me | Me | Cl | Me | CF₃ |
| Me | Cl | Cl | Me | CF₃ |
| Me | Me | Br | Me | CF₃ |
| Me | Cl | Br | Me | CF₃ |
| H | Me | H | Me | OCF₃ |
| H | Cl | H | Me | OCF₃ |
| H | Me | Cl | Me | OCF₃ |
| H | Cl | Cl | Me | OCF₃ |
| H | Me | Br | Me | OCF₃ |
| H | Cl | Br | Me | OCF₃ |
| i-Pr | Me | H | Me | OCF₃ |
| i-Pr | Cl | H | Me | OCF₃ |
| i-Pr | Me | Cl | Me | OCF₃ |

TABLE 3-continued

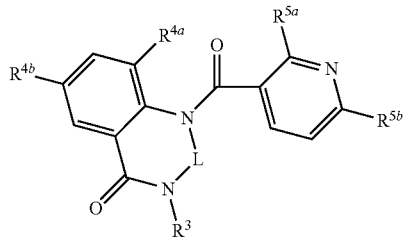

| R³ | R⁴ᵃ | R⁴ᵇ | R⁵ᵃ | R⁵ᵇ |
|---|---|---|---|---|
| i-Pr | Cl | Cl | Me | OCF₃ |
| i-Pr | Me | Br | Me | OCF₃ |
| i-Pr | Cl | Br | Me | OCF₃ |
| t-Bu | Me | H | Me | OCF₃ |
| t-Bu | Cl | H | Me | OCF₃ |
| t-Bu | Me | Cl | Me | OCF₃ |
| t-Bu | Cl | Cl | Me | OCF₃ |
| t-Bu | Me | Br | Me | OCF₃ |
| t-Bu | Cl | Br | Me | OCF₃ |
| Et | Me | H | Me | OCF₃ |
| Et | Cl | H | Me | OCF₃ |
| Et | Me | Cl | Me | OCF₃ |
| Et | Cl | Cl | Me | OCF₃ |
| Et | Me | Br | Me | OCF₃ |
| Et | Cl | Br | Me | OCF₃ |
| Me | Me | H | Me | OCF₃ |
| Me | Cl | H | Me | OCF₃ |
| Me | Me | Cl | Me | OCF₃ |
| Me | Cl | Cl | Me | OCF₃ |
| Me | Me | Br | Me | OCF₃ |
| Me | Cl | Br | Me | OCF₃ |
| H | Me | H | Me | CF(CF₃)₂ |
| H | Cl | H | Me | CF(CF₃)₂ |
| H | Me | Cl | Me | CF(CF₃)₂ |
| H | Cl | Cl | Me | CF(CF₃)₂ |
| H | Me | Br | Me | CF(CF₃)₂ |
| H | Cl | Br | Me | CF(CF₃)₂ |
| i-Pr | Me | H | Me | CF(CF₃)₂ |
| i-Pr | Cl | H | Me | CF(CF₃)₂ |
| i-Pr | Me | Cl | Me | CF(CF₃)₂ |
| i-Pr | Cl | Cl | Me | CF(CF₃)₂ |
| i-Pr | Me | Br | Me | CF(CF₃)₂ |
| i-Pr | Cl | Br | Me | CF(CF₃)₂ |
| t-Bu | Me | H | Me | CF(CF₃)₂ |
| t-Bu | Cl | H | Me | CF(CF₃)₂ |
| t-Bu | Me | Cl | Me | CF(CF₃)₂ |
| t-Bu | Cl | Cl | Me | CF(CF₃)₂ |
| t-Bu | Me | Br | Me | CF(CF₃)₂ |
| t-Bu | Cl | Br | Me | CF(CF₃)₂ |
| Et | Me | H | Me | CF(CF₃)₂ |
| Et | Cl | H | Me | CF(CF₃)₂ |
| Et | Me | Cl | Me | CF(CF₃)₂ |
| Et | Cl | Cl | Me | CF(CF₃)₂ |
| Et | Me | Br | Me | CF(CF₃)₂ |
| Et | Cl | Br | Me | CF(CF₃)₂ |
| Me | Me | H | Me | CF(CF₃)₂ |
| Me | Cl | H | Me | CF(CF₃)₂ |
| Me | Me | Cl | Me | CF(CF₃)₂ |
| Me | Cl | Cl | Me | CF(CF₃)₂ |
| Me | Me | Br | Me | CF(CF₃)₂ |
| Me | Cl | Br | Me | CF(CF₃)₂ |
| *L is CH₂* | | | | |
| H | Me | H | Me | CF₃ |
| H | Cl | H | Me | CF₃ |
| H | Me | Cl | Me | CF₃ |
| H | Cl | Cl | Me | CF₃ |
| H | Me | Br | Me | CF₃ |
| H | Cl | Br | Me | CF₃ |
| i-Pr | Me | H | Me | CF₃ |
| i-Pr | Cl | H | Me | CF₃ |
| i-Pr | Me | Cl | Me | CF₃ |
| i-Pr | Cl | Cl | Me | CF₃ |
| i-Pr | Me | Br | Me | CF₃ |

TABLE 3-continued

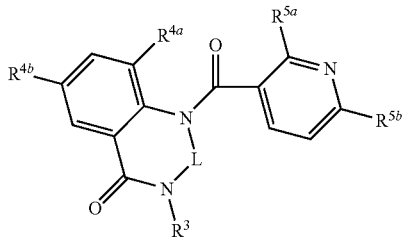

| R³ | R⁴ᵃ | R⁴ᵇ | R⁵ᵃ | R⁵ᵇ |
|---|---|---|---|---|
| i-Pr | Cl | Br | Me | CF₃ |
| t-Bu | Me | H | Me | CF₃ |
| t-Bu | Cl | H | Me | CF₃ |
| t-Bu | Me | Cl | Me | CF₃ |
| t-Bu | Cl | Cl | Me | CF₃ |
| t-Bu | Me | Br | Me | CF₃ |
| t-Bu | Cl | Br | Me | CF₃ |
| Et | Me | H | Me | CF₃ |
| Et | Cl | H | Me | CF₃ |
| Et | Me | Cl | Me | CF₃ |
| Et | Cl | Cl | Me | CF₃ |
| Et | Me | Br | Me | CF₃ |
| Et | Cl | Br | Me | CF₃ |
| Me | Me | H | Me | CF₃ |
| Me | Cl | H | Me | CF₃ |
| Me | Me | Cl | Me | CF₃ |
| Me | Cl | Cl | Me | CF₃ |
| Me | Me | Br | Me | CF₃ |
| Me | Cl | Br | Me | CF₃ |
| H | Me | H | Me | OCF₃ |
| H | Cl | H | Me | OCF₃ |
| H | Me | Cl | Me | OCF₃ |
| H | Cl | Cl | Me | OCF₃ |
| H | Me | Br | Me | OCF₃ |
| H | Cl | Br | Me | OCF₃ |
| i-Pr | Me | H | Me | OCF₃ |
| i-Pr | Cl | H | Me | OCF₃ |
| i-Pr | Me | Cl | Me | OCF₃ |
| i-Pr | Cl | Cl | Me | OCF₃ |
| i-Pr | Me | Br | Me | OCF₃ |
| i-Pr | Cl | Br | Me | OCF₃ |
| t-Bu | Me | H | Me | OCF₃ |
| t-Bu | Cl | H | Me | OCF₃ |
| t-Bu | Me | Cl | Me | OCF₃ |
| t-Bu | Cl | Cl | Me | OCF₃ |
| t-Bu | Me | Br | Me | OCF₃ |
| t-Bu | Cl | Br | Me | OCF₃ |
| Et | Me | H | Me | OCF₃ |
| Et | Cl | H | Me | OCF₃ |
| Et | Me | Cl | Me | OCF₃ |
| Et | Cl | Cl | Me | OCF₃ |
| Et | Me | Br | Me | OCF₃ |
| Et | Cl | Br | Me | OCF₃ |
| Me | Me | H | Me | OCF₃ |
| Me | Cl | H | Me | OCF₃ |
| Me | Me | Cl | Me | OCF₃ |
| Me | Cl | Cl | Me | OCF₃ |
| Me | Me | Br | Me | OCF₃ |
| Me | Cl | Br | Me | OCF₃ |
| H | Me | H | Me | CF(CF₃)₂ |
| H | Cl | H | Me | CF(CF₃)₂ |
| H | Me | Cl | Me | CF(CF₃)₂ |
| H | Cl | Cl | Me | CF(CF₃)₂ |
| H | Me | Br | Me | CF(CF₃)₂ |
| H | Cl | Br | Me | CF(CF₃)₂ |
| i-Pr | Me | H | Me | CF(CF₃)₂ |
| i-Pr | Cl | H | Me | CF(CF₃)₂ |
| i-Pr | Me | Cl | Me | CF(CF₃)₂ |
| i-Pr | Cl | Cl | Me | CF(CF₃)₂ |
| i-Pr | Me | Br | Me | CF(CF₃)₂ |
| i-Pr | Cl | Br | Me | CF(CF₃)₂ |
| t-Bu | Me | H | Me | CF(CF₃)₂ |
| t-Bu | Cl | H | Me | CF(CF₃)₂ |
| t-Bu | Me | Cl | Me | CF(CF₃)₂ |

TABLE 3-continued

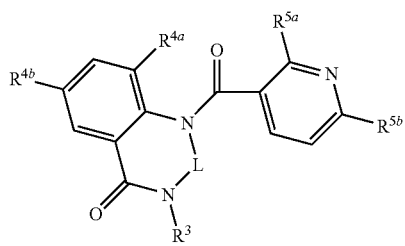

| R³ | R⁴ᵃ | R⁴ᵇ | R⁵ᵃ | R⁵ᵇ |
|---|---|---|---|---|
| t-Bu | Cl | Cl | Me | CF(CF₃)₂ |
| t-Bu | Me | Br | Me | CF(CF₃)₂ |
| t-Bu | Cl | Br | Me | CF(CF₃)₂ |
| Et | Me | H | Me | CF(CF₃)₂ |
| Et | Cl | H | Me | CF(CF₃)₂ |
| Et | Me | Cl | Me | CF(CF₃)₂ |
| Et | Cl | Cl | Me | CF(CF₃)₂ |
| Et | Me | Br | Me | CF(CF₃)₂ |
| Et | Cl | Br | Me | CF(CF₃)₂ |
| Me | Me | H | Me | CF(CF₃)₂ |
| Me | Cl | H | Me | CF(CF₃)₂ |
| Me | Me | Cl | Me | CF(CF₃)₂ |
| Me | Cl | Cl | Me | CF(CF₃)₂ |
| Me | Me | Br | Me | CF(CF₃)₂ |
| Me | Cl | Br | Me | CF(CF₃)₂ |
| L is CH₂CH₂ | | | | |
| H | Me | H | Me | CF₃ |
| H | Cl | H | Me | CF₃ |
| H | Me | Cl | Me | CF₃ |
| H | Cl | Cl | Me | CF₃ |
| H | Me | Br | Me | CF₃ |
| H | Cl | Br | Me | CF₃ |
| i-Pr | Me | H | Me | CF₃ |
| i-Pr | Cl | H | Me | CF₃ |
| i-Pr | Me | Cl | Me | CF₃ |
| i-Pr | Cl | Cl | Me | CF₃ |
| i-Pr | Me | Br | Me | CF₃ |
| i-Pr | Cl | Br | Me | CF₃ |
| t-Bu | Me | H | Me | CF₃ |
| t-Bu | Cl | H | Me | CF₃ |
| t-Bu | Me | Cl | Me | CF₃ |
| t-Bu | Cl | Cl | Me | CF₃ |
| t-Bu | Me | Br | Me | CF₃ |
| t-Bu | Cl | Br | Me | CF₃ |
| Et | Me | H | Me | CF₃ |
| Et | Cl | H | Me | CF₃ |
| Et | Me | Cl | Me | CF₃ |
| Et | Cl | Cl | Me | CF₃ |
| Et | Me | Br | Me | CF₃ |
| Et | Cl | Br | Me | CF₃ |
| Me | Me | H | Me | CF₃ |
| Me | Cl | H | Me | CF₃ |
| Me | Me | Cl | Me | CF₃ |
| Me | Cl | Cl | Me | CF₃ |
| Me | Me | Br | Me | CF₃ |
| Me | Cl | Br | Me | CF₃ |
| H | Me | H | Me | OCF₃ |
| H | Cl | H | Me | OCF₃ |
| H | Me | Cl | Me | OCF₃ |
| H | Cl | Cl | Me | OCF₃ |
| H | Me | Br | Me | OCF₃ |
| H | Cl | Br | Me | OCF₃ |
| i-Pr | Me | H | Me | OCF₃ |
| i-Pr | Cl | H | Me | OCF₃ |

TABLE 3-continued

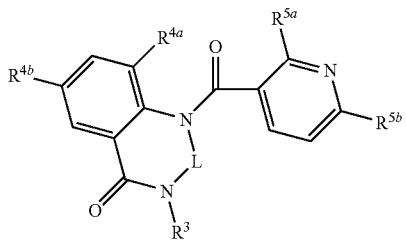

| R³ | R⁴ᵃ | R⁴ᵇ | R⁵ᵃ | R⁵ᵇ |
|---|---|---|---|---|
| i-Pr | Me | Cl | Me | OCF₃ |
| i-Pr | Cl | Cl | Me | OCF₃ |
| i-Pr | Me | Br | Me | OCF₃ |
| i-Pr | Cl | Br | Me | OCF₃ |
| t-Bu | Me | H | Me | OCF₃ |
| t-Bu | Cl | H | Me | OCF₃ |
| t-Bu | Me | Cl | Me | OCF₃ |
| t-Bu | Cl | Cl | Me | OCF₃ |
| t-Bu | Me | Br | Me | OCF₃ |
| t-Bu | Cl | Br | Me | OCF₃ |
| Et | Me | H | Me | OCF₃ |
| Et | Cl | H | Me | OCF₃ |
| Et | Me | Cl | Me | OCF₃ |
| Et | Cl | Cl | Me | OCF₃ |
| Et | Me | Br | Me | OCF₃ |
| Et | Cl | Br | Me | OCF₃ |
| Me | Me | H | Me | OCF₃ |
| Me | Cl | H | Me | OCF₃ |
| Me | Me | Cl | Me | OCF₃ |
| Me | Cl | Cl | Me | OCF₃ |
| Me | Me | Br | Me | OCF₃ |
| Me | Cl | Br | Me | OCF₃ |
| H | Me | H | Me | CF(CF₃)₂ |
| H | Cl | H | Me | CF(CF₃)₂ |
| H | Me | Cl | Me | CF(CF₃)₂ |
| H | Cl | Cl | Me | CF(CF₃)₂ |
| H | Me | Br | Me | CF(CF₃)₂ |
| H | Cl | Br | Me | CF(CF₃)₂ |
| i-Pr | Me | H | Me | CF(CF₃)₂ |
| i-Pr | Cl | H | Me | CF(CF₃)₂ |
| i-Pr | Me | Cl | Me | CF(CF₃)₂ |
| i-Pr | Cl | Cl | Me | CF(CF₃)₂ |
| i-Pr | Me | Br | Me | CF(CF₃)₂ |
| i-Pr | Cl | Br | Me | CF(CF₃)₂ |
| t-Bu | Me | H | Me | CF(CF₃)₂ |
| t-Bu | Cl | H | Me | CF(CF₃)₂ |
| t-Bu | Me | Cl | Me | CF(CF₃)₂ |
| t-Bu | Cl | Cl | Me | CF(CF₃)₂ |
| t-Bu | Me | Br | Me | CF(CF₃)₂ |
| t-Bu | Cl | Br | Me | CF(CF₃)₂ |
| Et | Me | H | Me | CF(CF₃)₂ |
| Et | Cl | H | Me | CF(CF₃)₂ |
| Et | Me | Cl | Me | CF(CF₃)₂ |
| Et | Cl | Cl | Me | CF(CF₃)₂ |
| Et | Me | Br | Me | CF(CF₃)₂ |
| Et | Cl | Br | Me | CF(CF₃)₂ |
| Me | Me | H | Me | CF(CF₃)₂ |
| Me | Cl | H | Me | CF(CF₃)₂ |
| Me | Me | Cl | Me | CF(CF₃)₂ |
| Me | Cl | Cl | Me | CF(CF₃)₂ |
| Me | Me | Br | Me | CF(CF₃)₂ |
| Me | Cl | Br | Me | CF(CF₃)₂ |

TABLE 4

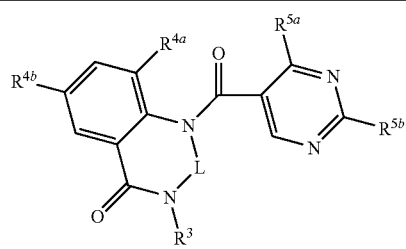

| R³ | R⁴ᵃ | R⁴ᵇ | R⁵ᵃ | R⁵ᵇ |
|---|---|---|---|---|
| L is C=O ||||||
| H | Me | H | Me | CF₃ |
| H | Cl | H | Me | CF₃ |
| H | Me | Cl | Me | CF₃ |
| H | Cl | Cl | Me | CF₃ |
| H | Me | Br | Me | CF₃ |
| H | Cl | Br | Me | CF₃ |
| i-Pr | Me | H | Me | CF₃ |
| i-Pr | Cl | H | Me | CF₃ |
| i-Pr | Me | Cl | Me | CF₃ |
| i-Pr | Cl | Cl | Me | CF₃ |
| i-Pr | Me | Br | Me | CF₃ |
| i-Pr | Cl | Br | Me | CF₃ |
| t-Bu | Me | H | Me | CF₃ |
| t-Bu | Cl | H | Me | CF₃ |
| t-Bu | Me | Cl | Me | CF₃ |
| t-Bu | Cl | Cl | Me | CF₃ |
| t-Bu | Me | Br | Me | CF₃ |
| t-Bu | Cl | Br | Me | CF₃ |
| Et | Me | H | Me | CF₃ |
| Et | Cl | H | Me | CF₃ |
| Et | Me | Cl | Me | CF₃ |
| Et | Cl | Cl | Me | CF₃ |
| Et | Me | Br | Me | CF₃ |
| Et | Cl | Br | Me | CF₃ |
| Me | Me | H | Me | CF₃ |
| Me | Cl | H | Me | CF₃ |
| Me | Me | Cl | Me | CF₃ |
| Me | Cl | Cl | Me | CF₃ |
| Me | Me | Br | Me | CF₃ |
| Me | Cl | Br | Me | CF₃ |
| H | Me | H | Me | OCF₃ |
| H | Cl | H | Me | OCF₃ |
| H | Me | Cl | Me | OCF₃ |
| H | Cl | Cl | Me | OCF₃ |
| H | Me | Br | Me | OCF₃ |
| H | Cl | Br | Me | OCF₃ |
| i-Pr | Me | H | Me | OCF₃ |
| i-Pr | Cl | H | Me | OCF₃ |
| i-Pr | Me | Cl | Me | OCF₃ |
| i-Pr | Cl | Cl | Me | OCF₃ |
| i-Pr | Me | Br | Me | OCF₃ |
| i-Pr | Cl | Br | Me | OCF₃ |
| t-Bu | Me | H | Me | OCF₃ |
| t-Bu | Cl | H | Me | OCF₃ |
| t-Bu | Me | Cl | Me | OCF₃ |
| t-Bu | Cl | Cl | Me | OCF₃ |
| t-Bu | Me | Br | Me | OCF₃ |
| t-Bu | Cl | Br | Me | OCF₃ |
| Et | Me | H | Me | OCF₃ |
| Et | Cl | H | Me | OCF₃ |
| Et | Me | Cl | Me | OCF₃ |
| Et | Cl | Cl | Me | OCF₃ |
| Et | Me | Br | Me | OCF₃ |
| Et | Cl | Br | Me | OCF₃ |
| Me | Me | H | Me | OCF₃ |
| Me | Cl | H | Me | OCF₃ |
| Me | Me | Cl | Me | OCF₃ |
| Me | Cl | Cl | Me | OCF₃ |
| Me | Me | Br | Me | OCF₃ |
| Me | Cl | Br | Me | OCF₃ |
| H | Me | H | Me | CF(CF₃)₂ |
| H | Cl | H | Me | CF(CF₃)₂ |
| H | Me | Cl | Me | CF(CF₃)₂ |

TABLE 4-continued

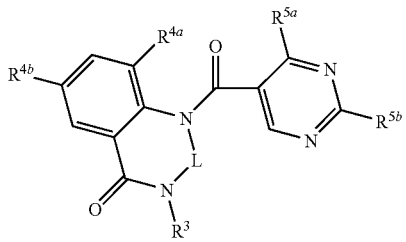

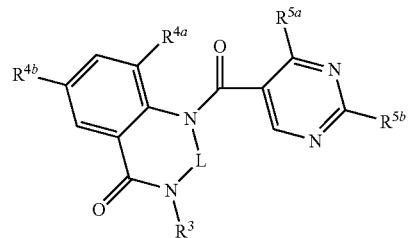

| R³ | R⁴ᵃ | R⁴ᵇ | R⁵ᵃ | R⁵ᵇ |
|---|---|---|---|---|
| H | Cl | Cl | Me | $CF(CF_3)_2$ |
| H | Me | Br | Me | $CF(CF_3)_2$ |
| H | Cl | Br | Me | $CF(CF_3)_2$ |
| i-Pr | Me | H | Me | $CF(CF_3)_2$ |
| i-Pr | Cl | H | Me | $CF(CF_3)_2$ |
| i-Pr | Me | Cl | Me | $CF(CF_3)_2$ |
| i-Pr | Cl | Cl | Me | $CF(CF_3)_2$ |
| i-Pr | Me | Br | Me | $CF(CF_3)_2$ |
| i-Pr | Cl | Br | Me | $CF(CF_3)_2$ |
| t-Bu | Me | H | Me | $CF(CF_3)_2$ |
| t-Bu | Cl | H | Me | $CF(CF_3)_2$ |
| t-Bu | Me | Cl | Me | $CF(CF_3)_2$ |
| t-Bu | Cl | Cl | Me | $CF(CF_3)_2$ |
| t-Bu | Me | Br | Me | $CF(CF_3)_2$ |
| t-Bu | Cl | Br | Me | $CF(CF_3)_2$ |
| Et | Me | H | Me | $CF(CF_3)_2$ |
| Et | Cl | H | Me | $CF(CF_3)_2$ |
| Et | Me | Cl | Me | $CF(CF_3)_2$ |
| Et | Cl | Cl | Me | $CF(CF_3)_2$ |
| Et | Me | Br | Me | $CF(CF_3)_2$ |
| Et | Cl | Br | Me | $CF(CF_3)_2$ |
| Me | Me | H | Me | $CF(CF_3)_2$ |
| Me | Cl | H | Me | $CF(CF_3)_2$ |
| Me | Me | Cl | Me | $CF(CF_3)_2$ |
| Me | Cl | Cl | Me | $CF(CF_3)_2$ |
| Me | Me | Br | Me | $CF(CF_3)_2$ |
| Me | Cl | Br | Me | $CF(CF_3)_2$ |

L is $CH_2$

| R³ | R⁴ᵃ | R⁴ᵇ | R⁵ᵃ | R⁵ᵇ |
|---|---|---|---|---|
| H | Me | H | Me | $CF_3$ |
| H | Cl | H | Me | $CF_3$ |
| H | Me | Cl | Me | $CF_3$ |
| H | Cl | Cl | Me | $CF_3$ |
| H | Me | Br | Me | $CF_3$ |
| H | Cl | Br | Me | $CF_3$ |
| i-Pr | Me | H | Me | $CF_3$ |
| i-Pr | Cl | H | Me | $CF_3$ |
| i-Pr | Me | Cl | Me | $CF_3$ |
| i-Pr | Cl | Cl | Me | $CF_3$ |
| i-Pr | Me | Br | Me | $CF_3$ |
| i-Pr | Cl | Br | Me | $CF_3$ |
| t-Bu | Me | H | Me | $CF_3$ |
| t-Bu | Cl | H | Me | $CF_3$ |
| t-Bu | Me | Cl | Me | $CF_3$ |
| t-Bu | Cl | Cl | Me | $CF_3$ |
| t-Bu | Me | Br | Me | $CF_3$ |
| t-Bu | Cl | Br | Me | $CF_3$ |
| Et | Me | H | Me | $CF_3$ |
| Et | Cl | H | Me | $CF_3$ |
| Et | Me | Cl | Me | $CF_3$ |
| Et | Cl | Cl | Me | $CF_3$ |
| Et | Me | Br | Me | $CF_3$ |
| Et | Cl | Br | Me | $CF_3$ |
| Me | Me | H | Me | $CF_3$ |
| Me | Cl | H | Me | $CF_3$ |
| Me | Me | Cl | Me | $CF_3$ |
| Me | Cl | Cl | Me | $CF_3$ |
| Me | Me | Br | Me | $CF_3$ |
| Me | Cl | Br | Me | $CF_3$ |
| H | Me | H | Me | $OCF_3$ |
| H | Cl | H | Me | $OCF_3$ |
| H | Me | Cl | Me | $OCF_3$ |
| H | Cl | Cl | Me | $OCF_3$ |
| H | Me | Br | Me | $OCF_3$ |
| H | Cl | Br | Me | $OCF_3$ |
| i-Pr | Me | H | Me | $OCF_3$ |
| i-Pr | Cl | H | Me | $OCF_3$ |
| i-Pr | Me | Cl | Me | $OCF_3$ |
| i-Pr | Cl | Cl | Me | $OCF_3$ |
| i-Pr | Me | Br | Me | $OCF_3$ |
| i-Pr | Cl | Br | Me | $OCF_3$ |
| t-Bu | Me | H | Me | $OCF_3$ |
| t-Bu | Cl | H | Me | $OCF_3$ |
| t-Bu | Me | Cl | Me | $OCF_3$ |
| t-Bu | Cl | Cl | Me | $OCF_3$ |
| t-Bu | Me | Br | Me | $OCF_3$ |
| t-Bu | Cl | Br | Me | $OCF_3$ |
| Et | Me | H | Me | $OCF_3$ |
| Et | Cl | H | Me | $OCF_3$ |
| Et | Me | Cl | Me | $OCF_3$ |
| Et | Cl | Cl | Me | $OCF_3$ |
| Et | Me | Br | Me | $OCF_3$ |
| Et | Cl | Br | Me | $OCF_3$ |
| Me | Me | H | Me | $OCF_3$ |
| Me | Cl | H | Me | $OCF_3$ |
| Me | Me | Cl | Me | $OCF_3$ |
| Me | Cl | Cl | Me | $OCF_3$ |
| Me | Me | Br | Me | $OCF_3$ |
| Me | Cl | Br | Me | $OCF_3$ |
| H | Me | H | Me | $CF(CF_3)_2$ |
| H | Cl | H | Me | $CF(CF_3)_2$ |
| H | Me | Cl | Me | $CF(CF_3)_2$ |
| H | Cl | Cl | Me | $CF(CF_3)_2$ |
| H | Me | Br | Me | $CF(CF_3)_2$ |
| H | Cl | Br | Me | $CF(CF_3)_2$ |
| i-Pr | Me | H | Me | $CF(CF_3)_2$ |
| i-Pr | Cl | H | Me | $CF(CF_3)_2$ |
| i-Pr | Me | Cl | Me | $CF(CF_3)_2$ |
| i-Pr | Cl | Cl | Me | $CF(CF_3)_2$ |
| i-Pr | Me | Br | Me | $CF(CF_3)_2$ |
| i-Pr | Cl | Br | Me | $CF(CF_3)_2$ |
| t-Bu | Me | H | Me | $CF(CF_3)_2$ |
| t-Bu | Cl | H | Me | $CF(CF_3)_2$ |
| t-Bu | Me | Cl | Me | $CF(CF_3)_2$ |
| t-Bu | Cl | Cl | Me | $CF(CF_3)_2$ |
| t-Bu | Me | Br | Me | $CF(CF_3)_2$ |
| t-Bu | Cl | Br | Me | $CF(CF_3)_2$ |
| Et | Me | H | Me | $CF(CF_3)_2$ |
| Et | Cl | H | Me | $CF(CF_3)_2$ |
| Et | Me | Cl | Me | $CF(CF_3)_2$ |
| Et | Cl | Cl | Me | $CF(CF_3)_2$ |
| Et | Me | Br | Me | $CF(CF_3)_2$ |
| Et | Cl | Br | Me | $CF(CF_3)_2$ |
| Me | Me | H | Me | $CF(CF_3)_2$ |
| Me | Cl | H | Me | $CF(CF_3)_2$ |
| Me | Me | Cl | Me | $CF(CF_3)_2$ |
| Me | Cl | Cl | Me | $CF(CF_3)_2$ |
| Me | Me | Br | Me | $CF(CF_3)_2$ |
| Me | Cl | Br | Me | $CF(CF_3)_2$ |

L is $CH_2CH_2$

| R³ | R⁴ᵃ | R⁴ᵇ | R⁵ᵃ | R⁵ᵇ |
|---|---|---|---|---|
| H | Me | H | Me | $CF_3$ |
| H | Cl | H | Me | $CF_3$ |
| H | Me | Cl | Me | $CF_3$ |
| H | Cl | Cl | Me | $CF_3$ |
| H | Me | Br | Me | $CF_3$ |
| H | Cl | Br | Me | $CF_3$ |
| i-Pr | Me | H | Me | $CF_3$ |
| i-Pr | Cl | H | Me | $CF_3$ |
| i-Pr | Me | Cl | Me | $CF_3$ |

TABLE 4-continued

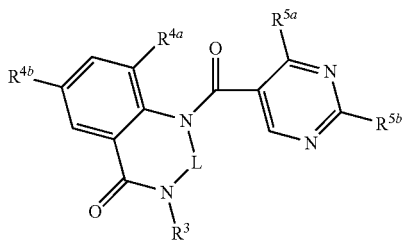

| R³ | R⁴ᵃ | R⁴ᵇ | R⁵ᵃ | R⁵ᵇ |
|---|---|---|---|---|
| i-Pr | Cl | Cl | Me | CF₃ |
| i-Pr | Me | Br | Me | CF₃ |
| i-Pr | Cl | Br | Me | CF₃ |
| t-Bu | Me | H | Me | CF₃ |
| t-Bu | Cl | H | Me | CF₃ |
| t-Bu | Me | Cl | Me | CF₃ |
| t-Bu | Cl | Cl | Me | CF₃ |
| t-Bu | Me | Br | Me | CF₃ |
| t-Bu | Cl | Br | Me | CF₃ |
| Et | Me | H | Me | CF₃ |
| Et | Cl | H | Me | CF₃ |
| Et | Me | Cl | Me | CF₃ |
| Et | Cl | Cl | Me | CF₃ |
| Et | Me | Br | Me | CF₃ |
| Et | Cl | Br | Me | CF₃ |
| Me | Me | H | Me | CF₃ |
| Me | Cl | H | Me | CF₃ |
| Me | Me | Cl | Me | CF₃ |
| Me | Cl | Cl | Me | CF₃ |
| Me | Me | Br | Me | CF₃ |
| Me | Cl | Br | Me | CF₃ |
| H | Me | H | Me | OCF₃ |
| H | Cl | H | Me | OCF₃ |
| H | Me | Cl | Me | OCF₃ |
| H | Cl | Cl | Me | OCF₃ |
| H | Me | Br | Me | OCF₃ |
| H | Cl | Br | Me | OCF₃ |
| i-Pr | Me | H | Me | OCF₃ |
| i-Pr | Cl | H | Me | OCF₃ |
| i-Pr | Me | Cl | Me | OCF₃ |
| i-Pr | Cl | Cl | Me | OCF₃ |
| i-Pr | Me | Br | Me | OCF₃ |
| i-Pr | Cl | Br | Me | OCF₃ |
| t-Bu | Me | H | Me | OCF₃ |
| t-Bu | Cl | H | Me | OCF₃ |
| t-Bu | Me | Cl | Me | OCF₃ |
| t-Bu | Cl | Cl | Me | OCF₃ |
| t-Bu | Me | Br | Me | OCF₃ |
| t-Bu | Cl | Br | Me | OCF₃ |
| Et | Me | H | Me | OCF₃ |
| Et | Cl | H | Me | OCF₃ |
| Et | Me | Cl | Me | OCF₃ |
| Et | Cl | Cl | Me | OCF₃ |
| Et | Me | Br | Me | OCF₃ |
| Et | Cl | Br | Me | OCF₃ |
| Me | Me | H | Me | OCF₃ |
| Me | Cl | H | Me | OCF₃ |
| Me | Me | Cl | Me | OCF₃ |
| Me | Cl | Cl | Me | OCF₃ |
| Me | Me | Br | Me | OCF₃ |
| Me | Cl | Br | Me | OCF₃ |
| H | Me | H | Me | CF(CF₃)₂ |
| H | Cl | H | Me | CF(CF₃)₂ |
| H | Me | Cl | Me | CF(CF₃)₂ |
| H | Cl | Cl | Me | CF(CF₃)₂ |
| H | Me | Br | Me | CF(CF₃)₂ |
| H | Cl | Br | Me | CF(CF₃)₂ |
| i-Pr | Me | H | Me | CF(CF₃)₂ |
| i-Pr | Cl | H | Me | CF(CF₃)₂ |
| i-Pr | Me | Cl | Me | CF(CF₃)₂ |
| i-Pr | Cl | Cl | Me | CF(CF₃)₂ |
| i-Pr | Me | Br | Me | CF(CF₃)₂ |
| i-Pr | Cl | Br | Me | CF(CF₃)₂ |
| t-Bu | Me | H | Me | CF(CF₃)₂ |
| t-Bu | Cl | H | Me | CF(CF₃)₂ |

TABLE 4-continued

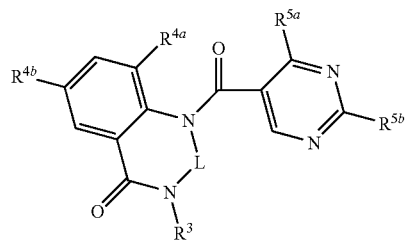

| R³ | R⁴ᵃ | R⁴ᵇ | R⁵ᵃ | R⁵ᵇ |
|---|---|---|---|---|
| t-Bu | Me | Cl | Me | CF(CF₃)₂ |
| t-Bu | Cl | Cl | Me | CF(CF₃)₂ |
| t-Bu | Me | Br | Me | CF(CF₃)₂ |
| t-Bu | Cl | Br | Me | CF(CF₃)₂ |
| Et | Me | H | Me | CF(CF₃)₂ |
| Et | Cl | H | Me | CF(CF₃)₂ |
| Et | Me | Cl | Me | CF(CF₃)₂ |
| Et | Cl | Cl | Me | CF(CF₃)₂ |
| Et | Me | Br | Me | CF(CF₃)₂ |
| Et | Cl | Br | Me | CF(CF₃)₂ |
| Me | Me | H | Me | CF(CF₃)₂ |
| Me | Cl | H | Me | CF(CF₃)₂ |
| Me | Me | Cl | Me | CF(CF₃)₂ |
| Me | Cl | Cl | Me | CF(CF₃)₂ |
| Me | Me | Br | Me | CF(CF₃)₂ |
| Me | Cl | Br | Me | CF(CF₃)₂ |

TABLE 5

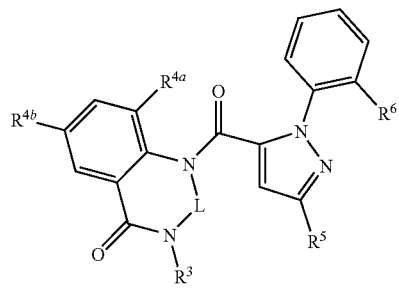

| R³ | R⁴ᵃ | R⁴ᵇ | R⁵ | R⁶ |
|---|---|---|---|---|
| L is C=O |  |  |  |  |
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |

TABLE 5-continued

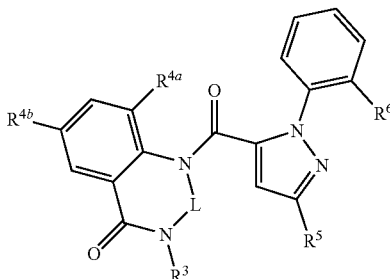

| R³ | R⁴ᵃ | R⁴ᵇ | R⁵ | R⁶ |
|---|---|---|---|---|
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |

TABLE 5-continued

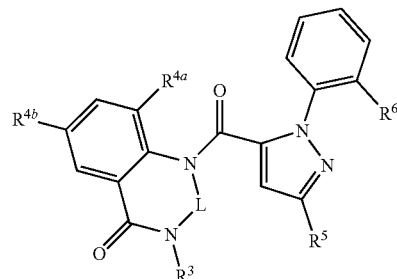

| R³ | R⁴ᵃ | R⁴ᵇ | R⁵ | R⁶ |
|---|---|---|---|---|
| Me | Me | Br | Br | Cl |
| Me | Cl | Br | Br | Cl |
| | | L is CH₂ | | |
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| i-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |

TABLE 5-continued

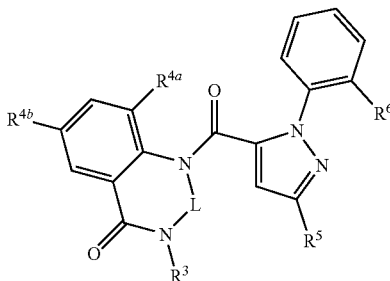

| R³ | R⁴ᵃ | R⁴ᵇ | R⁵ | R⁶ |
|---|---|---|---|---|
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |
| L is CH₂CH₂ | | | | |
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |

TABLE 5-continued

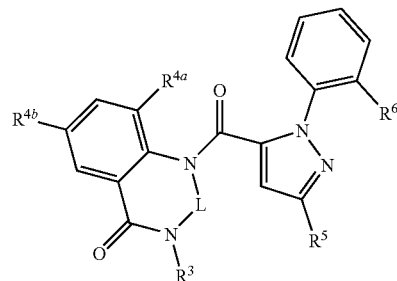

| R³ | R⁴ᵃ | R⁴ᵇ | R⁵ | R⁶ |
|---|---|---|---|---|
| Me | Me | Br | CF₃ | Cl |
| Me | Cl | Br | CF₃ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |

TABLE 5-continued

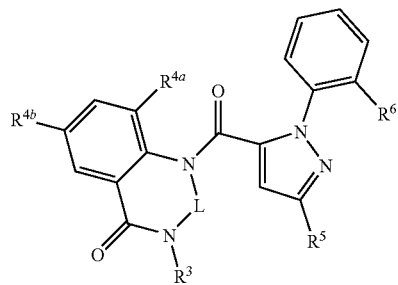

| $R^3$ | $R^{4a}$ | $R^{4b}$ | $R^5$ | $R^6$ |
|---|---|---|---|---|
| Me | Me | Br | Br | Cl |
| Me | Cl | Br | Br | Cl |

TABLE 6

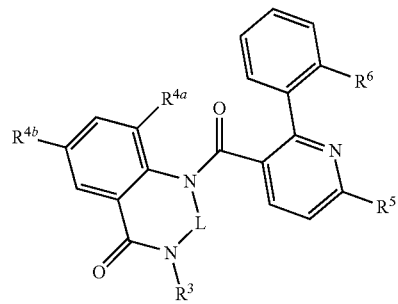

| $R^3$ | $R^{4a}$ | $R^{4b}$ | $R^5$ | $R^6$ |
|---|---|---|---|---|
| L is C=O | | | | |
| H | Me | H | CF$_3$ | Cl |
| H | Cl | H | CF$_3$ | Cl |
| H | Me | Cl | CF$_3$ | Cl |
| H | Cl | Cl | CF$_3$ | Cl |
| H | Me | Br | CF$_3$ | Cl |
| H | Cl | Br | CF$_3$ | Cl |
| i-Pr | Me | H | CF$_3$ | Cl |
| i-Pr | Cl | H | CF$_3$ | Cl |
| i-Pr | Me | Cl | CF$_3$ | Cl |
| i-Pr | Cl | Cl | CF$_3$ | Cl |
| i-Pr | Me | Br | CF$_3$ | Cl |
| i-Pr | Cl | Br | CF$_3$ | Cl |
| t-Bu | Me | H | CF$_3$ | Cl |
| t-Bu | Cl | H | CF$_3$ | Cl |
| t-Bu | Me | Cl | CF$_3$ | Cl |
| t-Bu | Cl | Cl | CF$_3$ | Cl |
| t-Bu | Me | Br | CF$_3$ | Cl |
| t-Bu | Cl | Br | CF$_3$ | Cl |
| Et | Me | H | CF$_3$ | Cl |
| Et | Cl | H | CF$_3$ | Cl |
| Et | Me | Cl | CF$_3$ | Cl |
| Et | Cl | Cl | CF$_3$ | Cl |
| Et | Me | Br | CF$_3$ | Cl |
| Et | Cl | Br | CF$_3$ | Cl |
| Me | Me | H | CF$_3$ | Cl |
| Me | Cl | H | CF$_3$ | Cl |
| Me | Me | Cl | CF$_3$ | Cl |
| Me | Cl | Cl | CF$_3$ | Cl |
| Me | Me | Br | CF$_3$ | Cl |
| Me | Cl | Br | CF$_3$ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |

TABLE 6-continued

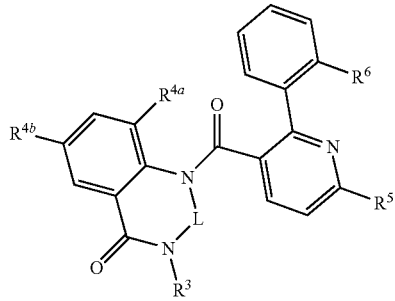

| $R^3$ | $R^{4a}$ | $R^{4b}$ | $R^5$ | $R^6$ |
|---|---|---|---|---|
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |
| L is CH$_2$ | | | | |
| H | Me | H | CF$_3$ | Cl |
| H | Cl | H | CF$_3$ | Cl |
| H | Me | Cl | CF$_3$ | Cl |
| H | Cl | Cl | CF$_3$ | Cl |
| H | Me | Br | CF$_3$ | Cl |
| H | Cl | Br | CF$_3$ | Cl |

TABLE 6-continued

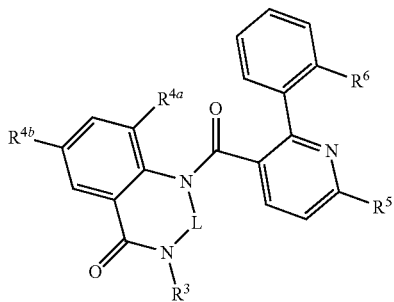

| R³ | R⁴ᵃ | R⁴ᵇ | R⁵ | R⁶ |
|---|---|---|---|---|
| i-Pr | Me | H | $CF_3$ | Cl |
| i-Pr | Cl | H | $CF_3$ | Cl |
| i-Pr | Me | Cl | $CF_3$ | Cl |
| i-Pr | Cl | Cl | $CF_3$ | Cl |
| i-Pr | Me | Br | $CF_3$ | Cl |
| i-Pr | Cl | Br | $CF_3$ | Cl |
| t-Bu | Me | H | $CF_3$ | Cl |
| t-Bu | Cl | H | $CF_3$ | Cl |
| t-Bu | Me | Cl | $CF_3$ | Cl |
| t-Bu | Cl | Cl | $CF_3$ | Cl |
| t-Bu | Me | Br | $CF_3$ | Cl |
| t-Bu | Cl | Br | $CF_3$ | Cl |
| Et | Me | H | $CF_3$ | Cl |
| Et | Cl | H | $CF_3$ | Cl |
| Et | Me | Cl | $CF_3$ | Cl |
| Et | Cl | Cl | $CF_3$ | Cl |
| Et | Me | Br | $CF_3$ | Cl |
| Et | Cl | Br | $CF_3$ | Cl |
| Me | Me | H | $CF_3$ | Cl |
| Me | Cl | H | $CF_3$ | Cl |
| Me | Me | Cl | $CF_3$ | Cl |
| Me | Cl | Cl | $CF_3$ | Cl |
| Me | Me | Br | $CF_3$ | Cl |
| Me | Cl | Br | $CF_3$ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |

TABLE 6-continued

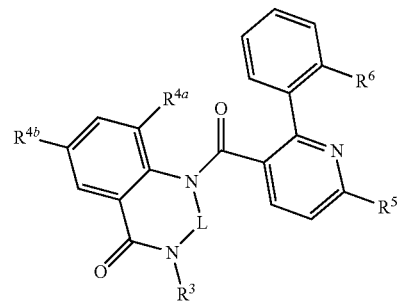

| R³ | R⁴ᵃ | R⁴ᵇ | R⁵ | R⁶ |
|---|---|---|---|---|
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |
| L is $CH_2CH_2$ | | | | |
| H | Me | H | $CF_3$ | Cl |
| H | Cl | H | $CF_3$ | Cl |
| H | Me | Cl | $CF_3$ | Cl |
| H | Cl | Cl | $CF_3$ | Cl |
| H | Me | Br | $CF_3$ | Cl |
| H | Cl | Br | $CF_3$ | Cl |
| i-Pr | Me | H | $CF_3$ | Cl |
| i-Pr | Cl | H | $CF_3$ | Cl |
| i-Pr | Me | Cl | $CF_3$ | Cl |
| i-Pr | Cl | Cl | $CF_3$ | Cl |
| i-Pr | Me | Br | $CF_3$ | Cl |
| i-Pr | Cl | Br | $CF_3$ | Cl |
| t-Bu | Me | H | $CF_3$ | Cl |
| t-Bu | Cl | H | $CF_3$ | Cl |
| t-Bu | Me | Cl | $CF_3$ | Cl |
| t-Bu | Cl | Cl | $CF_3$ | Cl |
| t-Bu | Me | Br | $CF_3$ | Cl |
| t-Bu | Cl | Br | $CF_3$ | Cl |
| Et | Me | H | $CF_3$ | Cl |
| Et | Cl | H | $CF_3$ | Cl |
| Et | Me | Cl | $CF_3$ | Cl |
| Et | Cl | Cl | $CF_3$ | Cl |
| Et | Me | Br | $CF_3$ | Cl |
| Et | Cl | Br | $CF_3$ | Cl |
| Me | Me | H | $CF_3$ | Cl |
| Me | Cl | H | $CF_3$ | Cl |
| Me | Me | Cl | $CF_3$ | Cl |
| Me | Cl | Cl | $CF_3$ | Cl |
| Me | Me | Br | $CF_3$ | Cl |
| Me | Cl | Br | $CF_3$ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |

TABLE 6-continued

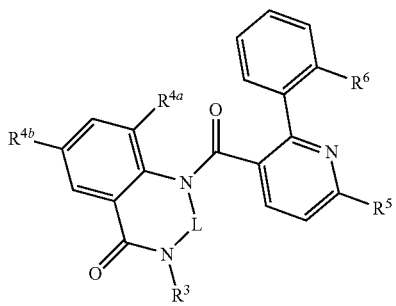

| $R^3$ | $R^{4a}$ | $R^{4b}$ | $R^5$ | $R^6$ |
|---|---|---|---|---|
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |

TABLE 7

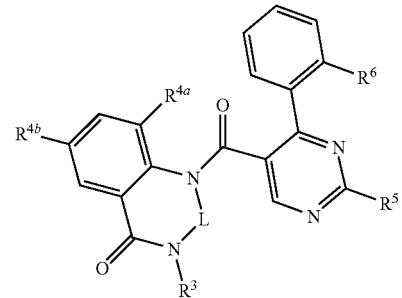

| $R^3$ | $R^{4a}$ | $R^{4b}$ | $R^5$ | $R^6$ |
|---|---|---|---|---|
| L is C=O ||||| 
| H | Me | H | $CF_3$ | Cl |
| H | Cl | H | $CF_3$ | Cl |
| H | Me | Cl | $CF_3$ | Cl |
| H | Cl | Cl | $CF_3$ | Cl |
| H | Me | Br | $CF_3$ | Cl |
| H | Cl | Br | $CF_3$ | Cl |
| i-Pr | Me | H | $CF_3$ | Cl |
| i-Pr | Cl | H | $CF_3$ | Cl |
| i-Pr | Me | Cl | $CF_3$ | Cl |
| i-Pr | Cl | Cl | $CF_3$ | Cl |
| i-Pr | Me | Br | $CF_3$ | Cl |
| i-Pr | Cl | Br | $CF_3$ | Cl |
| t-Bu | Me | H | $CF_3$ | Cl |
| t-Bu | Cl | H | $CF_3$ | Cl |
| t-Bu | Me | Cl | $CF_3$ | Cl |
| t-Bu | Cl | Cl | $CF_3$ | Cl |
| t-Bu | Me | Br | $CF_3$ | Cl |
| t-Bu | Cl | Br | $CF_3$ | Cl |
| Et | Me | H | $CF_3$ | Cl |
| Et | Cl | H | $CF_3$ | Cl |
| Et | Me | Cl | $CF_3$ | Cl |
| Et | Cl | Cl | $CF_3$ | Cl |
| Et | Me | Br | $CF_3$ | Cl |
| Et | Cl | Br | $CF_3$ | Cl |
| Me | Me | H | $CF_3$ | Cl |
| Me | Cl | H | $CF_3$ | Cl |
| Me | Me | Cl | $CF_3$ | Cl |
| Me | Cl | Cl | $CF_3$ | Cl |
| Me | Me | Br | $CF_3$ | Cl |
| Me | Cl | Br | $CF_3$ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |

TABLE 7-continued

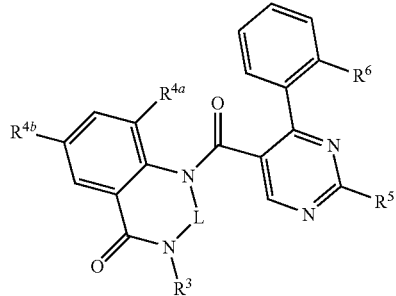

| R³ | R⁴ᵃ | R⁴ᵇ | R⁵ | R⁶ |
|---|---|---|---|---|
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |
| L is CH₂ | | | | |
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |

TABLE 7-continued

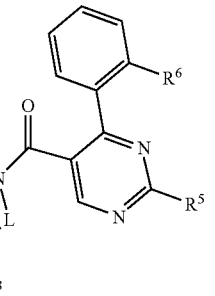

| R³ | R⁴ᵃ | R⁴ᵇ | R⁵ | R⁶ |
|---|---|---|---|---|
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| i-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |

TABLE 7-continued

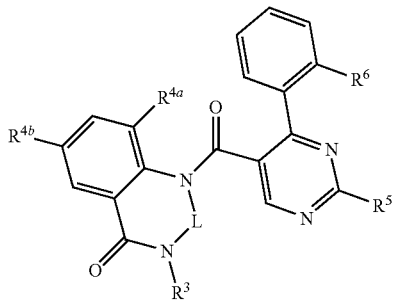

| R³ | R⁴ᵃ | R⁴ᵇ | R⁵ | R⁶ |
|---|---|---|---|---|
| Me | Me | Br | Br | Cl |
| Me | Cl | Br | Br | Cl |
| | | L is CH₂CH₂ | | |
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |

TABLE 7-continued

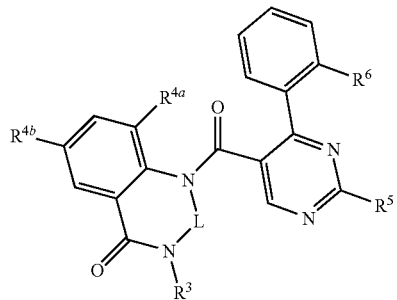

| R³ | R⁴ᵃ | R⁴ᵇ | R⁵ | R⁶ |
|---|---|---|---|---|
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |

TABLE 8

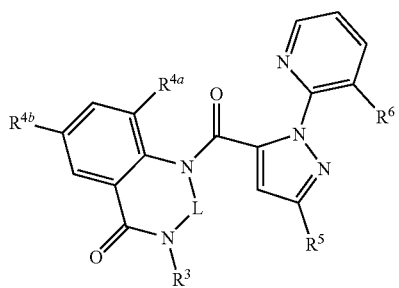

| R³ | R⁴ᵃ | R⁴ᵇ | R⁵ | R⁶ |
|---|---|---|---|---|
| | | L is C=O | | |
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |

TABLE 8-continued

| R³ | R⁴ᵃ | R⁴ᵇ | R⁵ | R⁶ |
|---|---|---|---|---|
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |

L is CH₂

| R³ | R⁴ᵃ | R⁴ᵇ | R⁵ | R⁶ |
|---|---|---|---|---|
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | CN | CF₃ | Cl |
| Me | Me | CN | CF₃ | Cl |
| i-Pr | Me | CN | CF₃ | Cl |
| H | Me | CN | CF₃ | F |
| Me | Me | CN | CF₃ | F |
| i-Pr | Me | CN | CF₃ | F |
| H | Br | F | CF₃ | Cl |
| Me | Br | F | CF₃ | Cl |

TABLE 8-continued

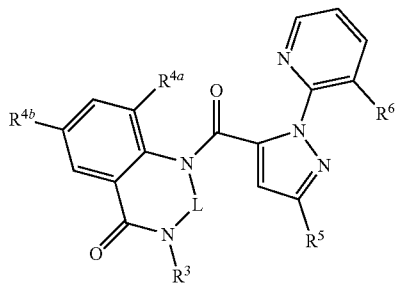

| R³ | R⁴ᵃ | R⁴ᵇ | R⁵ | R⁶ |
|---|---|---|---|---|
| i-Pr | Br | F | CF₃ | Cl |
| H | Br | F | CF₃ | F |
| Me | Br | F | CF₃ | F |
| i-Pr | Br | F | CF₃ | F |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | CN | Cl | Cl |
| Me | Me | CN | Cl | Cl |
| i-Pr | Me | CN | Cl | Cl |
| H | Me | CN | Cl | F |
| Me | Me | CN | Cl | F |
| i-Pr | Me | CN | Cl | F |
| H | Br | F | Cl | Cl |
| Me | Br | F | Cl | Cl |
| i-Pr | Br | F | Cl | Cl |
| H | Br | F | Cl | F |
| Me | Br | F | Cl | F |
| i-Pr | Br | F | Cl | F |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |

TABLE 8-continued

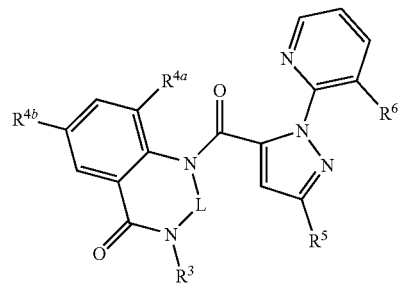

| R³ | R⁴ᵃ | R⁴ᵇ | R⁵ | R⁶ |
|---|---|---|---|---|
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |
| H | Me | CN | Br | Cl |
| Me | Me | CN | Br | Cl |
| i-Pr | Me | CN | Br | Cl |
| H | Me | CN | Br | F |
| Me | Me | CN | Br | F |
| i-Pr | Me | CN | Br | F |
| H | Br | F | Br | Cl |
| Me | Br | F | Br | Cl |
| i-Pr | Br | F | Br | Cl |
| H | Br | F | Br | F |
| Me | Br | F | Br | F |
| i-Pr | Br | F | Br | F |
| L is CH₂CH₂ | | | | |
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | H | Cl | Cl |
| H | Cl | H | Cl | Cl |
| H | Me | Cl | Cl | Cl |
| H | Cl | Cl | Cl | Cl |

TABLE 8-continued

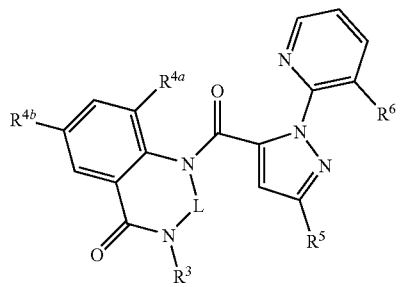

| R³ | R⁴ᵃ | R⁴ᵇ | R⁵ | R⁶ |
|---|---|---|---|---|
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |

TABLE 9

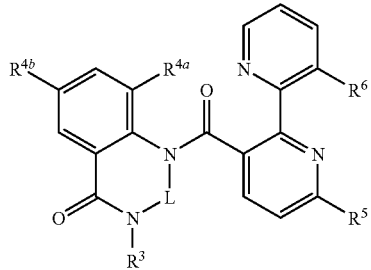

| R³ | R⁴ᵃ | R⁴ᵇ | R⁵ | R⁶ |
|---|---|---|---|---|
| L is C=O | | | | |
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |

TABLE 9-continued

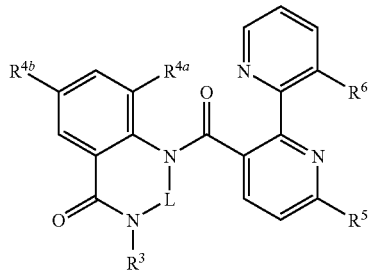

| R³ | R⁴ᵃ | R⁴ᵇ | R⁵ | R⁶ |
|---|---|---|---|---|
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |

L is CH₂

| R³ | R⁴ᵃ | R⁴ᵇ | R⁵ | R⁶ |
|---|---|---|---|---|
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | H | Cl | Cl |
| H | Cl | H | Cl | Cl |

TABLE 9-continued

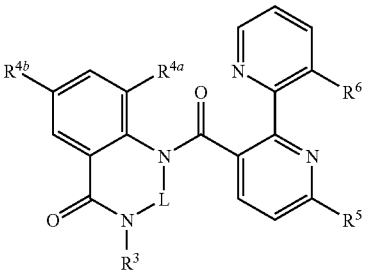

| R³ | R⁴ᵃ | R⁴ᵇ | R⁵ | R⁶ |
|---|---|---|---|---|
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |

L is CH₂CH₂

| R³ | R⁴ᵃ | R⁴ᵇ | R⁵ | R⁶ |
|---|---|---|---|---|
| H | Me | H | CF₃ | Cl |
| H | Cl | H | CF₃ | Cl |
| H | Me | Cl | CF₃ | Cl |

TABLE 9-continued

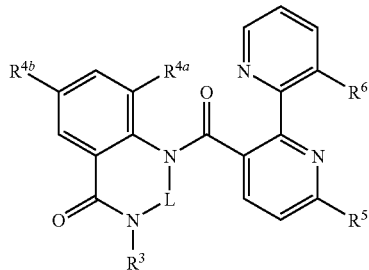

| R³ | R⁴ᵃ | R⁴ᵇ | R⁵ | R⁶ |
|---|---|---|---|---|
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |

TABLE 9-continued

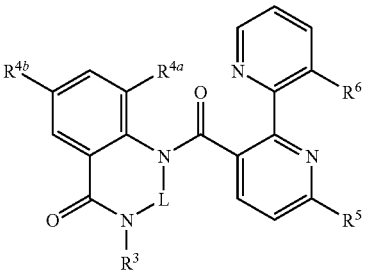

| R³ | R⁴ᵃ | R⁴ᵇ | R⁵ | R⁶ |
|---|---|---|---|---|
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |

TABLE 10

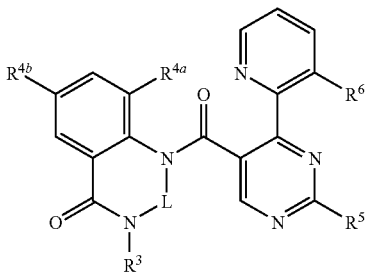

| R³ | R⁴ᵃ | R⁴ᵇ | R⁵ | R⁶ |
|---|---|---|---|---|
| L is C=O |||||
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |

TABLE 10-continued

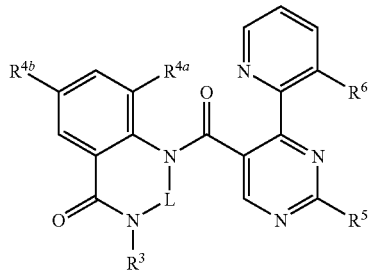

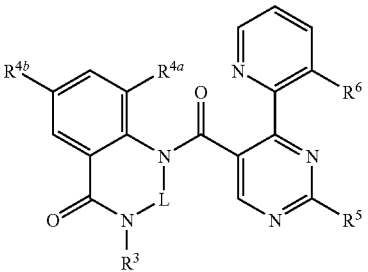

| R³ | R⁴ᵃ | R⁴ᵇ | R⁵ | R⁶ |
|---|---|---|---|---|
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |

L is CH₂

| R³ | R⁴ᵃ | R⁴ᵇ | R⁵ | R⁶ |
|---|---|---|---|---|
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |

TABLE 10-continued

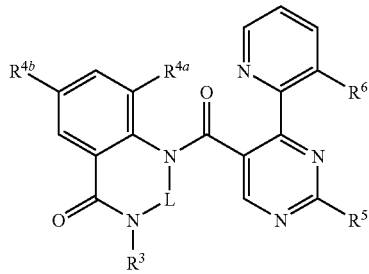

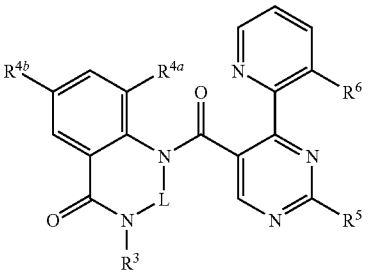

| R³ | R⁴ᵃ | R⁴ᵇ | R⁵ | R⁶ |
|---|---|---|---|---|
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |
| L is CH₂CH₂ | | | | |
| H | Me | H | CF₃ | Cl |
| H | Cl | H | CF₃ | Cl |
| H | Me | Cl | CF₃ | Cl |
| H | Cl | Cl | CF₃ | Cl |
| H | Me | Br | CF₃ | Cl |
| H | Cl | Br | CF₃ | Cl |
| i-Pr | Me | H | CF₃ | Cl |
| i-Pr | Cl | H | CF₃ | Cl |
| i-Pr | Me | Cl | CF₃ | Cl |
| i-Pr | Cl | Cl | CF₃ | Cl |
| i-Pr | Me | Br | CF₃ | Cl |
| i-Pr | Cl | Br | CF₃ | Cl |
| t-Bu | Me | H | CF₃ | Cl |
| t-Bu | Cl | H | CF₃ | Cl |
| t-Bu | Me | Cl | CF₃ | Cl |
| t-Bu | Cl | Cl | CF₃ | Cl |
| t-Bu | Me | Br | CF₃ | Cl |
| t-Bu | Cl | Br | CF₃ | Cl |
| Et | Me | H | CF₃ | Cl |
| Et | Cl | H | CF₃ | Cl |
| Et | Me | Cl | CF₃ | Cl |
| Et | Cl | Cl | CF₃ | Cl |
| Et | Me | Br | CF₃ | Cl |
| Et | Cl | Br | CF₃ | Cl |
| Me | Me | H | CF₃ | Cl |
| Me | Cl | H | CF₃ | Cl |
| Me | Me | Cl | CF₃ | Cl |
| Me | Cl | Cl | CF₃ | Cl |
| Me | Me | Br | CF₃ | Cl |
| Me | Cl | Br | CF₃ | Cl |
| H | Me | H | Cl | Cl |
| H | Cl | H | Cl | Cl |
| H | Me | Cl | Cl | Cl |
| H | Cl | Cl | Cl | Cl |
| H | Me | Br | Cl | Cl |
| H | Cl | Br | Cl | Cl |
| i-Pr | Me | H | Cl | Cl |
| i-Pr | Cl | H | Cl | Cl |
| i-Pr | Me | Cl | Cl | Cl |
| i-Pr | Cl | Cl | Cl | Cl |
| i-Pr | Me | Br | Cl | Cl |
| i-Pr | Cl | Br | Cl | Cl |
| t-Bu | Me | H | Cl | Cl |
| t-Bu | Cl | H | Cl | Cl |
| t-Bu | Me | Cl | Cl | Cl |
| t-Bu | Cl | Cl | Cl | Cl |
| t-Bu | Me | Br | Cl | Cl |
| t-Bu | Cl | Br | Cl | Cl |
| Et | Me | H | Cl | Cl |
| Et | Cl | H | Cl | Cl |
| Et | Me | Cl | Cl | Cl |
| Et | Cl | Cl | Cl | Cl |
| Et | Me | Br | Cl | Cl |
| Et | Cl | Br | Cl | Cl |
| Me | Me | H | Cl | Cl |
| Me | Cl | H | Cl | Cl |
| Me | Me | Cl | Cl | Cl |
| Me | Cl | Cl | Cl | Cl |
| Me | Me | Br | Cl | Cl |
| Me | Cl | Br | Cl | Cl |
| H | Me | H | Br | Cl |
| H | Cl | H | Br | Cl |
| H | Me | Cl | Br | Cl |
| H | Cl | Cl | Br | Cl |
| H | Me | Br | Br | Cl |
| H | Cl | Br | Br | Cl |
| i-Pr | Me | H | Br | Cl |
| i-Pr | Cl | H | Br | Cl |
| i-Pr | Me | Cl | Br | Cl |
| i-Pr | Cl | Cl | Br | Cl |
| i-Pr | Me | Br | Br | Cl |
| i-Pr | Cl | Br | Br | Cl |
| t-Bu | Me | H | Br | Cl |
| t-Bu | Cl | H | Br | Cl |
| t-Bu | Me | Cl | Br | Cl |
| t-Bu | Cl | Cl | Br | Cl |
| t-Bu | Me | Br | Br | Cl |
| t-Bu | Cl | Br | Br | Cl |
| Et | Me | H | Br | Cl |
| Et | Cl | H | Br | Cl |
| Et | Me | Cl | Br | Cl |
| Et | Cl | Cl | Br | Cl |
| Et | Me | Br | Br | Cl |
| Et | Cl | Br | Br | Cl |

TABLE 10-continued

[Chemical structure showing a compound with substituents $R^{4b}$, $R^{4a}$, $R^3$, $R^5$, $R^6$ and an L linker]

| $R^3$ | $R^{4a}$ | $R^{4b}$ | $R^5$ | $R^6$ |
|---|---|---|---|---|
| Me | Me | H | Br | Cl |
| Me | Cl | H | Br | Cl |
| Me | Me | Cl | Br | Cl |
| Me | Cl | Cl | Br | Cl |
| Me | Me | Br | Br | Cl |
| Me | Cl | Br | Br | Cl |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

| | Weight Percent | | |
|---|---|---|---|
| | Active Ingredient | Diluent | Surfactant |
| Water-Dispersible and Water-soluble Granules, Tablets and Powders. | 5-90 | 0-94 | 1-15 |
| Suspensions, Emulsions, Solutions (including Emulsifiable Concentrates) | 5-50 | 40-95 | 0-15 |
| Dusts | 1-25 | 70-99 | 0-5 |
| Granules and Pellets | 0.01-99 | 5-99.99 | 0-15 |
| High Strength Compositions | 90-99 | 0-10 | 0-2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Table A.

EXAMPLE A

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

Granule

| | |
|---|---|
| Compound 1 | 10.0% |
| attapulgite granules (low volatile matter, 0.71/0.30 mm; U.S.S. No. 25-50 sieves) | 90.0%. |

EXAMPLE C

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

Emulsifiable Concentrate

| | |
|---|---|
| Compound 1 | 20.0% |
| blend of oil soluble sulfonates and polyoxyethylene ethers | 10.0% |
| isophorone | 70.0%. |

EXAMPLE E

Granule

| | |
|---|---|
| Compound 1 | 0.5% |
| cellulose | 2.5% |
| lactose | 4.0% |
| cornmeal | 93.0%. |

Compounds of this invention are characterized by favorable metabolic and/or soil residual patterns and exhibit activity controlling a spectrum of agronomic and non-agronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), public (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition it includes: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Activity also includes members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnis-* tis citrella Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifoli* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla). These compounds also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Franklin-*

*iella occidentalis* Pergande (western flower thrip), *Scirtothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus compositions of the present invention can further comprise a biologically effective amount of at least one additional biologically active compound or agent. Examples of such biologically active compounds or agents with which compounds of this invention can be formulated are: insecticides such as abamectin, acephate, acetamiprid, avermectin, azadirachtin, azinphosmethyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, oxamyl, parathion, parathion-methyl, permethrin, phorate, phosalone, phosmet, phosphamidon, pirimicarb, profenofos, pymetrozine, pyridalyl, pyriproxyfen, rotenone, spinosad, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), myclobutanil, neoasozin (ferric methanearsonate), oxadixyl, penconazole, pencycuron, probenazole, prochloraz, propamocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki*, *Bacillus thuringiensis* delta endotoxin, baculovirus, and entomopathogenic bacteria, virus and fungi.

A general reference for these agricultural protectants is *The Pesticide Manual, 12th Edition*, C. D. S. Tomlin, Ed., British Crop Protection Council, Farnham, Surrey, U.K., 2000.

Preferred insecticides and acaricides for mixing with compounds of this invention include pyrethroids such as cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of invention can also provide a broader spectrum of plant protection and be advantageous for resistance management.

Invertebrate pests are controlled in agronomic and nonagronomic applications by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of invertebrates in agronomic and/or nonagronomic applications, comprising contacting the invertebrates or their environment with a biologically effective amount of one or more of the compounds of the invention, or with a composition comprising at least one such compound or a composition comprising at least one such compound and an effective amount of at least one additional biologically active compound or agent.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, seed coatings, microencapsulations, systemic uptake, baits, eartags, boluses, foggers, fumigants, aerosols, dusts and many others.

The compounds of this invention can be incorporated into baits that are consumed by the invertebrates or within devices such as traps and the like. Granules or baits comprising between 0.01-5% active ingredient, 0.05-10% moisture retaining agent(s) and 40-99% vegetable flour are effective in controlling soil insects at very low application rates, particularly at doses of active ingredient that are lethal by ingestion rather than by direct contact.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrates, spreader stickers, adjuvants, other solvents, and synergists such as piperonyl butoxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following Tests in the Biological Examples of the Invention demonstrate the efficacy of methods of the invention for protecting plants from specific arthropod pests. "Control efficacy" represents inhibition of arthropod development (including mortality) that causes significantly reduced feeding. The pest control protection afforded by the compounds is not limited, however, to these species. See Index Tables A-D for compound descriptions. The following abbreviations are used in the Index Tables that follow: t is tertiary, n is normal, i is iso, s is secondary, c is cyclo, Me is methyl, Et is ethyl, Pr is propyl and Bu is butyl; accordingly i-Pr is isopropyl, s-Bu is secondary butyl, etc. The abbreviation "Ex." stands for "Example" and is followed by a number indicating in which example the compound is prepared.

INDEX TABLE A

| Compound | $R^3$ | $R^{4a}$ | $R^{4b}$ | $R^5$ | m.p. (° C.) |
|---|---|---|---|---|---|
| 1 | i-Pr | Me | H | $CF_3$ | * |
| 2 | Me | Me | Br | $CF_3$ | * |
| 3 | i-Pr | Me | Br | $CF_3$ | * |
| 4 | t-Bu | Me | Br | $CF_3$ | * |
| 5 | Me | Me | Br | Br | * |
| 6 (Ex. 1) | i-Pr | Me | Br | Br | * |

*See Index Table D for $^1$H NMR data.

INDEX TABLE B

| Compound | $R^3$ | $R^{4a}$ | $R^{4b}$ | $R^5$ | $R^{13}$ | m.p. (° C.) |
|---|---|---|---|---|---|---|
| 7 (Ex. 2) | i-Pr | Me | H | Br | H | * |
| 8 | i-Pr | Cl | Cl | Cl | H | 192-194 |
| 9 | i-Pr | Cl | Cl | Br | H | 207-208 |
| 10 | i-Pr | Cl | Cl | $CF_3$ | H | 167-168 |
| 11 | Me | Cl | Cl | Cl | H | 173-178 |
| 12 | Me | Cl | Cl | Br | H | 200-202 |
| 13 | Me | Cl | Cl | $CF_3$ | H | 157-158 |
| 14 | i-Pr | Me | Cl | Cl | H | 219-220 |
| 15 | i-Pr | Me | Cl | Br | H | 228-231 |
| 16 | i-Pr | Me | Cl | $CF_3$ | H | 213-214 |
| 17 | Me | Me | Cl | Cl | H | 238-240 |
| 18 | Me | Me | Cl | Br | H | 254-255 |
| 19 | Me | Me | Cl | $CF_3$ | H | 207-208 |
| 20 | i-Pr | Me | H | Cl | $CO_2H$ | 143-190 |
| 21 | Me | Cl | Cl | Cl | $CO_2H$ | * |
| 22 | Cl | Cl | Cl | Cl | 3-pyridyl | 135-156 |
| 23 | Cl | Cl | Cl | Cl | 2-imidazolyl | * |
| 24 | Cl | Cl | Cl | Cl | 4-imidazolyl | * |
| 25 | Me | Cl | Cl | Cl | $CO_2Et$ | * |
| 26 | Me | Cl | Cl | Cl | $CH_2CO_2Me$ | * |
| 27 | Me | Cl | Cl | Cl | 4-$(CO_2Me)$Ph | 178-232 |
| 28 | H | Cl | Cl | Cl | H | 181-192 |
| 29 | H | Cl | Cl | $CF_3$ | H | 162-177 |

*See Index Table D for $^1$H NMR data.

INDEX TABLE C

| Compound | $R^3$ | $R^{4a}$ | $R^{4b}$ | $R^5$ | m.p. (° C.) |
|---|---|---|---|---|---|
| 30 | H | Cl | Cl | Cl | * |
| 31 | H | Cl | Cl | $CF_3$ | * |

*See Index Table D for $^1$H NMR data.

INDEX TABLE D

| Cmpd No. | $^1$H NMR Data (CDCl$_3$ solution unless indicated otherwise)$^a$ |
|---|---|
| 1 | DMSO-d$_6$ 8.6-8.5(dd, 1H), 8.4(dd, 1H), 8.29(s, 1H), 8.0(d, 1H), 7.8(dd, 1H), 7.6(d, 1H), 7.4-7.3(t, 1H), 5.0(m, 1H), 2.08(s, 3H), 1.41(d, 6H). |
| 2 | 8.41(dd, 1H), 8.21(d, 1H), 7.96(dd, 1H), 7.58(d, 1H), 7.45(dd, 1H), 7.38(s, 1H), 3.40(s, 3H), 2.16(s, 3H). |
| 3 | 8.36(dd, 1H), 8.17(d, 1H), 7.94(dd, 1H), 7.56(d, 1H), 7.42(dd, 1H), 7.37(s, 1H), 5.08(m, 1H), 2.16(s, 3H), 1.46(d, 6H). |
| 4 | 8.44(dd, 1H), 8.02(d, 1H), 7.95(dd, 1H), 7.52(d, 1H), 7.45(dd, 1H), 7.28(s, 1H), 2.11(s, 3H), 1.64(s, 9H). |
| 5 | 8.39(dd, 1H), 8.20(d, 1H), 7.93(dd, 1H), 7.57(d, 1H), 7.41(dd, 1H), 7.12(s, 1H), 3.40(s, 3H), 2.16(s, 3H). |
| 6 | 8.34(dd, 1H), 8.17(d, 1H), 7.91(dd, 1H), 7.54(d, 1H), 7.39(dd, 1H), 7.12(s, 1H), 5.08(m, 1H), 2.17(s, 3H), 1.47(d, 6H). |
| 7 | 8.3(m, 1H), 7.9-7.8(m, 2H), 7.4-7.3(m, 3H), 6.0-5.9(s, 1H), 5.9(d, 1H), 5.0-4.8(m, 1H), 4.4-4.3(d, 1H), 2.10(s, 3H), 1.3-1.1(m, 6H) |
| 21 | DMSO-d$_6$ 8.50(dd, 1H), 8.21(d, 1H), 7.87-7.75(m, 2H), 7.61(ddd, 1H), 5.83(bs, 1H), 3.01(s, 3H) |
| 23 | DMSO-d$_6$ 8.38(d, 1H), 8.22(bs, 1H), 7.9-7.7(bm, 2H), 7.58(t, 1H), 7.16-7.05(m, 2H), 6.83(bs, 1H), 3.15(bs, 3H) |
| 24 | DMSO-d$_6$ 8.48(s, 1H), 8.24(d, 1H), 7.87-7.77(m, 2H), 7.70(s, 1H), 7.61(m, 1H), 7.01(s, 2H), 6.90(s, 1H), 3.18(bs, 3H) |
| 25 | DMSO-d$_6$ 8.4-8.2(b, 2H), 8.1-7.8(b, 2H), 7.55(b, 1H), 7.2-7.1(m, 2H), 6.8-6.6(b, 1H), 4.3-3.9(b, 2H), 3.11(s, 3H), 1.2-0.9(b, 3H) |
| 26 | DMSO-d$_6$ 8.30(d, 1H), 8.20(bs, 1H), 7.98(bs, 1H), 7.82(bs, 1H), 7.55(t, 1H), 7.41(bs, 1H), 6.08(bs, 1H), 3.60(b, 2H), 3.04(s, 3H) |
| 30 | DMSO-d$_6$ 8.27(dd, 1H), 8.09(s 1H), 8.07(dd 1H), 7.70(dd, 1H), 7.44(dd, 1H), 7.17(s, 1H), 4.44(t, 2H), 3.99(t, 2H) |
| 31 | DMSO-d$_6$ 8.24(dd, 1H), 8.03(dd 1H), 7.88(s, 1H), 7.66(s, 1H), 7.45(s, 1H), 7.40(s, 1H), 4.33(t, 2H), 3.91(t, 2H) |

$^a$ $^1$H NMR data are in ppm downfield from tetramethylsilane. Couplings are designated by (s)-singlet, (d)-doublet, (t)-triplet, (q)-quartet, (m)-multiplet, (dd)-doublet of doublets, (dt)-doublet of triplets, (br s)-broad singlet.

BIOLOGICAL EXAMPLES OF THE INVENTION

Test A

For evaluating control of diamondback moth (*Plutella xylostella*) the test unit consisted of a small open container with a 12-14-day-old radish plant inside. This was pre-infested with 10-15 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc). The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in this screen were sprayed at 50 ppm and replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed.

Of the compounds tested, the following provided excellent levels of plant protection (20% or less feeding damage): 1, 2, 3, 5, 7, 8, 9, 10, 11, 12, 13, 14, 15, 16, 17, 18, 19, 22, 23, 24, 26, 28 and 29.

Test B

For evaluating control of fall armyworm (*Spodoptera frugiperda*) the test unit consisted of a small open container with a 4-5-day-old corn (maize) plant inside. This was pre-infested with 1-15 1-day-old larvae on a piece of insect diet by use of a core sampler as described for Test A.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (20% or less feeding damage): 5, 7, 8, 9, 10, 11, 12, 13, 14, 15, 16, 17, 18, 19, 23, 24, 28 and 29.

Test C

For evaluating control of tobacco budworm (*Heliothis virescens*) the test unit consisted of a small open container with a 6-7 day old cotton plant inside. This was pre-infested with 8 2-day-old larvae on a piece of insect diet by use of a core sampler as described for Test A.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (20% or less feeding damage): 1, 2, 5, 7, 8, 9, 10, 11, 12, 13, 14, 15, 16, 17, 18, 19, 21, 23 and 24.

Test D

For evaluating control of beet armyworm (Spodoptera exigua) the test unit consisted of a small open container with a 4-5-day-old corn plant inside. This was pre-infested with 10-15 1-day-old larvae on a piece of insect diet by use of a core sampler as described for Test A.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (20% or less feeding damage): 2, 5, 7, 8, 9, 10, 11, 12, 13, 14, 15, 16, 17, 18, 19, 23 and 24.

Test E

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The larvae moved onto the test plant as the leaf piece desiccated. After pre-infestation, the soil of the test unit was covered with a layer of sand.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.). The formulated compounds were applied in 1 mL of liquid through a SUJ2 atomizer nozzle with 1/8 JJ custom body (Spraying Systems Co.) positioned 1.27 cm (0.5 inches) above the top of each test unit. All experimental compounds in this screen were sprayed at 250 ppm and replicated three times. After spraying of the formulated test compound, each test unit was allowed to dry for 1 hour and then a black, screened cap was placed on top. The test units were held for 6 days in a growth chamber at 19-21° C. and 50-70% relative humidity. Each test unit was then visually assessed for insect mortality.

Of the compounds tested, the following resulted in at least 80% mortality: 8, 9, 11, 12, 13, 19, 28 and 29.

Test F

For evaluating control of cotton melon aphid (*Aphis gossypii*) through contact and/or systemic means, the test unit consisted of a small open container with a 6-7-day-old cotton plant inside. This was pre-infested with 30-40 aphids on a piece of leaf according to the cut-leaf method described for Test E, and the soil of the test unit was covered with a layer of sand.

Test compounds were formulated and sprayed at 250 ppm as described for Test E. The applications were replicated three times. After spraying, the test units were maintained in a growth chamber and then visually rated as described for Test E.

Of the compounds tested, the following resulted in at least 80% mortality: 8, 9, 11, 12, 13, 15, 16, 19 and 29.

Test G

For evaluating control of Corn Planthopper (*Peregrinus maidis*) through contact and/or systemic means, the test unit consisted of a small open container with a 3-4 day old corn (maize) plant (spike) inside. White sand was added to the top of the soil prior to application. Test compounds were formulated and sprayed at 250 ppm and replicated three times as described for Test E. After spraying, the test units were allowed to dry for 1 hour before they were post-infested with 10-20 Corn Planthoppers (18 to 20 day old nymphs) by sprinkling them onto the sand with a salt shaker. A black, screened cap is placed on the top of the cylinder. The test units were held for 6 days in a growth chamber at 19-21° C. and 50-70% relative humidity. Each test unit was then visually assessed for insect mortality.

Of the compounds tested, the following resulted in at least 80% mortality: 12 and 13.

Test H

For evaluating control of Potato Leafhopper (*Empoasca fabae* Harris) through contact and/or systemic means, the test unit consisted of a small open container with a 5-6 day old Longio bean plant (primary leaves emerged) inside. White sand was added to the top of the soil and one of the primary leaves was excised prior to application. Test compounds were formulated and sprayed at 250 ppm and replicated three times as described for Test E. After spraying, the test units were allowed to dry for 1 hour before they were post-infested with 5 Potato Leafhoppers (18 to 21 day old adults). A black, screened cap is placed on the top of the cylinder. The test units were held for 6 days in a growth chamber at 19-21° C. and 50-70% relative humidity. Each test unit was then visually assessed for insect mortality.

Of the compounds tested, the following resulted in at least 80% mortality: 8, 9, 10, 11, 12, 13, 15, 16, 19, 24 and 29.

What is claimed is:

1. A compound of Formula 6, an N-oxide or salt thereof,

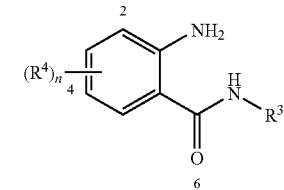

wherein
$R^3$ is H, methyl or iso-propyl;
n is 2;
one $R^4$ is in the 2-position and is methyl; and
the other $R^4$ is in the 4-position and is CN.

2. The compound of claim 1 wherein $R^3$ is H.
3. The compound of claim 1 wherein $R^3$ is methyl.
4. The compound of claim 1 wherein $R^3$ is iso-propyl.

\* \* \* \* \*